United States Patent
Lee et al.

(10) Patent No.: US 10,439,152 B2
(45) Date of Patent: Oct. 8, 2019

(54) ORGANOMETALLIC COMPOUND AND ORGANIC LIGHT-EMITTING DEVICE INCLUDING THE SAME

(71) Applicant: SAMSUNG ELECTRONICS CO., LTD., Suwon-si, Gyeonggi-do (KR)

(72) Inventors: Banglin Lee, Suwon-si (KR); Kum Hee Lee, Suwon-si (KR); Sunyoung Lee, Seoul (KR); Hyeonho Choi, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 378 days.

(21) Appl. No.: 15/389,791

(22) Filed: Dec. 23, 2016

(65) Prior Publication Data
US 2017/0256727 A1 Sep. 7, 2017

(30) Foreign Application Priority Data
Mar. 2, 2016 (KR) ........................ 10-2016-0025041

(51) Int. Cl.
| | | |
|---|---|---|
| H01L 51/54 | (2006.01) | |
| C09K 11/06 | (2006.01) | |
| H01L 51/00 | (2006.01) | |
| C07F 15/00 | (2006.01) | |
| H01L 51/50 | (2006.01) | |

(52) U.S. Cl.
CPC ...... *H01L 51/0087* (2013.01); *C07F 15/0086* (2013.01); *C09K 11/06* (2013.01); *H01L 51/0094* (2013.01); *C09K 2211/1007* (2013.01); *C09K 2211/1014* (2013.01); *C09K 2211/1029* (2013.01); *C09K 2211/1033* (2013.01); *C09K 2211/1044* (2013.01); *C09K 2211/1088* (2013.01); *C09K 2211/185* (2013.01); *H01L 51/5012* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 8,927,713 B2 | 1/2015 | Li et al. | |
| 2006/0134461 A1* | 6/2006 | Huo et al. | C07F 15/0086 428/690 |
| 2006/0172146 A1* | 8/2006 | Igarashi et al. | C07D 471/22 428/690 |
| 2012/0215001 A1 | 8/2012 | Li et al. | |
| 2014/0330019 A1 | 11/2014 | Li et al. | |
| 2015/0105556 A1* | 4/2015 | Li et al. | C09K 11/06 546/4 |

* cited by examiner

*Primary Examiner* — Marie R. Yamnitzky
(74) *Attorney, Agent, or Firm* — Cantor Colburn LLP

(57) ABSTRACT

An organometallic compound represented by Formula 1:

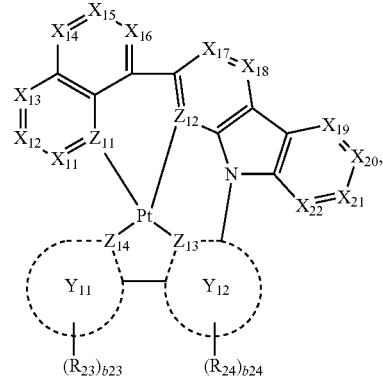

Formula 1 wherein in Formula 1, groups and variables are the same as described in the specification.

20 Claims, 2 Drawing Sheets

ORGANOMETALLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2016-0025041, filed on Mar. 2, 2016, in the Korean Intellectual Property Office, and all the benefits accruing therefrom under 35 U.S.C. § 119, the content of which is incorporated herein in its entirety by reference.

BACKGROUND

1. Field

Embodiments relate to an organometallic compound and an organic light-emitting device including the same.

2. Description of the Related Art

Organic light-emitting devices (OLEDs) are self-emission devices that have wide viewing angles, high contrast ratios, and short response times. OLEDs may also exhibit excellent brightness, driving voltage, and response speed characteristics, and produce full-color images.

In an example, an organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region.

Carriers, such as holes and electrons, recombine in the emission layer to produce excitons. These excitons transition from an excited state to a ground state, thereby generating light.

Various types of organic light emitting devices are known. However, there still remains a need in OLEDs having low driving voltage, high efficiency, high brightness, and long lifespan.

SUMMARY

Embodiments relate to an organometallic compound and an organic light-emitting device including the same.

Additional aspects will be set forth in part in the description which follows and, in part, will be apparent from the description, or may be learned by practice of the presented embodiments.

An aspect provides an organometallic compound represented by Formula 1:

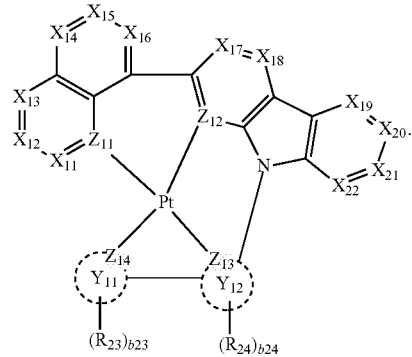

Formula 1

In Formula 1, $X_{11}$ may be selected from $C(R_{11})$ and a nitrogen atom (N); $X_{12}$ may be selected from $C(R_{12})$ and N; $X_{13}$ may be selected from $C(R_{13})$ and N; $X_{14}$ may be selected from $C(R_{14})$ and N; $X_{15}$ may be selected from $C(R_{15})$ and N; $X_{16}$ may be selected from $C(R_{16})$ and N; $X_{17}$ may be selected from $C(R_{17})$ and N; $X_{18}$ may be selected from $C(R_{18})$ and N; $X_{19}$ may be selected from $C(R_{19})$ and N; $X_{19}$ may be selected from $C(R_{19})$ and N; $X_{20}$ may be selected from $C(R_{20})$ and N; $X_{21}$ may be selected from $C(R_{21})$ and N; $X_{22}$ may be selected from $C(R_{22})$ and N;

$Z_{11}$ to $Z_{14}$ may each independently be selected from N and carbon atom (C);

$Y_{11}$ and $Y_{12}$ may each independently be selected from a $C_5$-$C_{60}$ carbocyclic group and a $C_1$-$C_{60}$ heterocyclic group; and $R_{11}$ to $R_{24}$ may each independently be selected from hydrogen, deuterium, —F, —Cl, —Br, —I, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si$(Q_3)(Q_4)(Q_5)$, Ge$(Q_3)$$(Q_4)(Q_5)$, —N$(Q_3)(Q_4)$, —B$(Q_3)(Q_4)$, —C(=O)$(Q_3)$, —S(=O)$_2(Q_3)$, and —P(=O)$(Q_3)(Q_4)$;

provided that two neighboring substituents selected from $R_{11}$ to $R_{24}$ may optionally be linked to form a substituted or unsubstituted saturated ring or a substituted or unsubstituted unsaturated ring, wherein $Q_3$ to $Q_5$ may each independently be selected from hydrogen, deuterium, a $C_1$-$C_{60}$ alkyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

An aspect provides an organic light-emitting device including:

a first electrode;

a second electrode; and an organic layer disposed between the first electrode and the second electrode, wherein the organic layer includes an emission layer and at least one organometallic compound.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
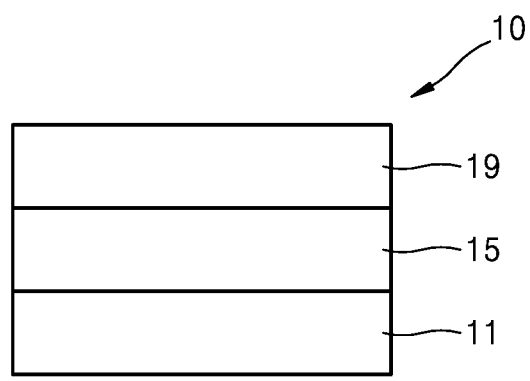
FIG. 1 is a schematic view of an organic light-emitting device according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein.

Accordingly, the embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features.

Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organometallic compound according to an embodiment of the present disclosure may be represented by Formula 1:

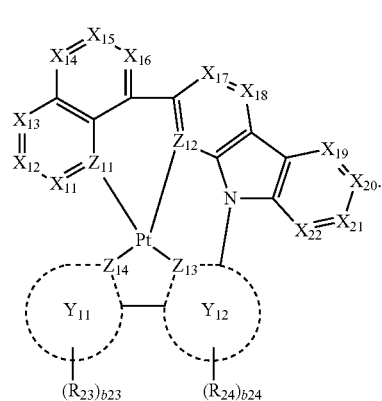

Formula 1

In Formula 1, $X_{11}$ may be selected from $C(R_{11})$ and a nitrogen atom (N); $X_{12}$ may be selected from $C(R_{12})$ and N; $X_{13}$ may be selected from $C(R_{13})$ and N; $X_{14}$ may be selected from $C(R_{14})$ and N; $X_{15}$ may be selected from $C(R_{15})$ and N; $X_{16}$ may be selected from $C(R_{16})$ and N; $X_{17}$ may be selected from $C(R_{17})$ and N; $X_{18}$ may be selected from $C(R_{18})$ and N; $X_{19}$ may be selected from $C(R_{19})$ and N; $X_{19}$ may be selected from $C(R_{19})$ and N; $X_{20}$ may be selected from $C(R_{20})$ and N; $X_{21}$ may be selected from $C(R_{21})$ and N; $X_{22}$ may be selected from $C(R_{22})$ and N, and $R_{11}$ to $R_{22}$ are the same as described below.

For example, at least one selected from $X_{11}$ to $X_{22}$ in Formula 1 may be N; or $X_{11}$ may be $C(R_{11})$; $X_{12}$ may be $C(R_{12})$; $X_{13}$ may be $C(R_{13})$; $X_{14}$ may be $C(R_{14})$; $X_{15}$ may be $C(R_{15})$; $X_{16}$ may be $C(R_{16})$; $X_{17}$ may be $C(R_{17})$; $X_{18}$ may be $C(R_{18})$; $X_{19}$ may be $C(R_{19})$; $X_{20}$ may be $C(R_{20})$; $X_{21}$ may be $C(R_{21})$; and $X_{22}$ may be $C(R_{22})$, but they are not limited thereto.

In an embodiment, in Formula 1, $X_{11}$ may be $C(R_{11})$; $X_{12}$ may be $C(R_{12})$; $X_{13}$ may be $C(R_{13})$; $X_{14}$ may be N; $X_{15}$ may be $C(R_{15})$; $X_{16}$ may be $C(R_{16})$; $X_{17}$ may be $C(R_{17})$; $X_{18}$ may be $C(R_{18})$; $X_{19}$ may be $C(R_{19})$; $X_{20}$ may be $C(R_{20})$; $X_{21}$ may be $C(R_{21})$; and $X_{22}$ may be $C(R_{22})$; or $X_{11}$ may be $C(R_{11})$; $X_{12}$ may be $C(R_{12})$; $X_{13}$ may be $C(R_{13})$; $X_{14}$ may be $C(R_{14})$; $X_{15}$ may be $C(R_{15})$; $X_{16}$ may be $C(R_{16})$; $X_{17}$ may be $C(R_{17})$; $X_{18}$ may be $C(R_{18})$; $X_{19}$ may be $C(R_{19})$; $X_{20}$ may be $C(R_{20})$; $X_{21}$ may be $C(R_{21})$; and $X_{22}$ may be $C(R_{22})$, but they are not limited thereto.

$Z_{11}$ to $Z_{14}$ in Formula 1 may each independently be selected from N and carbon atom(C).

For example, in Formula 1, $Z_{11}$ may be N, and $Z_{12}$ may be C;

$Z_{11}$ may be C, and $Z_{12}$ may be N;

$Z_{11}$ may be C, and $Z_{12}$ may be C; or $Z_{11}$ may be N, and $Z_{12}$ may be N, but they are not limited thereto.

In an embodiment, in Formula 1, $Z_{11}$ may be N, and $Z_{12}$ may be C, but they are not limited thereto.

In an embodiment, in Formula 1, $Z_{13}$ may be N, and $Z_{14}$ may be C;

$Z_{13}$ may be C, and $Z_{14}$ may be N;

$Z_{13}$ may be C, and $Z_{14}$ may be C; and $Z_{13}$ may be N, and $Z_{14}$ may be N, but they are not limited thereto.

In an embodiment, in Formula 1, $Z_{13}$ may be C, and $Z_{14}$ may be N.

In an embodiment, in Formula 1, $Z_{11}$ may be N, $Z_{12}$ may be C, $Z_{13}$ may be N, and $Z_{14}$ may be C;

$Z_{11}$ may be N, $Z_{12}$ may be C, $Z_{13}$ may be C, and $Z_{14}$ may be N;

$Z_{11}$ may be C, $Z_{12}$ may be N, $Z_{13}$ may be N, and $Z_{14}$ may be C; or $Z_{11}$ may be C, $Z_{12}$ may be N, $Z_{13}$ may be C, and $Z_{14}$ may be N, but they are not limited thereto.

In an embodiment, in Formula 1, $Z_{11}$ may be N, $Z_{12}$ may be C, $Z_{13}$ may be C, and $Z_{14}$ may be N, but they are not limited thereto.

$Y_{11}$ and $Y_{12}$ in Formula 1 may each independently be selected from a $C_5$-$C_{60}$ carbocyclic group and a $C_1$-$C_{60}$ heterocyclic group.

For example, $Y_{11}$ and $Y_{12}$ in Formula 1 may each independently be selected from a benzene group, a naphthalene group, a phenanthrene group, an anthracene group, a triphenylene group, a pyrene group, a chrysene group, a fluorene group, a pyrrole group, an imidazole group, a pyrazole group, a thiazole group, an isothiazole group, an oxazole group, an isoxazole group, an oxadiazole group, a triazole group, a pyridine group, a pyrimidine group, a pyrazine group, a pyridazine group, a triazine group, a quinoline group, an isoquinoline group, a quinoxaline group, a quinazoline group, an indole group, an iso-indole group, a benzimidazole group, a benzoxazole group, an isobenzoxazole group, an indazole group, a benzofuran group, a benzothiophene group, an indeno pyridine group, a carbazole group, a carboline group, a dibenzofuran group, a dibenzothiophene group, a dibenzosilole group, and a benzosilolo pyridine group, but they are not limited thereto.

In an embodiment, $Y_{11}$ and $Y_{12}$ in Formula 1 may each independently be selected from a benzene group, a naphthalene group, a phenanthrene group, an anthracene group, a fluorene group, an imidazole group, a pyrazole group, a triazole group, a pyridine group, a pyrimidine group, a pyrazine group, a pyridazine group, a triazine group, a quinoline group, an isoquinoline group, an indole group, an iso-indole group, a benzimidazole group, an indazole group, a benzofuran group, a benzothiophene group, an indenopyridine group, a carbazole group, a carboline group, a dibenzofuran group, a benzofuranopyridine group, a dibenzothiophene group, a benzothiophenopyridine group, a dibenzosilole group, and a benzosilolo pyridine group, but they are not limited thereto.

In an embodiment, $Y_{11}$ and $Y_{12}$ in Formula 1 may each independently be selected from a benzene group, a naphthalene group, a fluorene group, an imidazole group, a pyrazole group, a triazole group, a pyridine group, a pyrimidine group, a pyrazine group, a triazine group, a quinoline group, an isoquinoline group, an indole group, an iso-indole group, a benzimidazole group, an indazole group, an indenopyridine group, a carbazole group, a carboline group, a dibenzofuran group, a benzofuranopyridine group, a dibenzothiophene group, a benzothiophenopyridine group, a dibenzosilole group, and a benzosilolo pyridine group, but they are not limited thereto.

In an embodiment, at least one selected from $Y_{11}$ and $Y_{12}$ in Formula 1 may be selected from a $C_1$-$C_{60}$ heterocyclic group, but is not limited thereto.

In an embodiment, at least one selected from $Y_{11}$ and $Y_{12}$ in Formula 1 may be selected from an imidazole group, a pyrazole group, a triazole group, a pyridine group, a pyrimidine group, a pyrazine group, a triazine group, a quinoline group, an isoquinoline group, an indole group, an iso-indole group, a benzimidazole group, an indazole group, an indenopyridine group, a carbazole group, a carboline group, a dibenzofuran group, a benzofuranopyridine group, a dibenzothiophene group, a benzothiophenopyridine group, a dibenzosilole group, and a benzosilolo pyridine group, but is not limited thereto.

In an embodiment, moieties represented by $Y_{11}$-$Y_{12}$ in Formula 1 may be selected from Formulae 3-1 to 3-29, but they are not limited thereto:

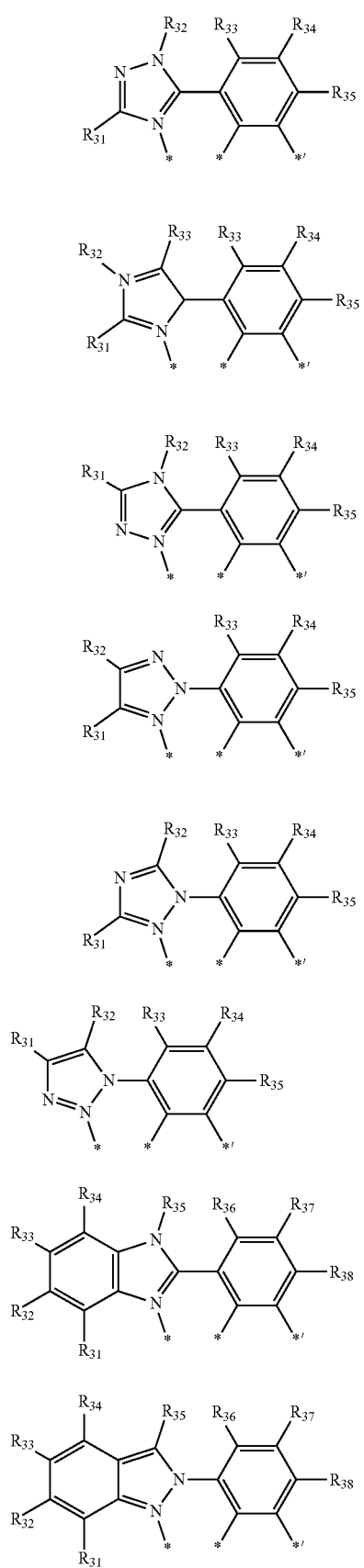
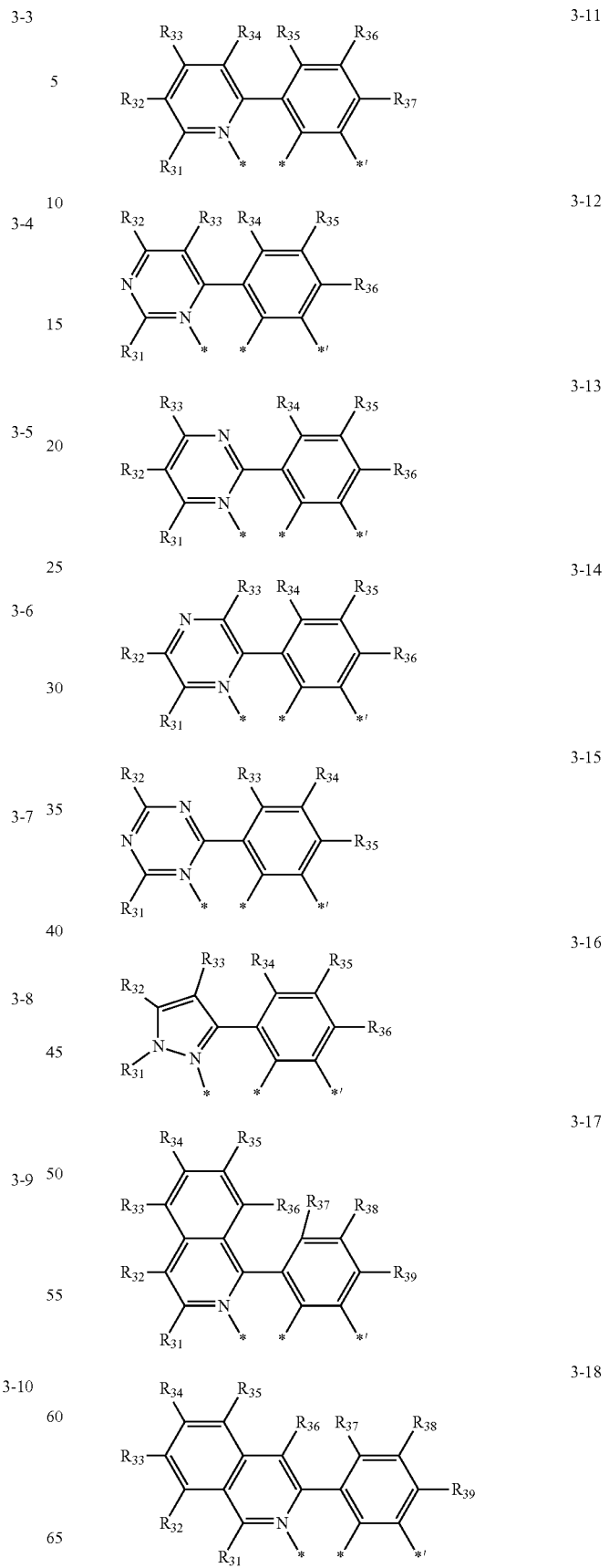

-continued
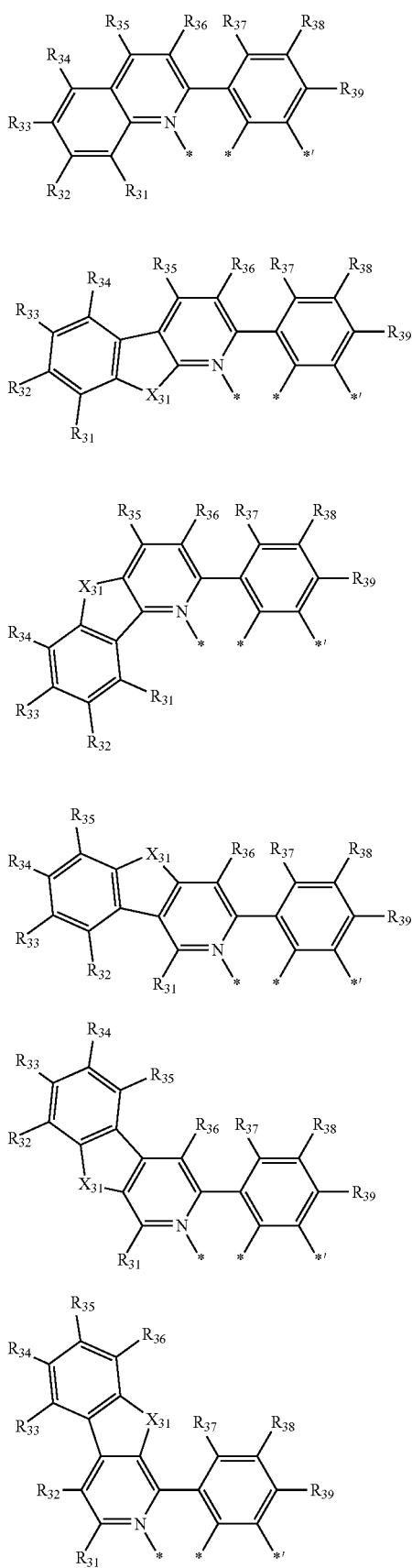
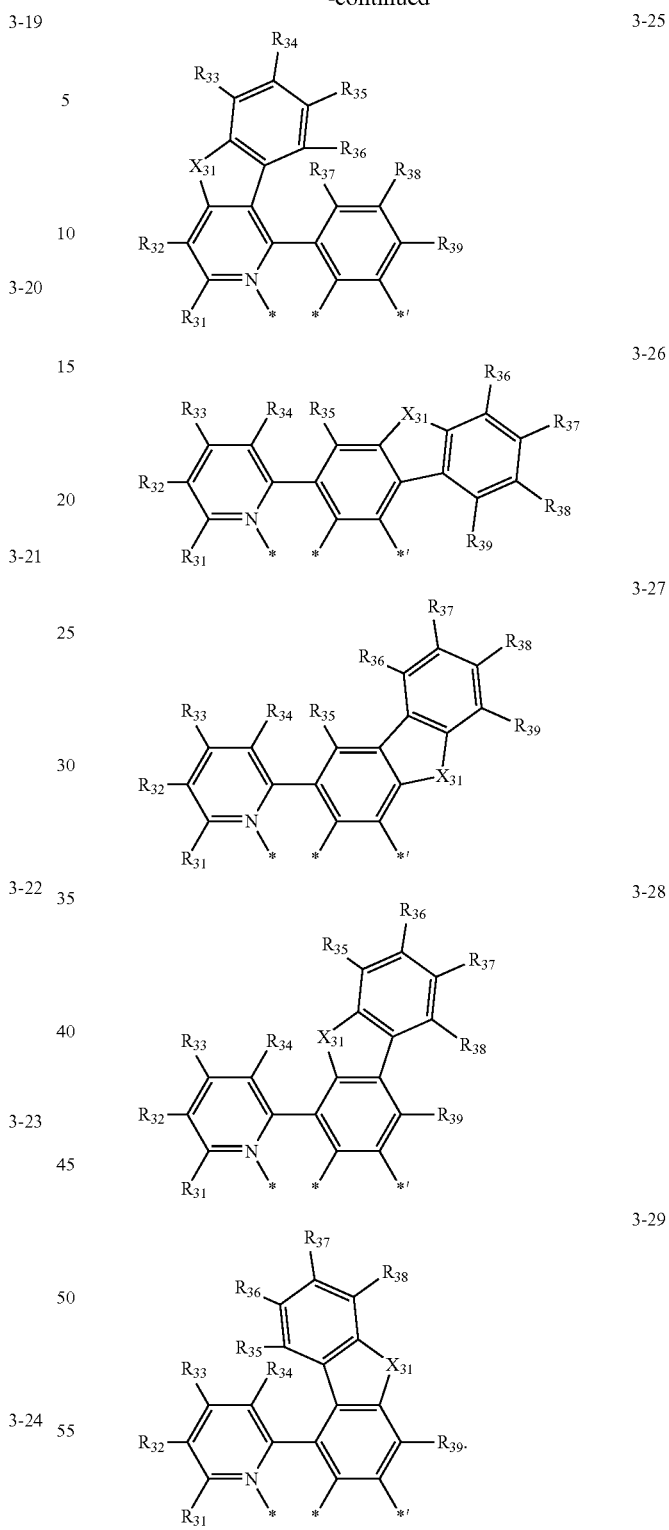
In Formulae 3-1 to 3-29,
$X_{31}$ may be selected from $C(R_{40})(R_{41})$, $N(R_{41})$, O, S, and $Si(R_{40})(R_{41})$;
$R_{31}$ to $R_{41}$ may each independently be selected from hydrogen, deuterium, —F, a cyano group, a methyl group, an ethyl group, an n-propyl group, an iso-propyl group, an n-butyl group, an iso-butyl group, a sec-butyl group, a tert-butyl group, —CFH$_2$, —CF$_2$H, —CF$_3$, and a benzyl group;

a phenyl group, a biphenyl group, a terphenyl group, a naphthyl group, a pyridinyl group, a pyrimidinyl group, a pyridazinyl group, and a triazinyl group;

a phenyl group, a biphenyl group, a terphenyl group, a naphthyl group, a pyridinyl group, a pyrimidinyl group, a pyridazinyl group, and a triazinyl group, each substituted with at least one selected from deuterium, —F, a cyano group, a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, a pyridinyl group, a pyrimidinyl group, a pyridazinyl group, a triazinyl group, —Si(Q$_{21}$)(Q$_{22}$)(Q$_{23}$), —Ge(Q$_{21}$)(Q$_{22}$)(Q$_{23}$), and —N(Q$_{21}$)(Q$_{22}$); and —Si(Q$_{31}$)(Q$_{32}$)(Q$_{33}$), —Ge(Q$_{31}$)(Q$_{32}$)(Q$_{33}$), and —N(Q$_{31}$)(Q$_{32}$);

Q$_{21}$ to Q$_{23}$ and Q$_{31}$ to Q$_{33}$ may each independently be selected from hydrogen, a methyl group, an ethyl group, an n-propyl group, an iso-propyl group, an n-butyl group, a phenyl group, a biphenyl group, and a terphenyl group;

\* indicates a binding site to Pt in Formula 1; and

\*' indicates a binding site to a neighboring nitrogen atom (N).

R$_{11}$ to R$_{24}$ in Formula 1 may each independently be selected from hydrogen, deuterium, —F, —Cl, —Br, —I, a cyano group, a nitro group, an amidino group, a hydrazino group, a hydrazono group, a substituted or unsubstituted C$_1$-C$_{60}$ alkyl group, a substituted or unsubstituted C$_1$-C$_{60}$ alkoxy group, a substituted or unsubstituted C$_1$-C$_{60}$ alkylthio group, a substituted or unsubstituted C$_3$-C$_{10}$ cycloalkyl group, a substituted or unsubstituted C$_1$-C$_{10}$ heterocycloalkyl group, a substituted or unsubstituted C$_6$-C$_{60}$ aryl group, a substituted or unsubstituted C$_1$-C$_{60}$ heteroaryl group, a substituted or unsubstituted C$_6$-C$_{60}$ aryloxy group, a substituted or unsubstituted C$_6$-C$_{60}$ arylthio group, a substituted or unsubstituted monovalent non-aromatic condensed polycyclic group, a substituted or unsubstituted monovalent non-aromatic condensed heteropolycyclic group, —Si(Q$_3$)(Q$_4$)(Q$_5$), Ge(Q$_3$)(Q$_4$)(Q$_5$), —N(Q$_3$)(Q$_4$), —B(Q$_3$)(Q$_4$), —C(=O)(Q$_3$), —S(=O)$_2$(Q$_3$), and —P(=O)(Q$_3$)(Q$_4$);

provided that two neighboring substituents selected from R$_{11}$ to R$_{24}$ may optionally be linked to form a substituted or unsubstituted saturated ring or a substituted or unsubstituted unsaturated ring;

wherein Q$_3$ to Q$_5$ may each independently be selected from hydrogen, deuterium, a C$_1$-C$_{60}$ alkyl group, a C$_6$-C$_{60}$ aryl group, a C$_1$-C$_{60}$ heteroaryl group, a monovalent non-aromatic condensed polycyclic group, a monovalent non-aromatic condensed heteropolycyclic group, a biphenyl group, and a terphenyl group.

For example, R$_{11}$ to R$_{24}$ in Formula 1 may each independently be selected from hydrogen, deuterium, —F, —Cl, —Br, —I, a cyano group, a nitro group, an amidino group, a hydrazino group, a hydrazono group, a C$_1$-C$_{60}$ alkyl group, a C$_1$-C$_{60}$ alkoxy group, and a C$_1$-C$_{60}$ alkylthio group;

a C$_1$-C$_{60}$ alkyl group, a C$_1$-C$_{60}$ alkoxy group, and a C$_1$-C$_{60}$ alkylthio group, each substituted with at least one selected from deuterium, —F, —Cl, —Br, —I, a cyano group, a nitro group, an amidino group, a hydrazino group, a hydrazono group, a C$_3$-C$_{10}$ cycloalkyl group, a C$_1$-C$_{10}$ heterocycloalkyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{31}$)(Q$_{32}$)(Q$_{33}$), —Ge(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$);

a C$_3$-C$_{10}$ cycloalkyl group, a C$_1$-C$_{10}$ heterocycloalkyl group, a C$_6$-C$_{60}$ aryl group, a C$_1$-C$_{60}$ heteroaryl group, a C$_6$-C$_{60}$ aryloxy group, a C$_6$-C$_{60}$ arylthio group, a monovalent non-aromatic condensed polycyclic group, and a monovalent non-aromatic condensed heteropolycyclic group;

a C$_3$-C$_{10}$ cycloalkyl group, a C$_1$-C$_{10}$ heterocycloalkyl group, a C$_6$-C$_{60}$ aryl group, a C$_1$-C$_{60}$ heteroaryl group, a C$_6$-C$_{60}$ aryloxy group, a C$_6$-C$_{60}$ arylthio group, a monovalent non-aromatic condensed polycyclic group, and a monovalent non-aromatic condensed heteropolycyclic group, each substituted with at least one selected from deuterium, —F, —Cl, —Br, —I, a cyano group, a nitro group, an amidino group, a hydrazino group, a hydrazono group, a C$_1$-C$_{60}$ alkyl group, a C$_1$-C$_{60}$ alkoxy group, a C$_1$-C$_{60}$ alkylthio group, C$_3$-C$_{10}$ cycloalkyl group, a C$_1$-C$_{10}$ heterocycloalkyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{31}$)(Q$_{32}$)(Q$_{33}$), —Ge(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$); and —Si(Q$_3$)(Q$_4$)(Q$_5$), —Ge(Q$_3$)(Q$_4$)(Q$_5$), —N(Q$_3$)(Q$_4$), —B(Q$_3$)(Q$_4$), —C(=O)(Q$_3$), —S(=O)$_2$(Q$_3$), and —P(=O)(Q$_3$)(Q$_4$), wherein Q$_3$ to Q$_5$ and Q$_{31}$ to Q$_{33}$ may each independently be selected from hydrogen, deuterium, C$_1$-C$_{60}$ alkyl group, a C$_6$-C$_{60}$ aryl group, a C$_1$-C$_{60}$ heteroaryl group, a monovalent non-aromatic condensed polycyclic group, a monovalent non-aromatic condensed heteropolycyclic group, a biphenyl group, and a terphenyl group, but they are not limited thereto.

In an embodiment, R$_{11}$ to R$_{24}$ in Formula 1 may each independently be selected from hydrogen, deuterium, —F, a cyano group, a methyl group, an ethyl group, an n-propyl group, an iso-propyl group, an n-butyl group, an iso-butyl group, a sec-butyl group, a tert-butyl group, a methoxy group, an ethoxy group, an n-propoxy group, an iso-propoxy group, an n-butoxy group, an iso-butoxy group, a sec-butoxy group, and a tert-butoxy group;

a methyl group, an ethyl group, an n-propyl group, an iso-propyl group, an n-butyl group, an iso-butyl group, a sec-butyl group, a tert-butyl group, a methoxy group, an ethoxy group, an n-propoxy group, an iso-propoxy group, an n-butoxy group, an iso-butoxy group, a sec-butoxy group, and a tert-butoxy group, each substituted with at least one selected from deuterium, —F, a cyano group, a cyclopentyl group, a cyclohexyl group, a phenyl group, a biphenyl group, a terphenyl group, a naphthyl group, a phenyloxy group, a phenylthio group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, a dibenzothiophenyl group, —Si(Q$_{31}$)(Q$_{32}$)(Q$_{33}$), —Ge(Q$_{31}$)(Q$_{32}$)(Q$_{33}$), and —N(Q$_{31}$)(Q$_{32}$);

a cyclopentyl group, a cyclohexyl group, a phenyl group, a biphenyl group, a terphenyl group, a naphthyl group, a phenyloxy group, a phenylthio group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, and a dibenzothiophenyl group;

a cyclopentyl group, a cyclohexyl group, a phenyl group, a biphenyl group, a terphenyl group, a naphthyl group, a phenyloxy group, a phenylthio group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, and a dibenzothiophenyl group, each substituted with at least one selected from deuterium, —F, a cyano group, a methyl group, an ethyl group, an n-propyl group, an iso-propyl group, an n-butyl group, an iso-butyl group, a sec-butyl group, a tert-butyl group, a methoxy group, an ethoxy group, an n-propoxy group, an iso-propoxy group, an n-butoxy group, an iso-butoxy group, a sec-butoxy group, a tert-butoxy group, a cyclopentyl group, a cyclohexyl group, a phenyl group, a biphenyl group, a terphenyl group, a naphthyl group, a phenyloxy group, a phenylthio group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, a dibenzothiophenyl group, —Si($Q_{31}$)($Q_{32}$)($Q_{33}$), —Ge($Q_{31}$)($Q_{32}$)($Q_{33}$), and —N($Q_{31}$)($Q_{32}$); and —Si($Q_3$)($Q_4$)($Q_5$), —Ge($Q_3$)($Q_4$)($Q_5$), and —N($Q_3$)($Q_4$), wherein $Q_3$ to $Q_5$ and $Q_{31}$ to $Q_{33}$ may each independently be selected from hydrogen, a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, and a dibenzothiophenyl group, but they are not limited thereto.

In an embodiment, $R_{11}$ to $R_{24}$ in Formula 1 may each independently be selected from hydrogen, deuterium, —F, a cyano group, a methyl group, an ethyl group, an n-propyl group, an iso-propyl group, an n-butyl group, an iso-butyl group, a sec-butyl group, a tert-butyl group, —CFH$_2$, —CF$_2$H, —CF$_3$, and a benzyl group;

a phenyl group, a biphenyl group, a terphenyl group, a naphthyl group, a pyridinyl group, a pyrimidinyl group, a pyridazinyl group, and a triazinyl group;

a phenyl group, a biphenyl group, a terphenyl group, a naphthyl group, a pyridinyl group, a pyrimidinyl group, a pyridazinyl group, and a triazinyl group, each substituted with at least one selected from deuterium, —F, a cyano group, a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, a pyridinyl group, a pyrimidinyl group, a pyridazinyl group, a triazinyl group, —Si($Q_{31}$)($Q_{32}$)($Q_{33}$), —Ge($Q_{31}$)($Q_{32}$)($Q_{33}$), and —N($Q_{31}$)($Q_{32}$); and —Si($Q_3$)($Q_4$)($Q_5$), —Ge($Q_3$)($Q_4$)($Q_5$), and —N($Q_3$)($Q_4$), wherein $Q_3$ to $Q_5$ and $Q_{31}$ to $Q_{33}$ may each independently be selected from hydrogen, a methyl group, an ethyl group, an n-propyl group, an iso-propyl group, an n-butyl group, a phenyl group, a biphenyl group, and a terphenyl group, but they are not limited thereto.

In an embodiment, the organometallic compound represented by Formula 1 may be represented by one of Formulae 1-1 and 1-2, but is not limited thereto:

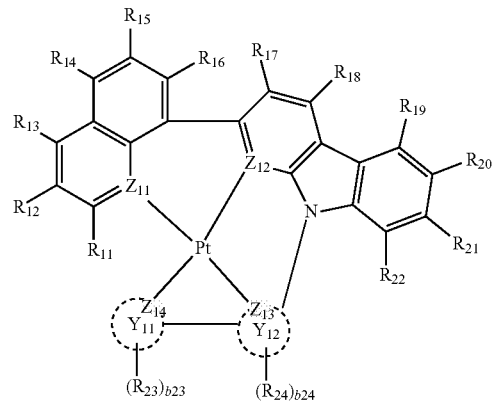

Formula 1-1

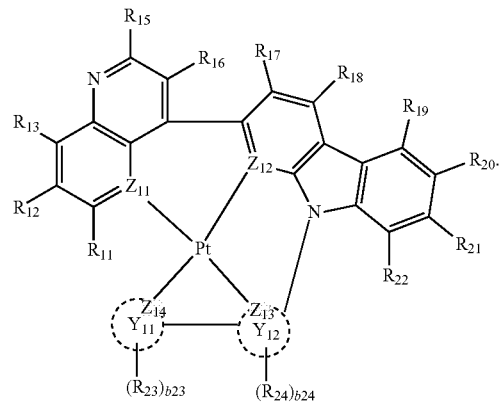

Formula 1-2

In Formulae 1-1 and 1-2, $Z_{11}$ to $Z_{14}$, $Y_{11}$, $Y_{12}$, $R_{11}$ to $R_{24}$, b23, and b24 are the same as described in connection with Formula 1.

For example, moieties represented by $Y_{11}$ and $Y_{12}$ in Formulae 1-1 and 1-2 may be selected from groups represented by Formulae 3-1 to 3-29, but they are not limited thereto.

In an embodiment, the organometallic compound represented by Formula 1 may be represented by one of Formulae 1-11 and 1-12, but is not limited thereto:

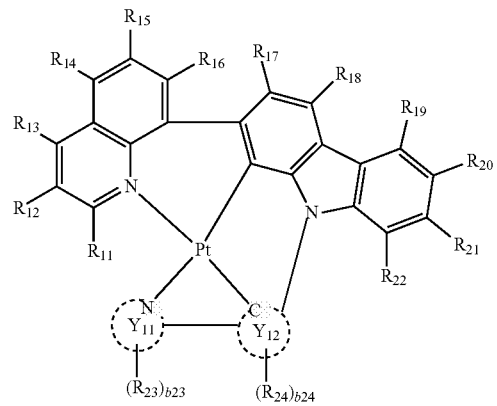

Formula 1-11

Formula 1-12

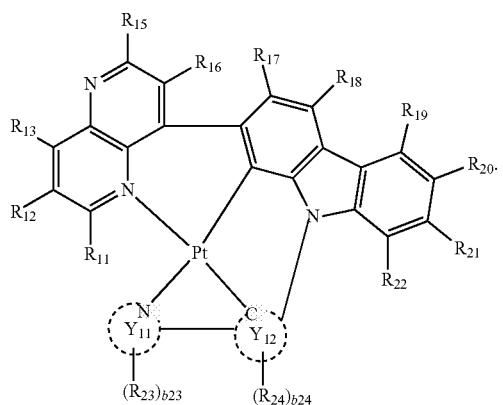

In Formulae 1-11 and 1-12, $Y_{11}$, $Y_{12}$, $R_{11}$ to $R_{24}$, b23, and b24 are the same as described in connection with Formula 1.

For example, moieties represented by $Y_{11}$ and $Y_{12}$ in Formulae 1-11 and 1-12 may be selected from groups represented by Formulae 3-1 to 3-29, but they are not limited thereto.

In an embodiment, the organometallic compound represented by Formula 1 may be selected from Compounds 1 to 45, but is not limited thereto:

1

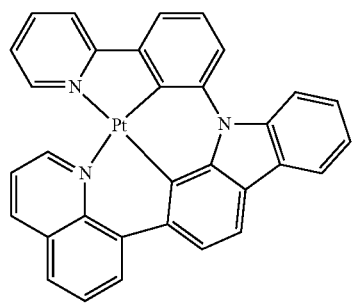

2

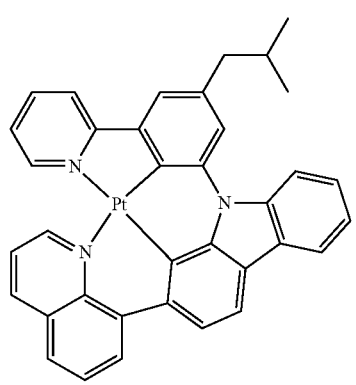

3

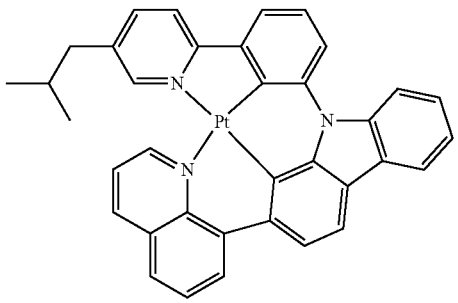

4

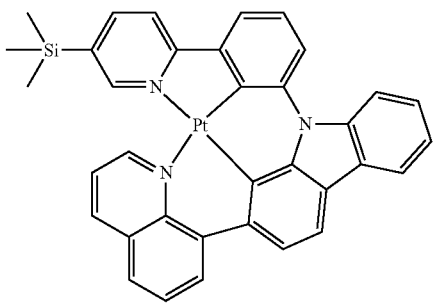

5

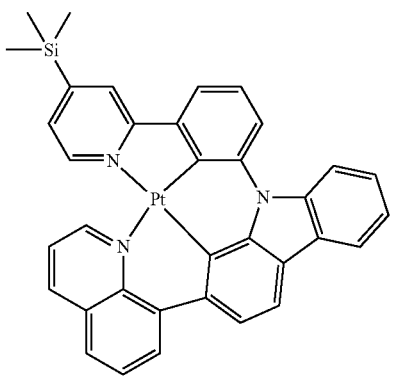

6

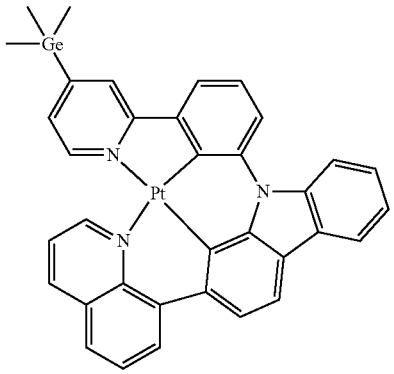

7
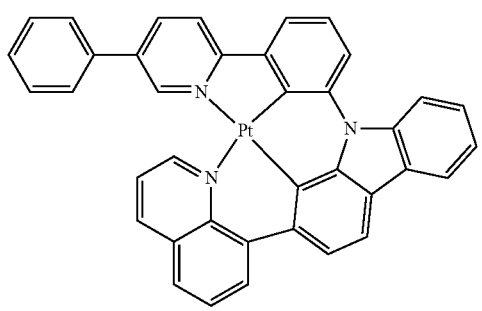
8
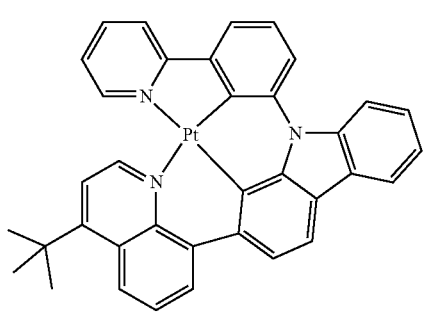
9
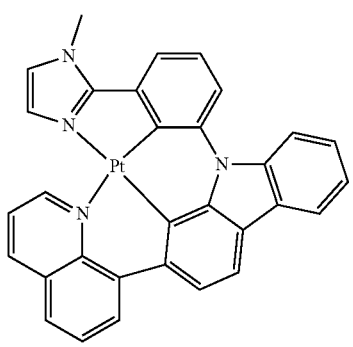
10
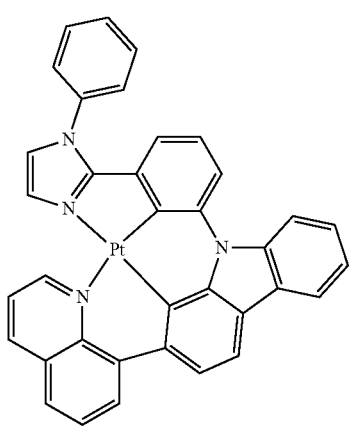
11
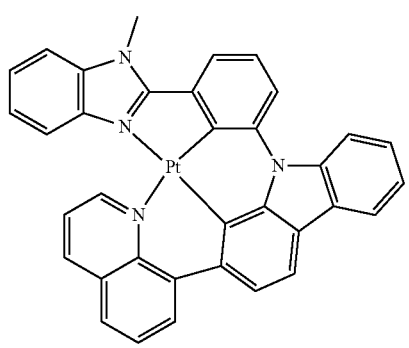
12
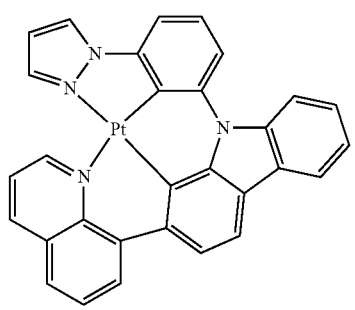
13
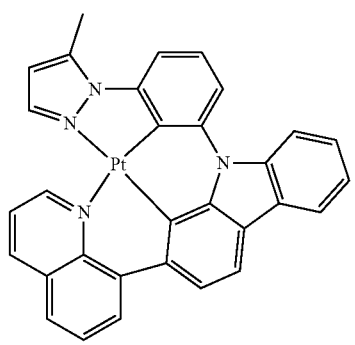
14
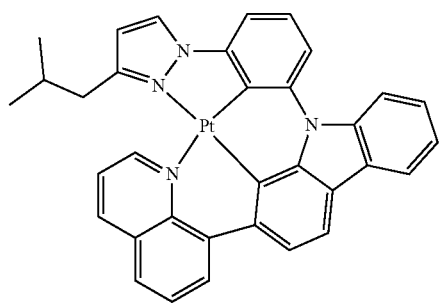

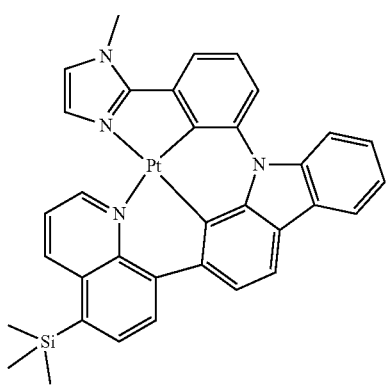
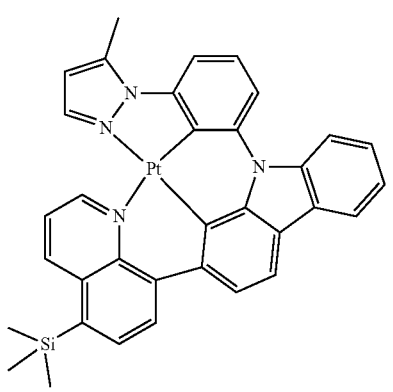
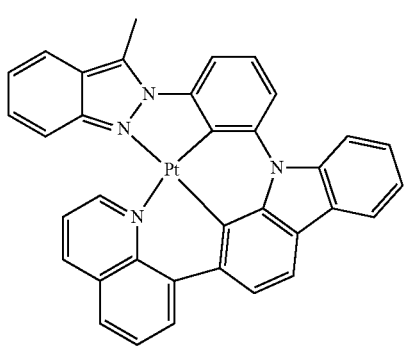
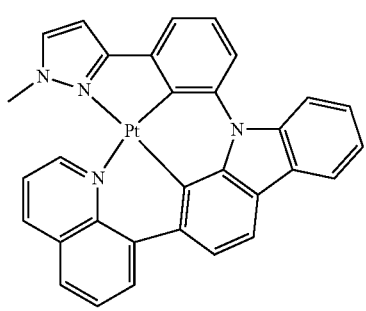
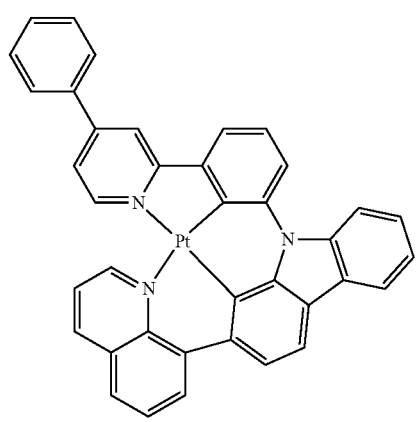
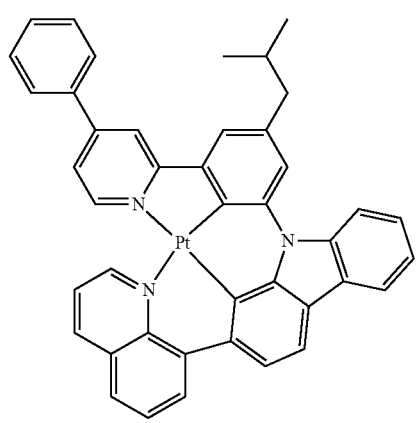
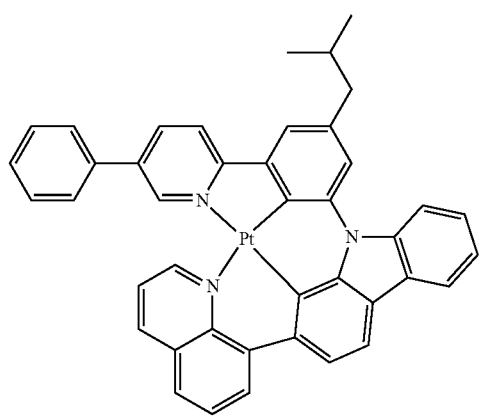

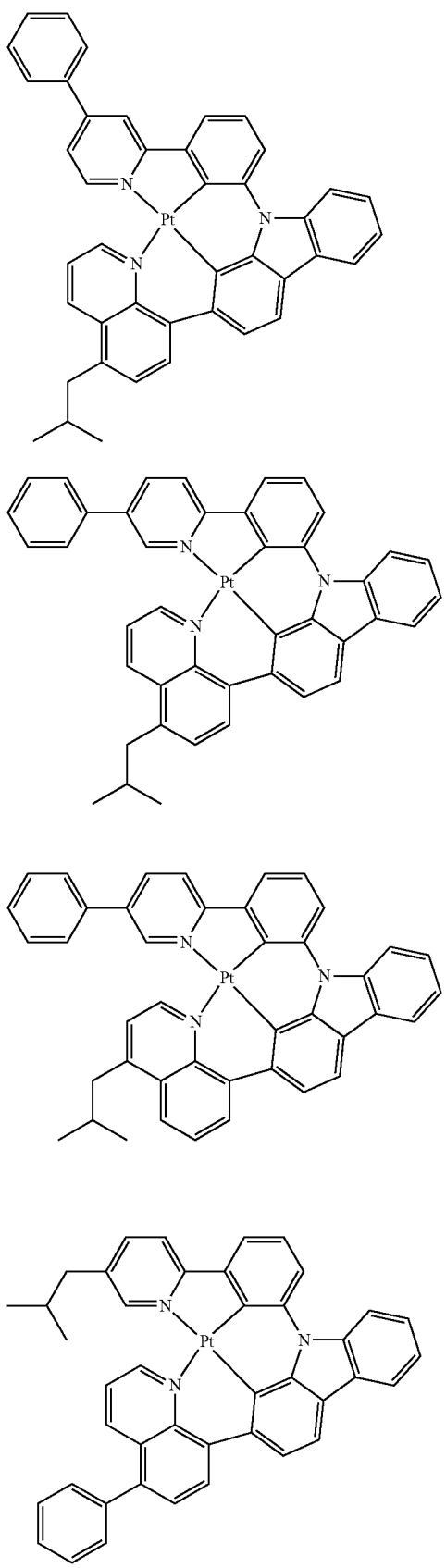
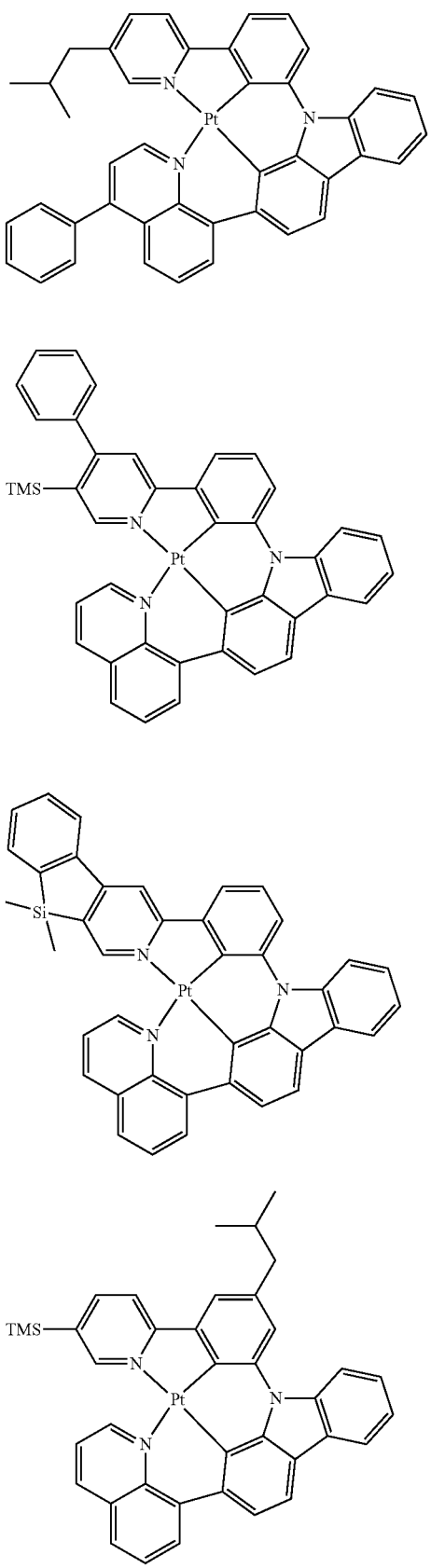

30
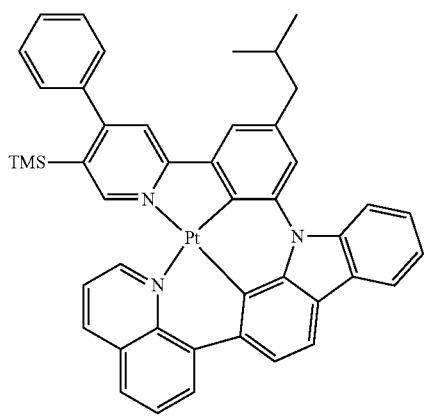
31
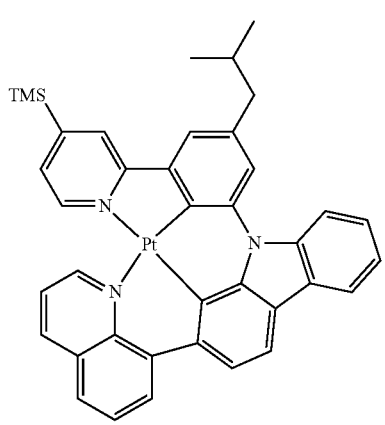
32
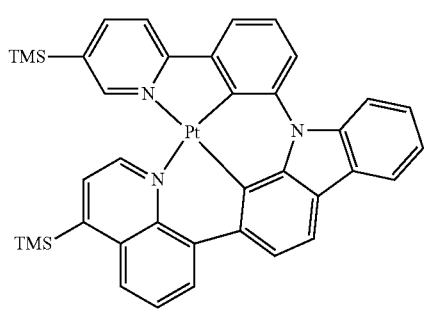
33
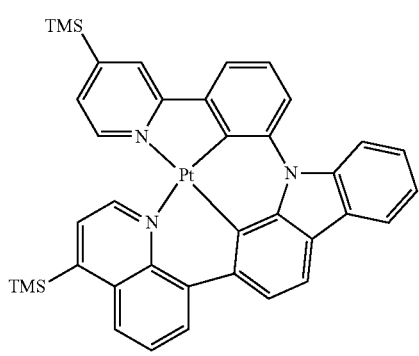
34
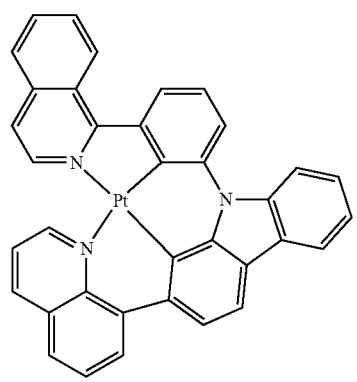
35
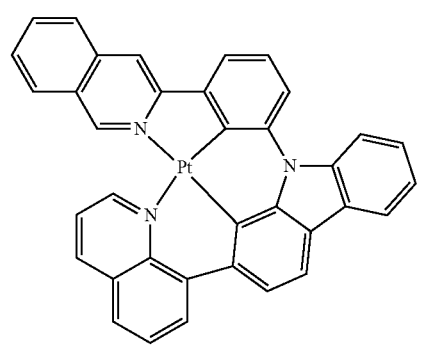
36
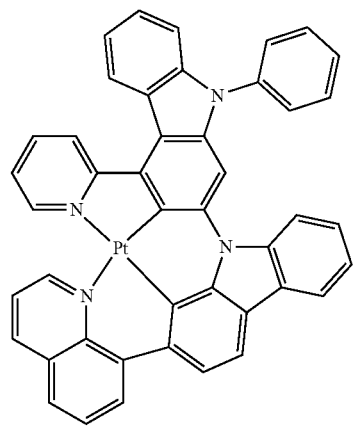
37
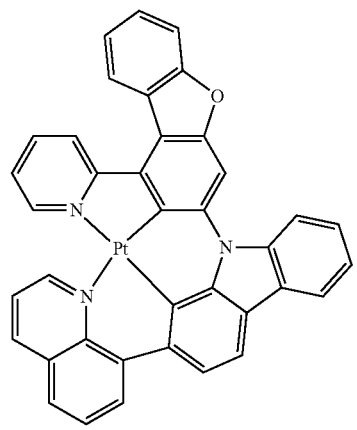

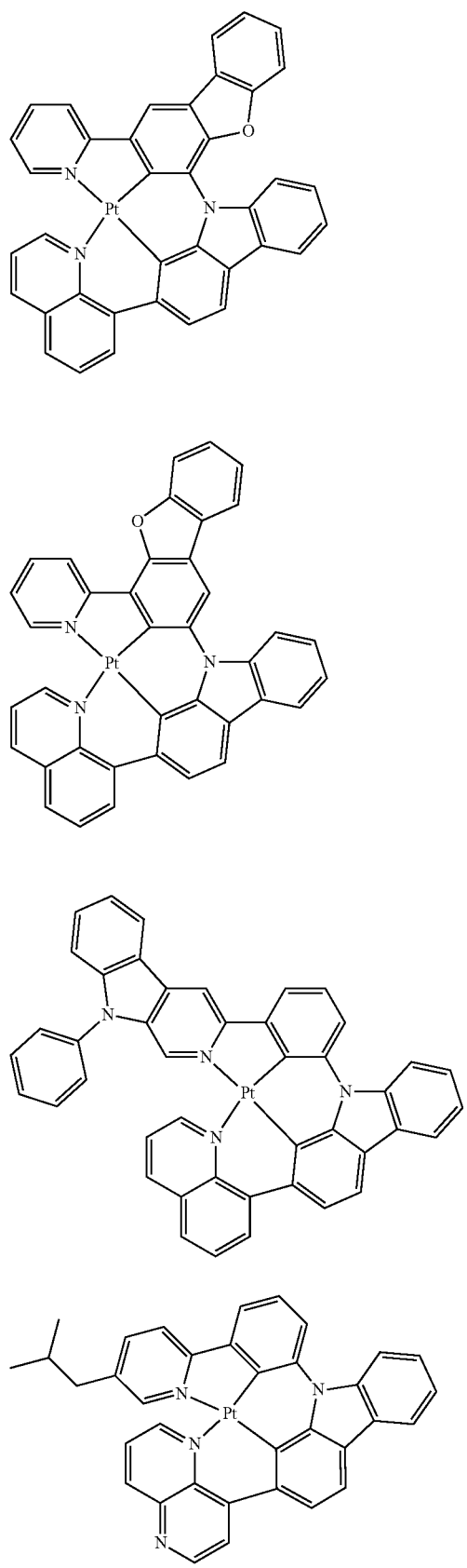
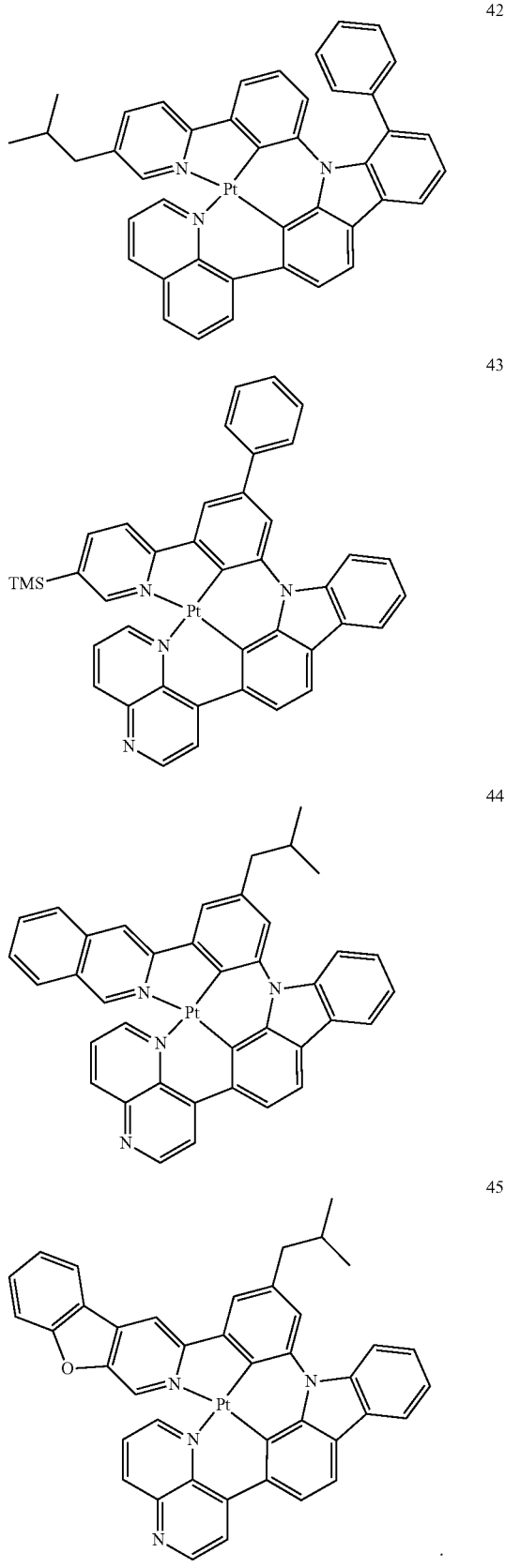

Regarding Compounds 1 to 45,

TMS refers to a trimethylsilyl group ($Si(CH_3)_3$).

The organometallic compound may have a maximum emission wavelength of about 600 nanometers (nm) to about 750 nm, for example, about 610 nm to about 670 nm. While not wishing to be bound by theory, it is understood that when the maximum emission wavelength thereof is within these ranges, an organic light-emitting device manufactured by using the organometallic compound may emit red light.

The organometallic compound represented by Formula 1, as shown in Formula 1', necessarily includes two 6-membered condensed cyclic structures, and due to the inclusion thereof, its thermal stability may be improved. Also, the inclusion of two 6-membered condensed cyclic structures in the organometallic compound represented by Formula 1 as shown in Formula 1' contributes to an improvement in planarity of the organometallic compound, leading to a higher charge mobility. Accordingly, an organic light-emitting device including the organometallic compound may have low driving voltage, high efficiency and long lifespan characteristics.

Formula 1'

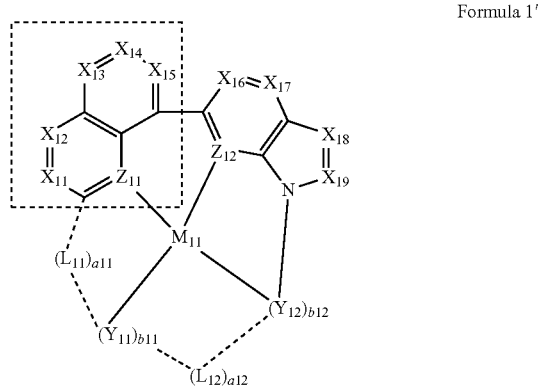

For example, the highest occupied molecular orbital (HOMO), the lowest unoccupied molecular orbital (LUMO), and $T_1$ energy levels of the organometallic compound were simulated by using Gaussian, and the simulation results are shown in Table 1 below:

TABLE 1

| Compound No. | HOMO (eV) | LUMO (eV) | $T_1$ (eV) |
|---|---|---|---|
| 1 | −4.622 | −2.094 | 1.862 |
| 2 | −4.606 | −2.084 | 1.860 |
| 3 | −4.585 | −2.065 | 1.857 |
| 4 | −4.598 | −2.079 | 1.854 |
| 5 | −4.581 | −2.059 | 1.858 |
| 7 | −4.616 | −2.089 | 1.861 |
| 9 | −4.507 | −1.949 | 1.872 |
| 13 | −4.630 | −2.053 | 1.898 |
| 26 | −4.580 | −2.044 | 1.868 |
| 27 | −4.564 | −2.069 | 1.834 |
| 28 | −4.583 | −2.065 | 1.854 |
| 30 | −4.566 | −2.049 | 1.856 |

Synthesis methods of the organometallic compound represented by Formula 1 may be understood by one of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes:

a first electrode;

a second electrode; and an organic layer disposed between the first electrode and the second electrode, wherein the organic layer includes an emission layer and the organometallic compound represented by Formula 1.

The organic light-emitting device may have, due to the inclusion of an organic layer containing the organometallic compound represented by Formula 1, high efficiency, a long lifespan, and a high color purity.

The organometallic compound of Formula 1 may be used between a pair of electrodes of an organic light-emitting device. For example, the organometallic compound represented by Formula 1 may be included in the emission layer. The organometallic compound may act as a dopant and in this case, the emission layer may further include a host. The emission layer may emit red light, green light, or blue light.

The expression that "(an organic layer) includes an organometallic compound" as used herein may include an embodiment in which "(an organic layer) includes an identical organometallic compound represented by Formula 1 and an embodiment in which (an organic layer) includes two or more different organometallic compounds represented by Formula 1.

For example, the organic layer may include, as the organometallic compound, only Compound 1. In this regard, Compound 1 may be included in an emission layer of the organic light-emitting device. In some embodiments, the organic layer may include, as the organometallic compound, Compound 1 and Compound 2. In this regard, Compound 1 and Compound 2 may be included in an identical layer (for example, Compound 1 and Compound 2 all may be included in an emission layer).

The first electrode may be an anode, which is a hole injection electrode, and the second electrode may be a cathode, which is an electron injection electrode, or the first electrode may be a cathode, which is an electron injection electrode, or the second electrode may be an anode, which is a hole injection electrode.

For example, the first electrode may be an anode, and the second electrode may be a cathode, and the organic layer may include:

i) a hole transport region that is disposed between the first electrode and the emission layer, wherein the hole transport region includes at least one selected from a hole injection layer, a hole transport layer, and an electron blocking layer, and ii) an electron transport region that is disposed between the emission layer and the second electrode, wherein the electron transport region includes at least one selected from a hole blocking layer, an electron transport layer, and an electron injection layer.

The term "organic layer" as used herein refers to a single layer and/or a plurality of layers between the first electrode and the second electrode of the organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode may be, for example, indium tin oxide (ITO), indium zinc oxide (IZO), tin oxide ($SnO_2$), and zinc oxide (ZnO). In some embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode.

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

A hole injection layer may be formed on the first electrode 11 by using one or more suitable methods selected from vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (A/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80'C to about 200'C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, R-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrene sulfonate) (PEDOT/PSS), polyaniline/camphor sulfonic acid (Pani/CSA), polyaniline/poly(4-styrene sulfonate) (Pani/PSS), a compound represented by Formula 201 below, and a compound represented by Formula 202 below:

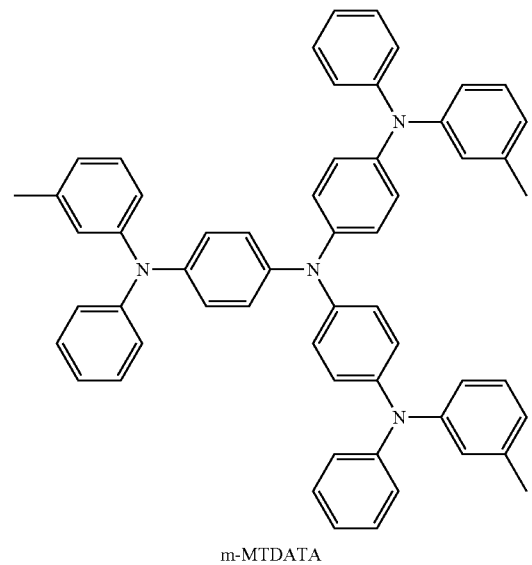

m-MTDATA

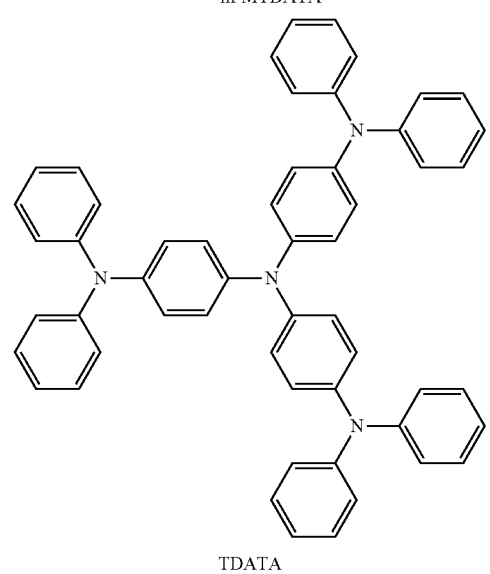

TDATA

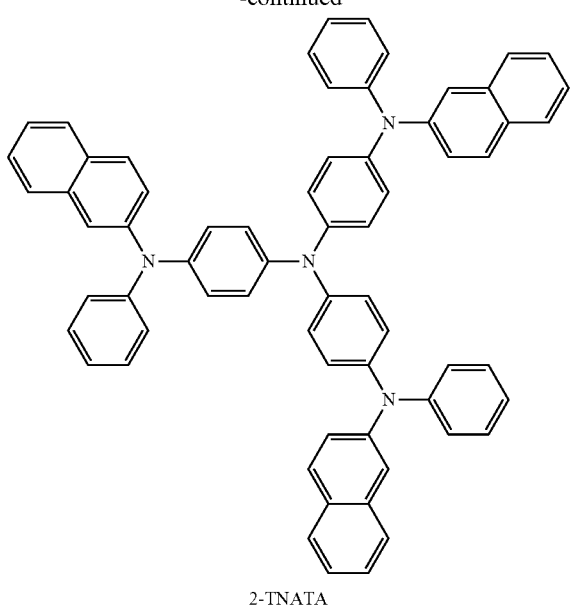
2-TNATA
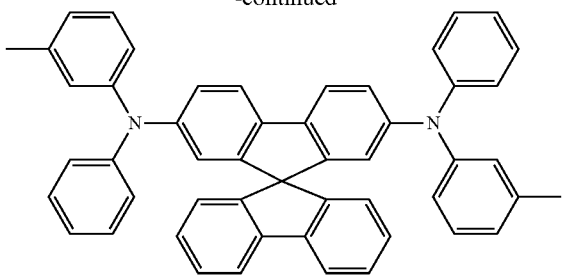
Spiro-TPD
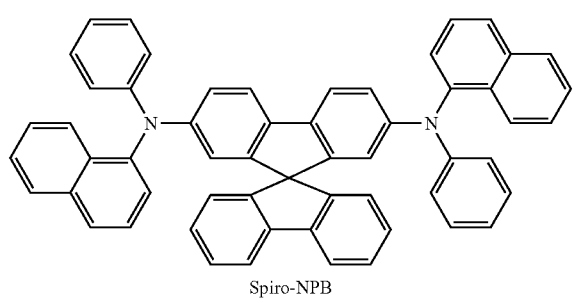
Spiro-NPB
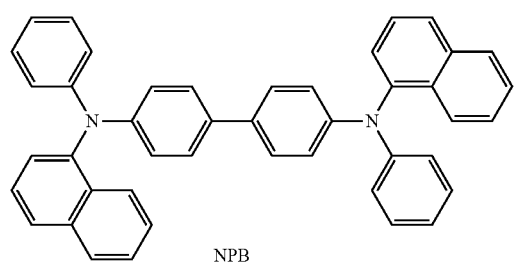
NPB
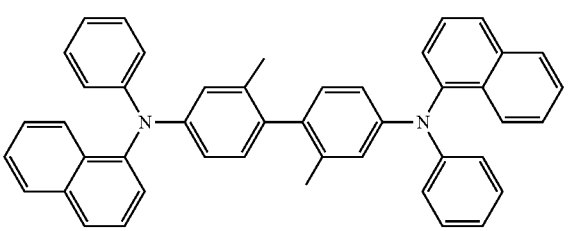
methylated NPB
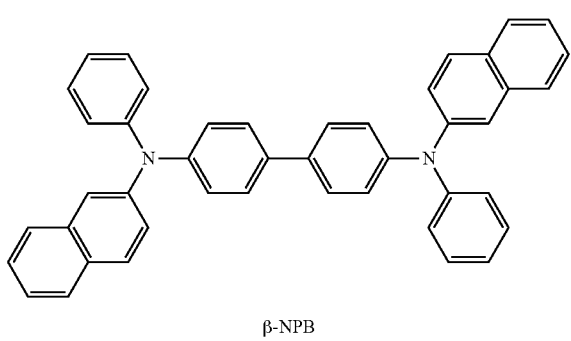
β-NPB
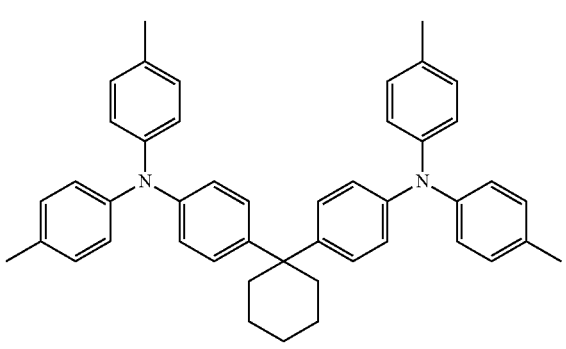
TAPC
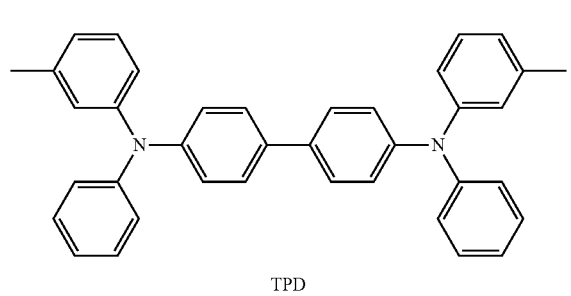
TPD
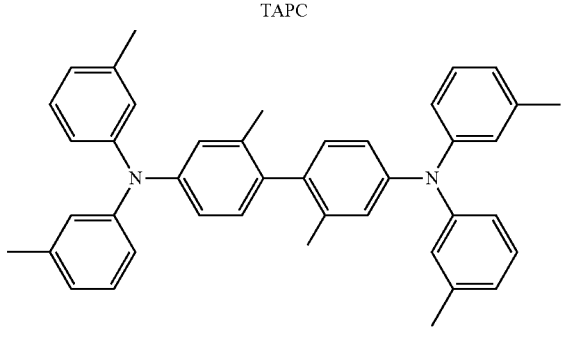
HMTPD Formula 201

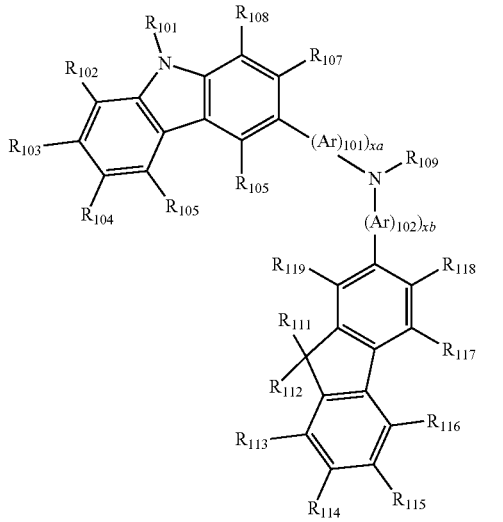

Formula 202

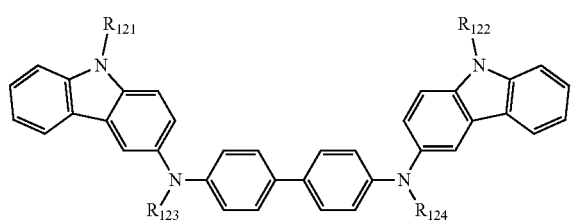

$Ar_{101}$ and $Ar_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or 0, 1, or 2. For example, xa is 1 and xb is 0, but xa and xb are not limited thereto.

$R_{101}$ to $R_{108}$, $R_{111}$ to $R_{119}$, and $R_{121}$ to $R_{124}$ in Formulae 201 and 202 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and a $C_1$-$C_{10}$ alkoxy group, but they are not limited thereto.

$R_{109}$ in Formula 201 may be selected from:

a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but is not limited thereto:

Formula 201A $R_{101}$, $R_{111}$, $R_{112}$, and $R_{109}$ in Formula 201A may be understood by referring to the description provided herein.
For example, the compound represented by Formula 201, and the compound represented by Formula 202 may include compounds HT1 to HT20 illustrated below, but are not limited thereto.
HT1
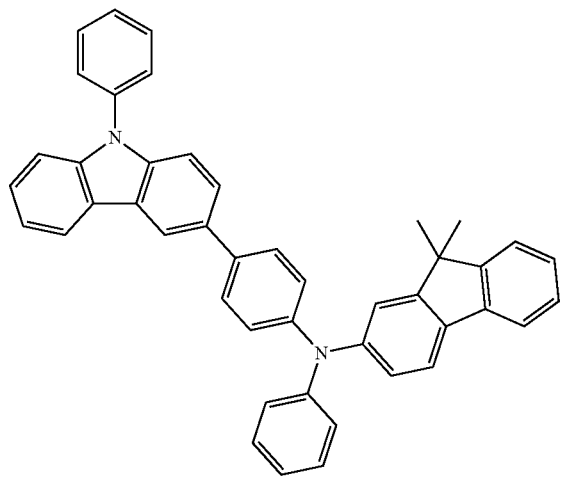
HT2
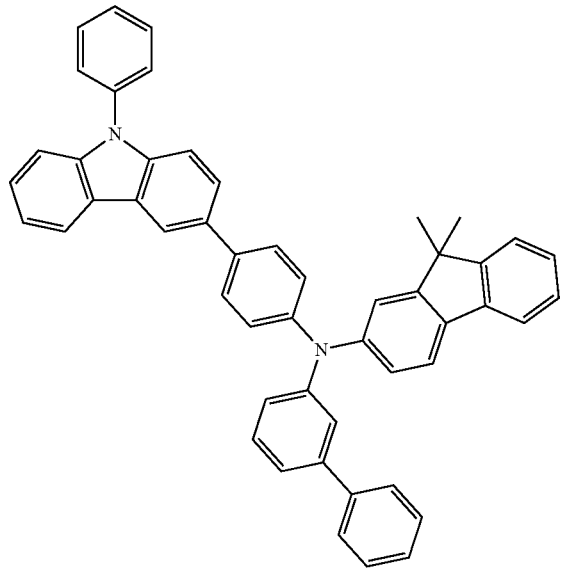
HT3
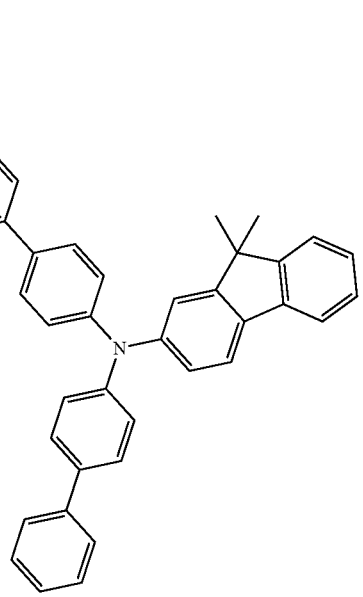
HT4
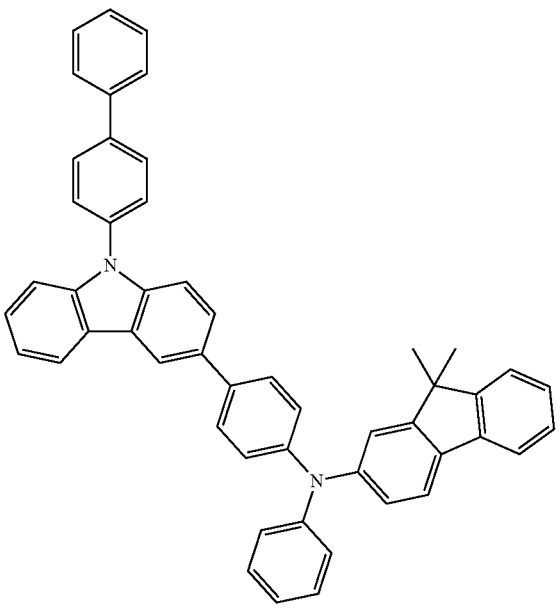

HT5
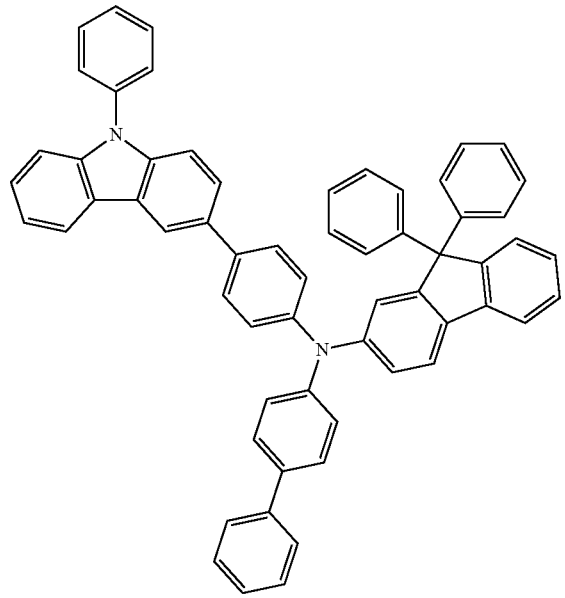
HT6
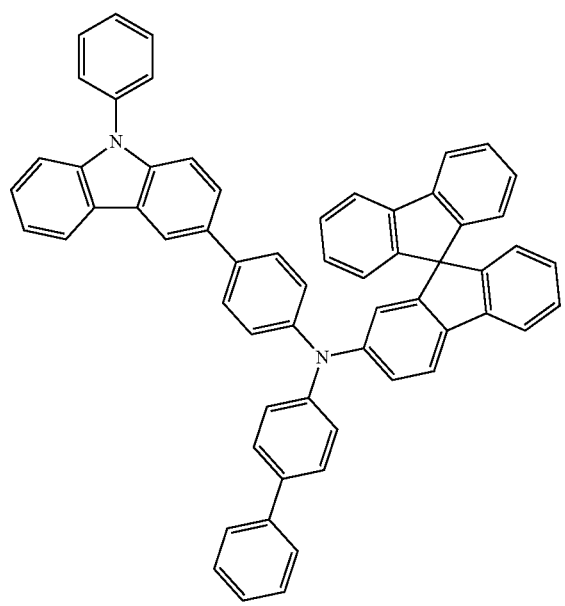
HT7
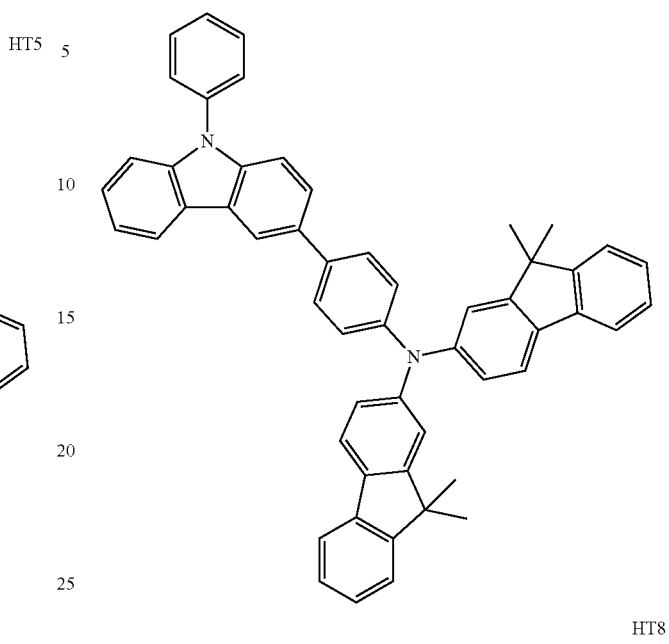
HT8
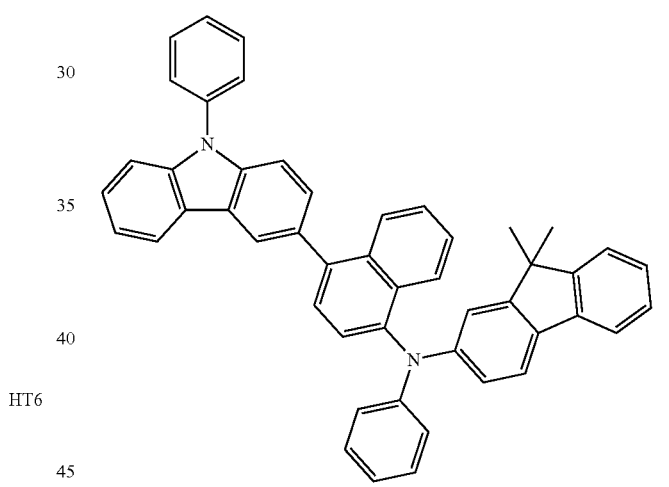
HT9
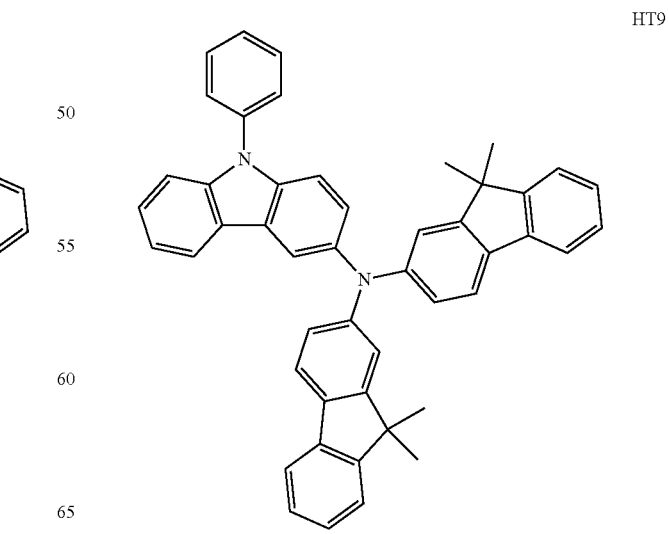

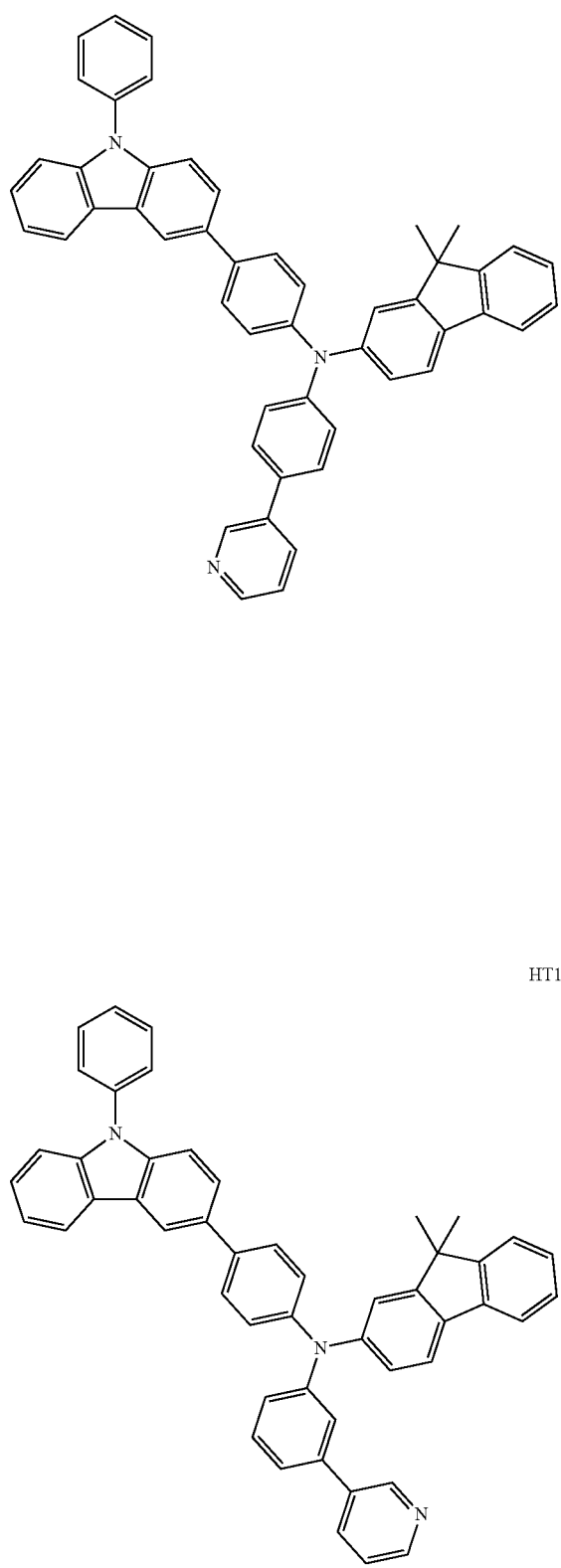
HT10
HT11
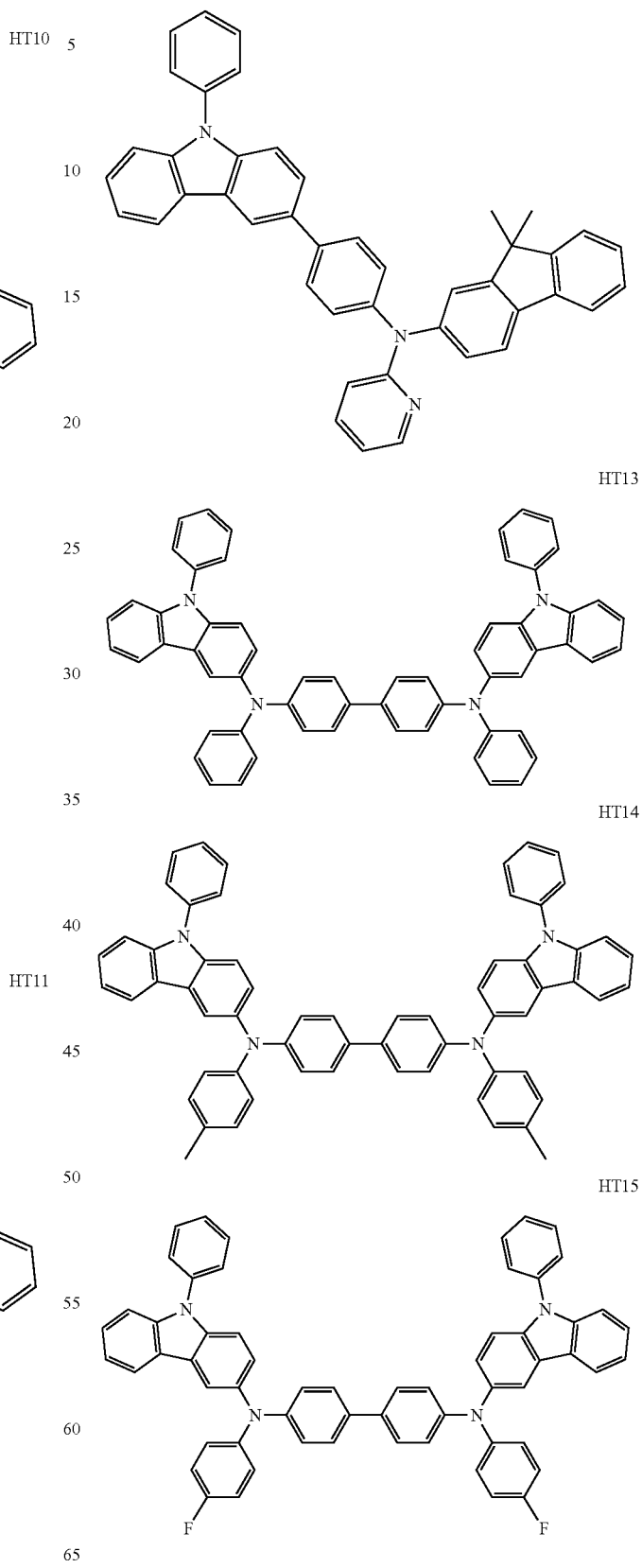
HT12
HT13
HT14
HT15

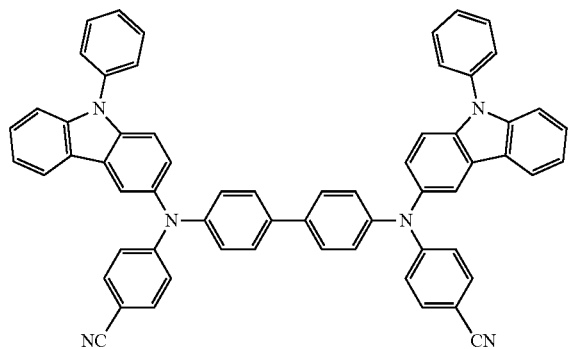

HT16

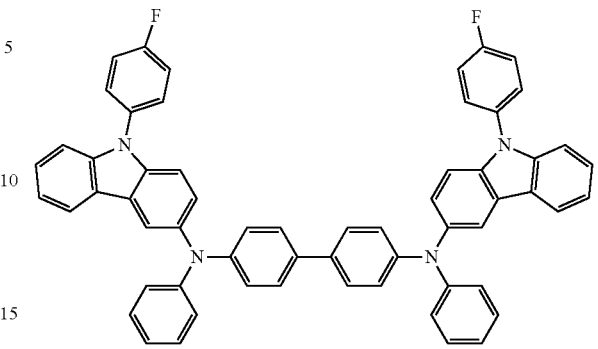

HT20

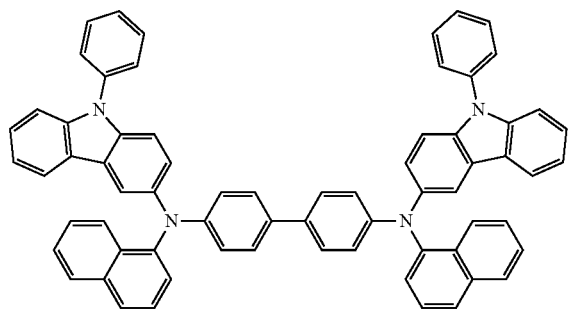

HT17

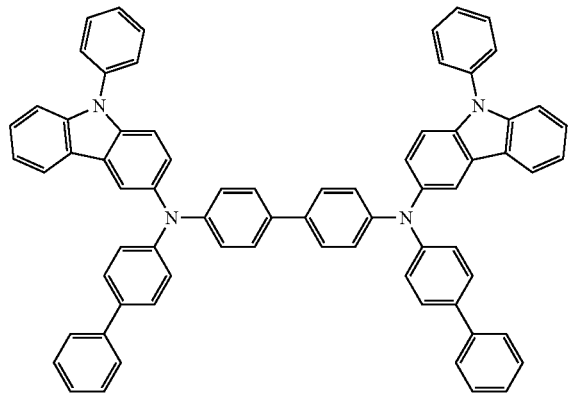

HT18

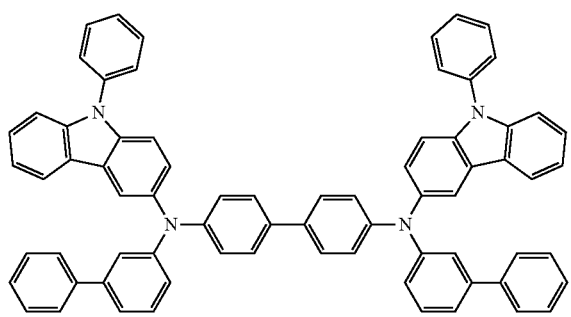

HT19

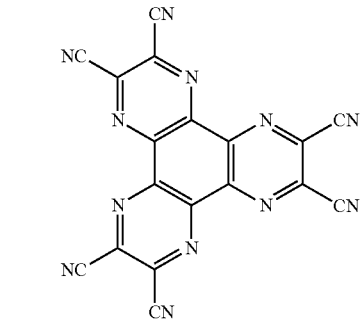

Compound HT-D1

A thickness of the hole transport region may be in a range of about 100 Angstroms (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or Compound HT-D2 below, but are not limited thereto.

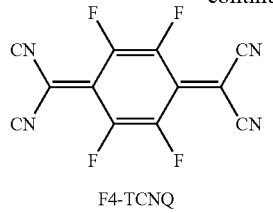

F4-TCNQ

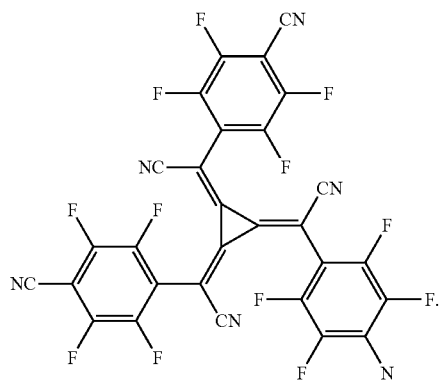

Compound HT-D2

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The emission layer may include a host and a dopant.

The host may include at least one selected from CBP, CDBP, TCP, and mCP:

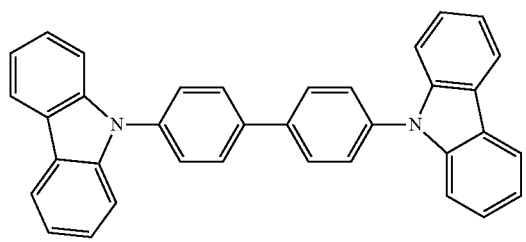

CBP

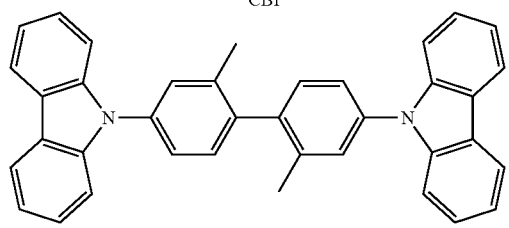

CDBP

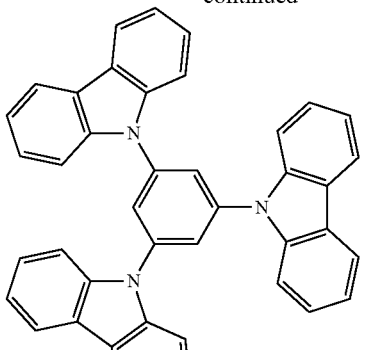

TCP

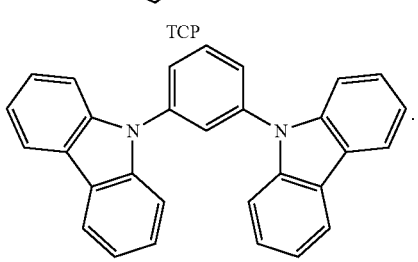

mCP

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

The emission layer may include, as a dopant, the organometallic compound represented by Formula 1.

When the emission layer includes a host and a dopant, an amount of the dopant may be in a range of about 0.01 to about 20 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but may also include other materials.

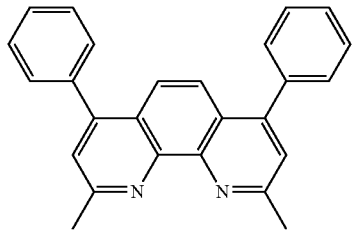

BCP

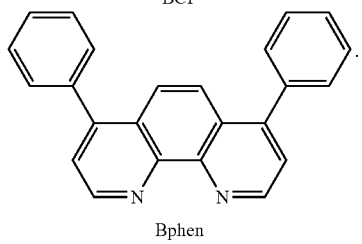

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have improved hole blocking ability without a substantial increase in driving voltage.

The electron transport layer may further include at least one selected from BCP, Bphen, Alq$_3$, BAlq, TAZ, and NTAZ.

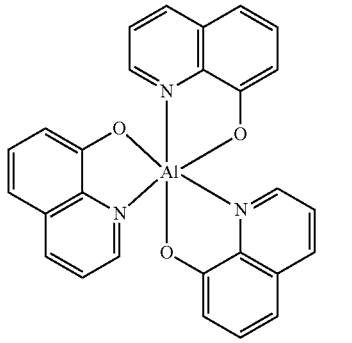

Alq$_3$

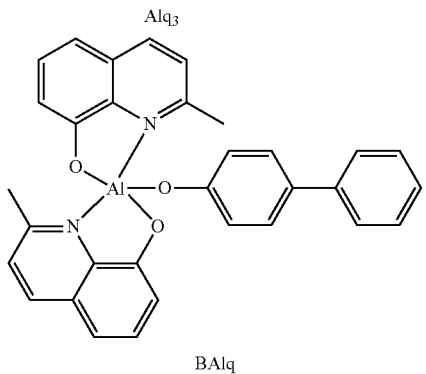

BAlq

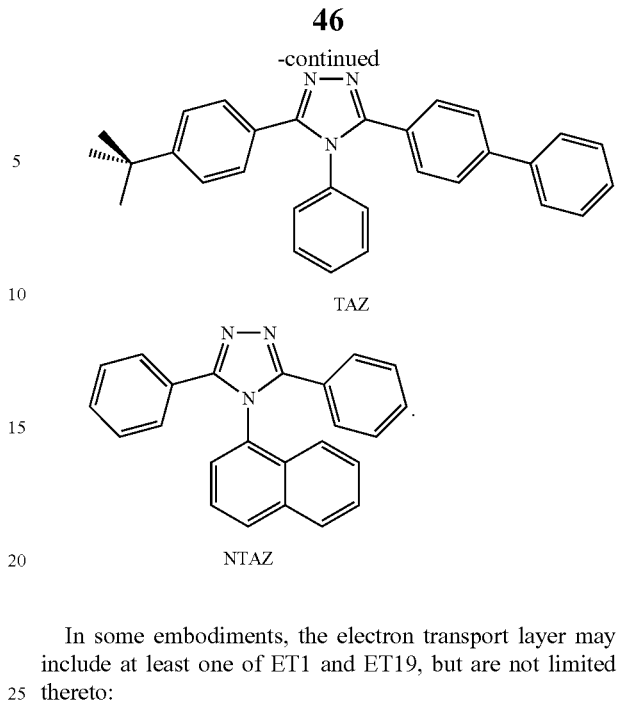

TAZ

NTAZ

In some embodiments, the electron transport layer may include at least one of ET1 and ET19, but are not limited thereto:

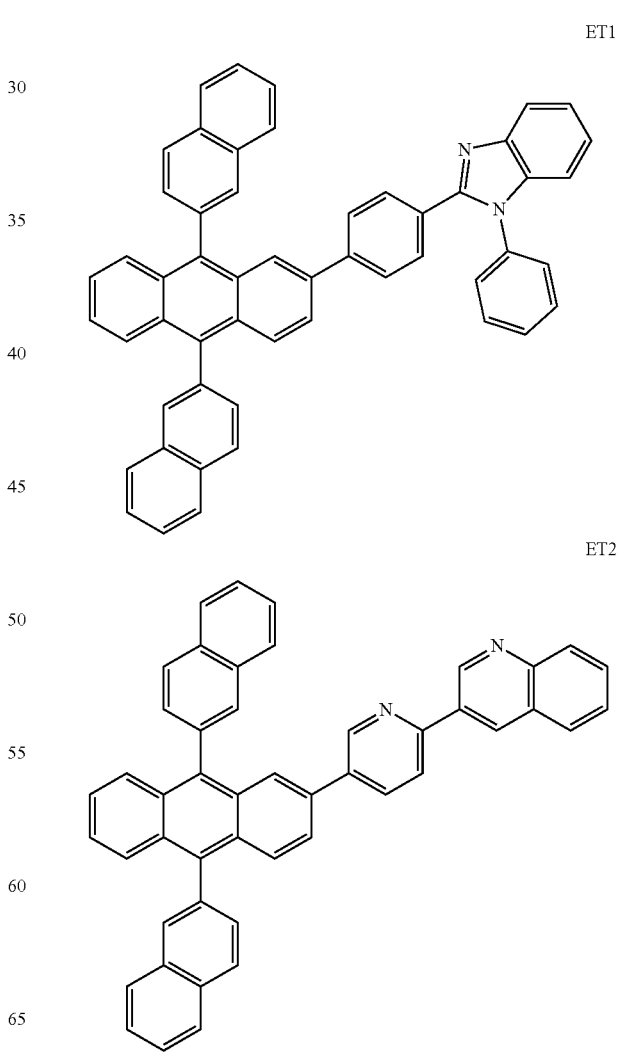

ET1

ET2

ET3
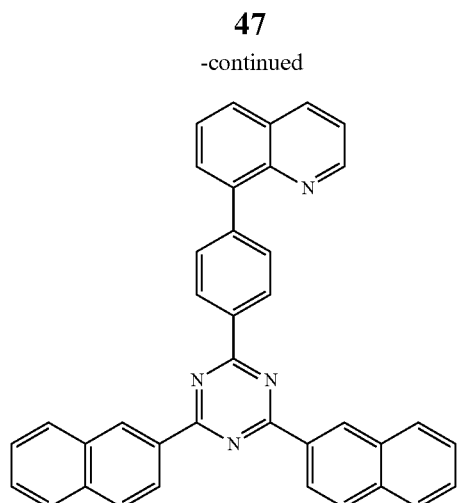
ET6
ET4
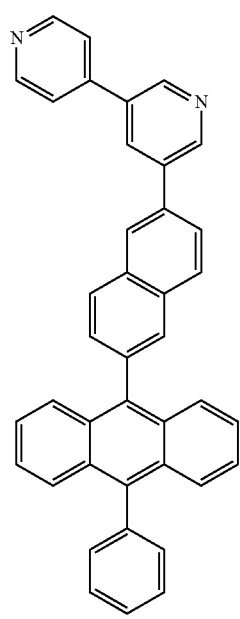
ET7
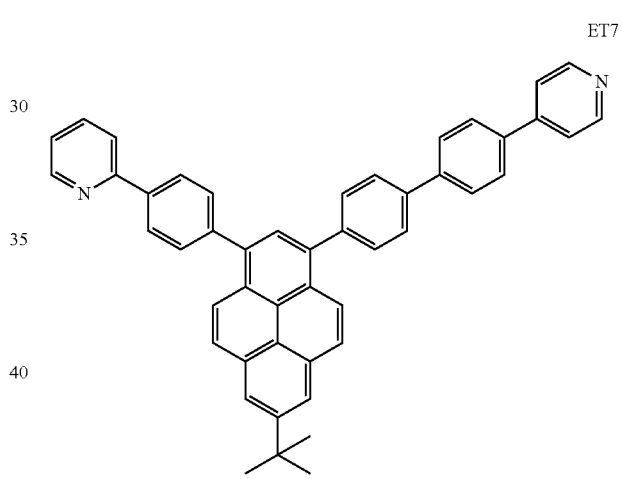
ET5
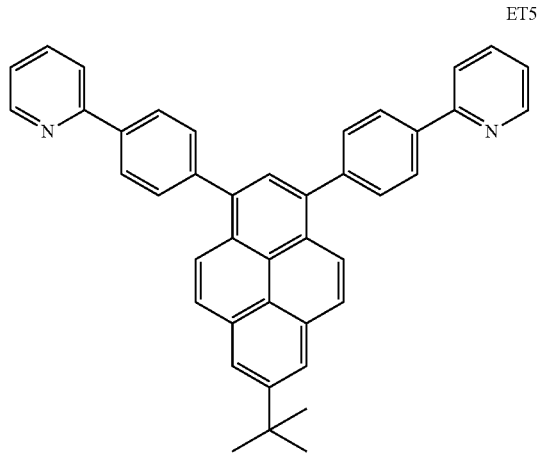
ET8
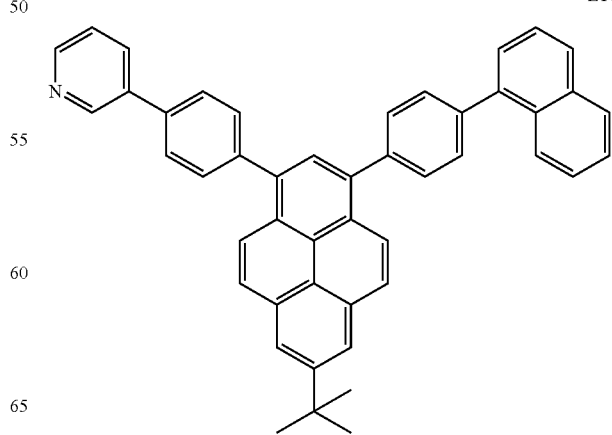

ET9
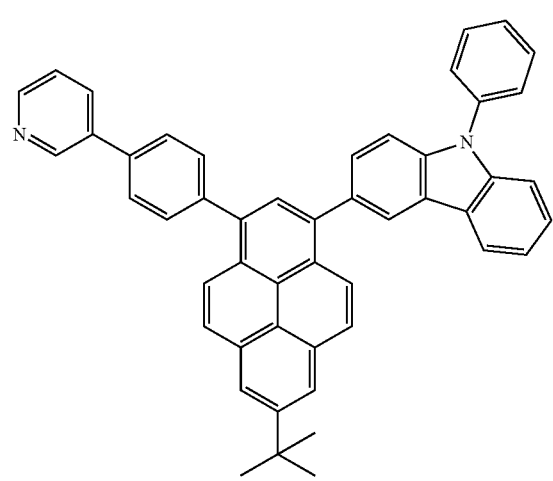
ET10
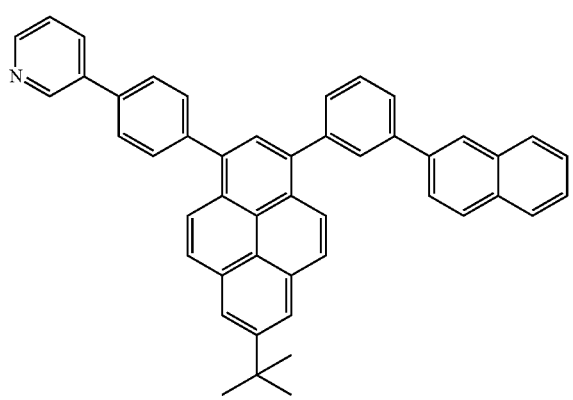
ET11
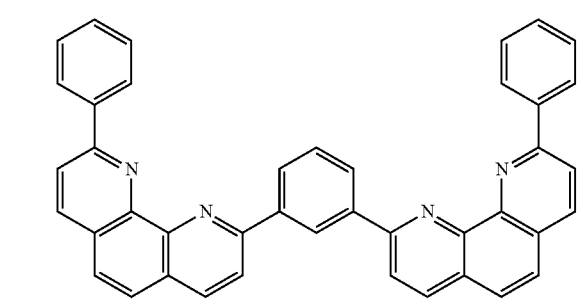
ET12
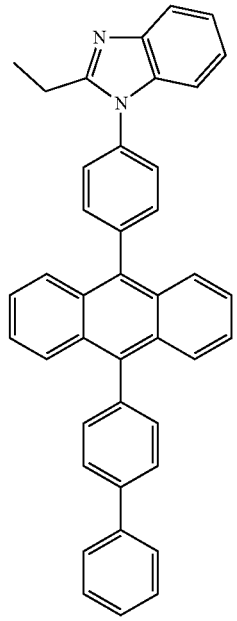
ET13
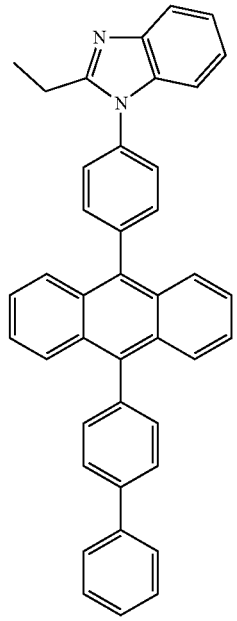
ET14
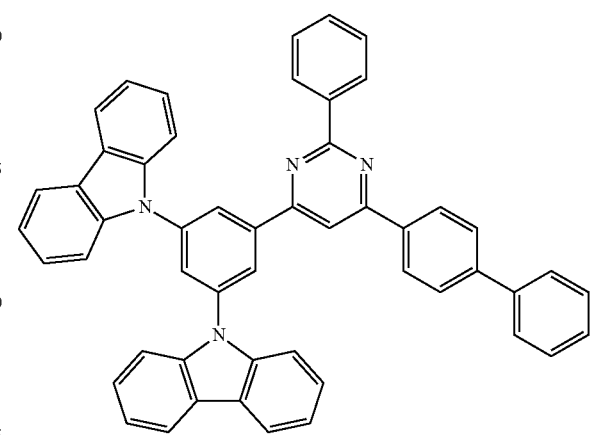
ET15
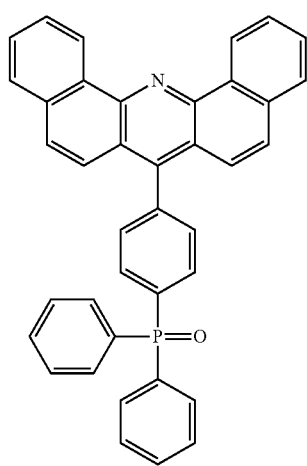

ET16

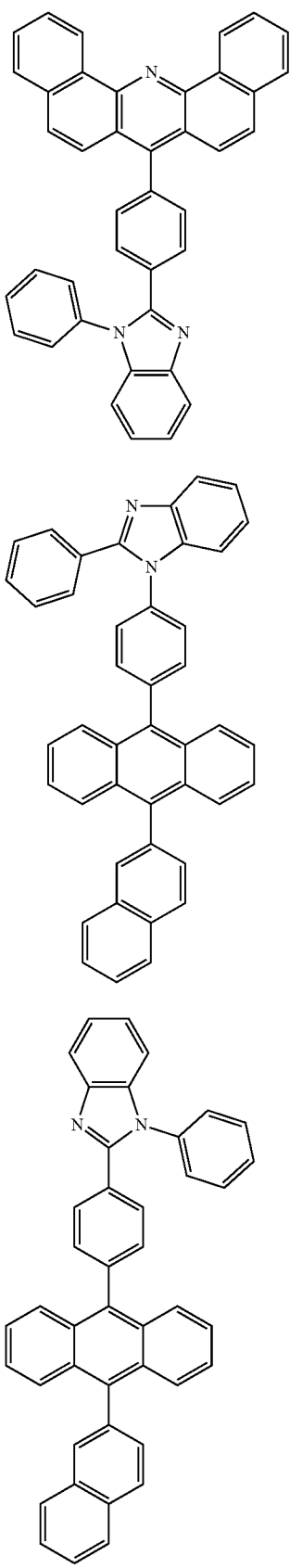

ET17

ET18

ET19

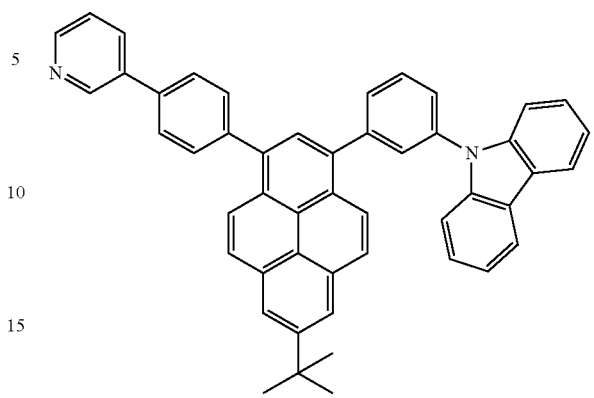

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1

ET-D2

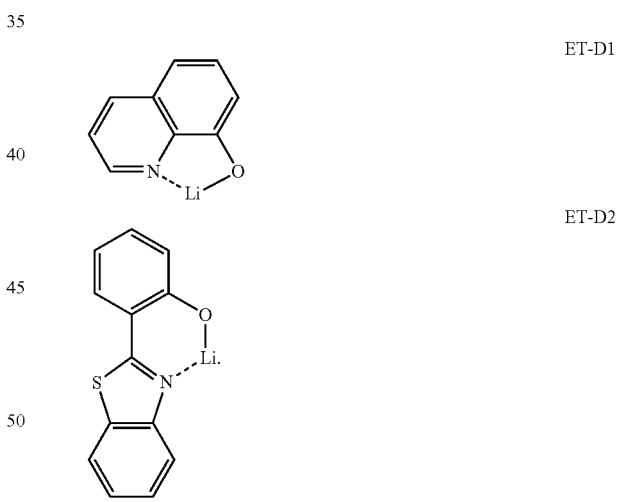

The electron transport region may include an electron injection layer (EIL) that promotes flow of electrons from the second electrode 19 thereinto.

The electron injection layer may include at least one selected from, LiF, NaCl, CsF, Li$_2$O, BaO, and LiQ.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In some embodiments, to manufacture a top emission type light-emitting device, a transmissive electrode formed using ITO or IZO may be used as the second electrode 19.

Hereinbefore, the organic light-emitting device has been described with reference to FIG. 1, but is not limited thereto.

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, a propyl group, an iso-butyl group, a sec-butyl group, a tert-butyl group, a pentyl group, an iso-amyl group, and a hexyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and non-limiting examples thereof include a methoxy group, an ethoxy group, and an iso-propyloxy group. The term "$C_1$-$C_{60}$ alkylthio group" as used herein refers to a monovalent group represented by —$SA_{102}$ (wherein $A_{102}$ is the $C_1$-$C_{60}$ alkyl group).

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group.

The term "$C_{10}$-$C_{10}$ heterocycloalkyl group" as used herein refers to a monovalent saturated monocyclic group having at least one heteroatom selected from N, O, Si, P, and S as a ring-forming atom and 1 to 10 carbon atoms, and non-limiting examples thereof include a 1,2,3,4-oxatriazolidinyl group, a tetrahydrofuranyl group, and a tetrahydrothiophenyl group.

The term "$C_6$-$C_{60}$ aryl group," as used herein refers to a monovalent group having a carbocyclic aromatic system having 6 to 30 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group includes two or more rings, the rings may be fused to each other.

The term "$C_1$-$C_{60}$ heteroaryl group" as used herein refers to a monovalent heterocyclic aromatic system having at least one heteroatom selected from N, O, Si, P, and S as a ring-forming atom and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group includes two or more rings, the rings may be fused to each other.

The term "$C_6$-$C_{60}$ aryloxy group" as used herein refers to —$OA_{103}$ (wherein $A_{103}$ is the $C_6$-$C_{60}$ aryl group), and a $C_6$-$C_{60}$ arylthio group used herein indicates —$SA_{104}$ (wherein $A_{104}$ is the $C_6$-$C_{60}$ aryl group).

The term "monovalent non-aromatic condensed polycyclic group" as used herein refers to a monovalent group (for example, having 8 to 60 carbon atoms) that has two or more rings condensed with each other, only carbon atoms as a ring-forming atom, and which is non-aromatic in the entire molecular structure. Non-limiting examples of the monovalent non-aromatic condensed polycyclic group include a fluorenyl group.

The term "monovalent non-aromatic condensed heteropolycyclic group" as used herein refers to a monovalent group (for example, having 1 to 60 carbon atoms) that has two or more rings condensed to each other, has at least one heteroatom selected from N, O, Si, P, and S, other than carbon atoms, as a ring-forming atom, and which is non-aromaticity in the entire molecular structure. An example of the monovalent non-aromatic condensed heteropolycyclic group is a carbazolyl group.

The term "$C_5$-$C_{60}$ carbocyclic group" as used herein refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as a benzene, a monovalent group, such as a phenyl group, or a divalent group, such as a phenylene group. In some embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

Throughout the specification, at least one of substituents of the substituted $C_1$-$C_{60}$ alkyl group, substituted $C_1$-$C_{60}$ alkoxy group, substituted $C_1$-$C_{60}$ alkylthio group, substituted $C_3$-$C_{10}$ cycloalkyl group, substituted $C_1$-$C_{10}$ heterocycloalkyl group, substituted $C_6$-$C_{30}$ aryl group, substituted $C_1$-$C_{30}$ heteroaryl group, substituted $C_6$-$C_{60}$ aryloxy group, substituted $C_6$-$C_{60}$ arylthio group, substituted monovalent non-aromatic condensed polycyclic group, substituted monovalent non-aromatic condensed heteropolycyclic group, substituted $C_5$-$C_{60}$ carbocyclic group, and substituted $C_1$-$C_{60}$ heterocyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$);

wherein $Q_{11}$ to $Q_{13}$, $Q_{21}$ to $Q_{23}$ and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{60}$ alkyl" refers to a $C_1$-$C_{60}$ alkyl group substituted with $C_6$-$C_{60}$ aryl group, the total number of carbon atoms in the resulting aryl substituted alkyl group is $C_7$-$C_{120}$.

The term "a biphenyl group" as used herein refers to "a phenyl group substituted with a substituted or unsubstituted phenyl group". In other words, the "biphenyl group" is a substituted phenyl group having a $C_6$-$C_{60}$ aryl group as a substituent.

The term "a terphenyl group" as used herein refers to "a phenyl group substituted with a substituted or unsubstituted biphenyl group." In other words, the term "terphenyl group" refers to a substituted phenyl group having, as a substituent, a $C_6$-$C_{60}$ aryl group substituted with a $C_6$-$C_{60}$ aryl group.

Hereinafter, a compound according to embodiments and an organic light-emitting device according to embodiments will be described in detail with reference to Synthesis Examples and Examples. The wording "B was used instead of A" used in describing Synthesis Examples means that a molar equivalent of A was identical to a molar equivalent of B.

EXAMPLES

Synthesis Example 1: Synthesis of Compound 1

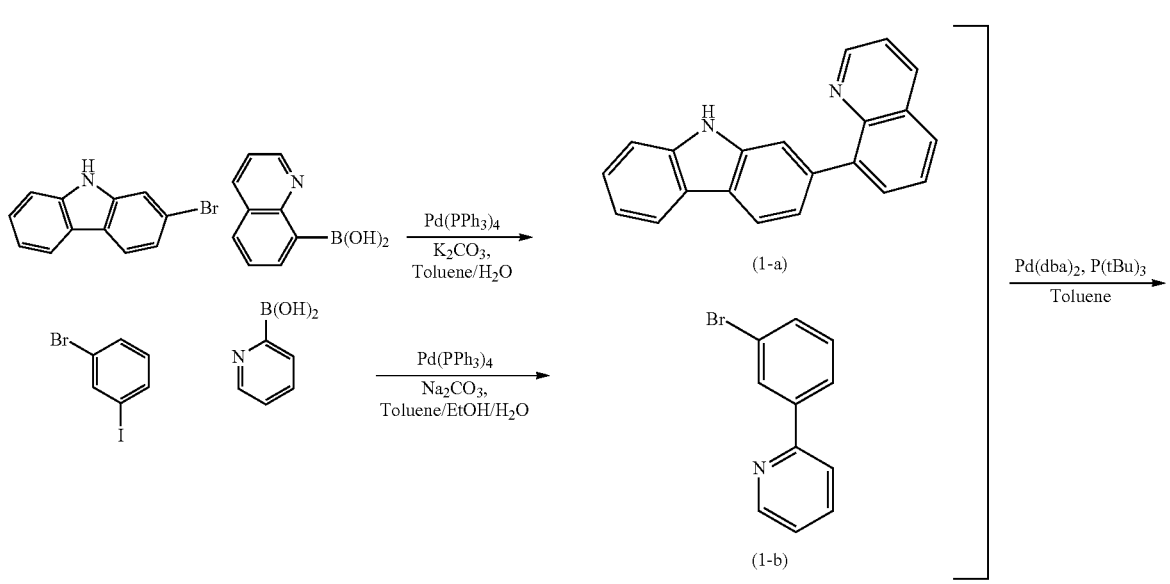

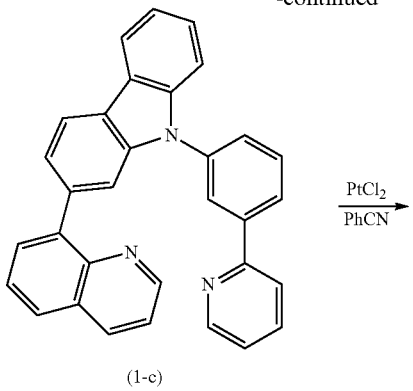

(1-c)

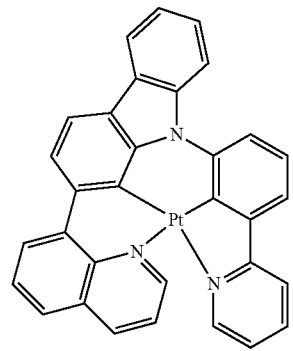

1

Synthesis of Intermediate 1-a 2-bromo-9H-carbazole (2.35 grams (g), 10 millimoles (mmol)), a phenylboronic acid (1.34 g, 11 mmol), and tetrakis(triphenylphosphine)palladium(0) (Pd(PPh$_3$)$_4$ (0.8 g, 0.7 mmol) potassium carbonate (K$_2$CO$_3$, 3.4 g, 25 mmol) were loaded into a 2-neck flask. The flask was purged with nitrogen and the mixture was reacted at a temperature of 125'C for 24 hours. The resultant was cooled to room temperature, and an extraction process was performed thereon by using ethyl acetate/water (EA/H$_2$O) to obtain an organic layer.

The organic layer was dried by using magnesium sulfate (MgSO$_4$) and condensed. The resultant was subjected to column chromatography (hexane:EA=2:1 at a volumetric ratio), thereby completing the preparation of Intermediate 1-a (Yield=67%).

Synthesis of Intermediate 1-b 1-bromo-3-iodobenzene (2.06 g, 20 mmol), a pyridin-2-ylboronic acid (3.2 g, 26 mmol), tetrakis(triphenylphosphine)palladium(0) (Pd(PPh$_3$)$_4$, (1.6 g, 1.4 mmol), and sodium carbonate (Na$_2$CO$_3$, 5.3 g, 50 mmol) were loaded into a flask, and 50 mL of toluene and a mixture of ethanol/H$_2$O (15 mL/15 mL) were added thereto. The flask was purged with nitrogen, and the mixture was reacted at a temperature of 105° C. for 24 hours. The reaction product was cooled to room temperature, and subjected to an extraction process using EA and water, thereby obtaining an organic layer. The organic layer was dried by using magnesium sulfate (MgSO$_4$) and then condensed. The resultant was subjected to column chromatography (hexane:EA=3:1 at a volumetric ratio), thereby completing the preparation of Intermediate 1-b (Yield=67%).

Synthesis of Intermediate 1-c

Intermediate 1-a (2.06 g, 7 mmol), Intermediate 1-b (2.34 g, 10 mmol), bis(dibenzylideneacetone)palladium(0) (Pd (dba)$_2$, 0.29 g, 0.5 mmol), tri-tert-butylphosphine (P(t-Bu)$_3$, 0.2 g, 1.0 mmol), and sodium tert-butoxide (NaOtBu, 0.7 g, 7 mmol) were loaded into a flask, and 50 mL of toluene was added thereto. The flask was purged with nitrogen and the mixture was refluxed for 48 hours. The reaction product was cooled to room temperature and subjected to an extraction process using dichloromethane/water (MC/H$_2$O) to obtain an organic layer. The organic layer was dried by using magnesium sulfate (MgSO$_4$), and condensed. The resultant was subjected to column chromatography (hexane/dichloromethane=1:1 at a volumetric ratio), thereby completing the preparation of Intermediate 1-c (Yield=75%).

Synthesis of Compound 1

Intermediate 1-c (1.56 g, 3.5 mmol) and platinum (II) chloride (PtCl$_2$, 0.93 g, 3.5 mmol) were loaded into a flask, and 60 mL of benzonitrile was added thereto. The flask was purged with nitrogen, and the mixture was reacted at a temperature of 190° C. for 24 hours. Then, under reduced pressure, the solvent was removed therefrom. Column chromatography (hexane:dichloromethane=2:1 at a volumetric ratio) was performed thereon to obtain a solid, which was recrystallized by using MC, thereby completing the preparation of Compound 1 (Yield=40%). (MS: m/z calcd 640.60. found 641.57).

Synthesis Example 2: Synthesis of Compound 3

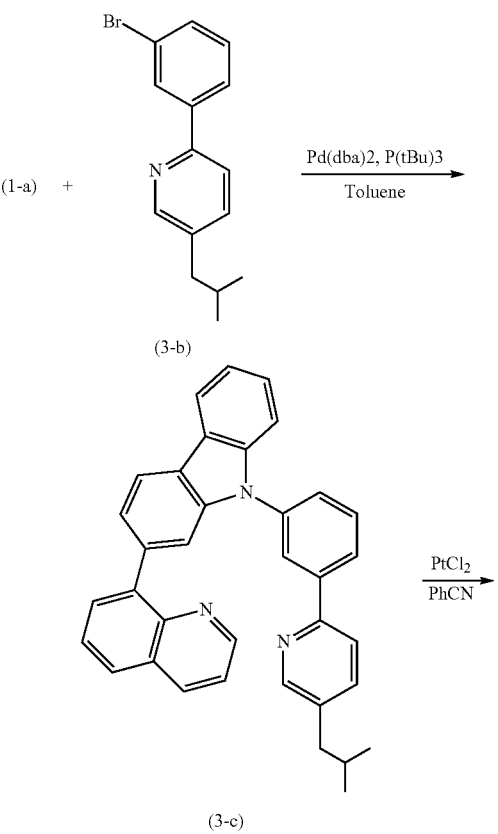

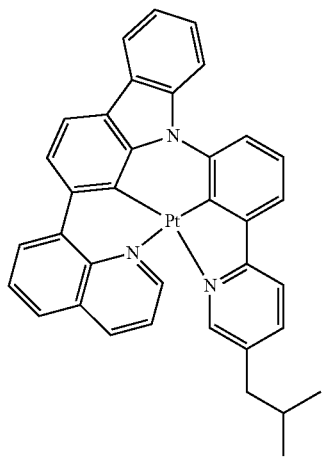

3

Synthesis of Intermediate 3-c

Intermediate 3-c was synthesized in the same manner as Intermediate 1-c in Synthesis Example 1, except that Intermediate 3-b was used instead of Intermediate 1-b.

Synthesis of Compound 3

Compound 3 was synthesized in the same manner as Compound 1 in Synthesis Example 1, except that Intermediate 3-c was used instead of Intermediate 1-c. (Yield=35%). (MS: m/z calcd 696.19. found 700.23).

Synthesis Example 3: Synthesis of Compound 13

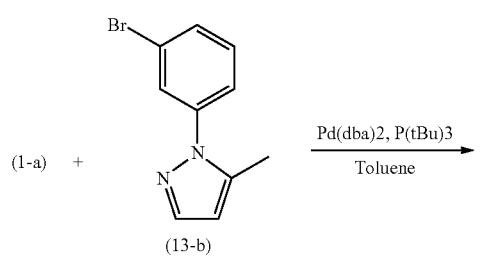

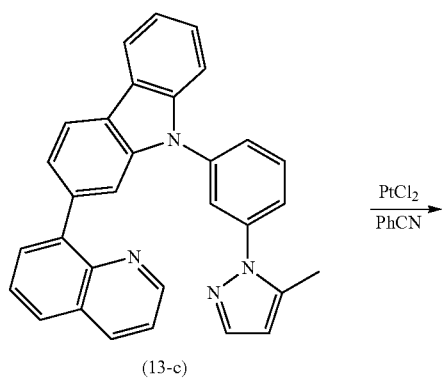

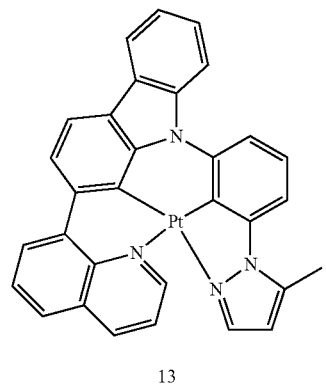

13

Synthesis of Intermediate 13-c

Intermediate 13-c was synthesized in the same manner as Intermediate 1-c in Synthesis Example 1, except that Intermediate 13-b was used instead of Intermediate 1-b.

Synthesis of Compound 13

Compound 13 was synthesized in the same manner as Compound 1 in Synthesis Example 1, except that Intermediate 13-c was used instead of Intermediate 1-c. (Yield=35%). (MS: m/z calcd 643.13. found 643.97).

Synthesis Example 4: Compound 17

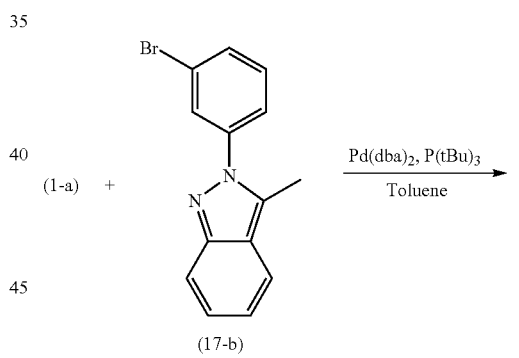

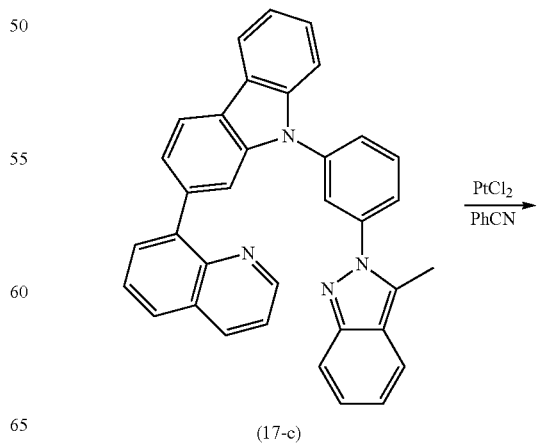

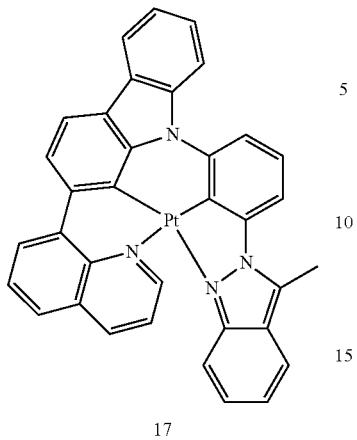

17

Synthesis of Intermediate 17-c

Intermediate 17-c was synthesized in the same manner as Intermediate 1-c in Synthesis Example 1, except that Intermediate 17-b was used instead of Intermediate 1-b.

Synthesis of Compound 17

Compound 17 was synthesized in the same manner as Compound 1 in Synthesis Example 1, except that Intermediate 17-c was used instead of Intermediate 1-c. (Yield=35%). (MS: m/z calcd 693.15. found 694.04).

Synthesis Example 5: Synthesis of Compound 18

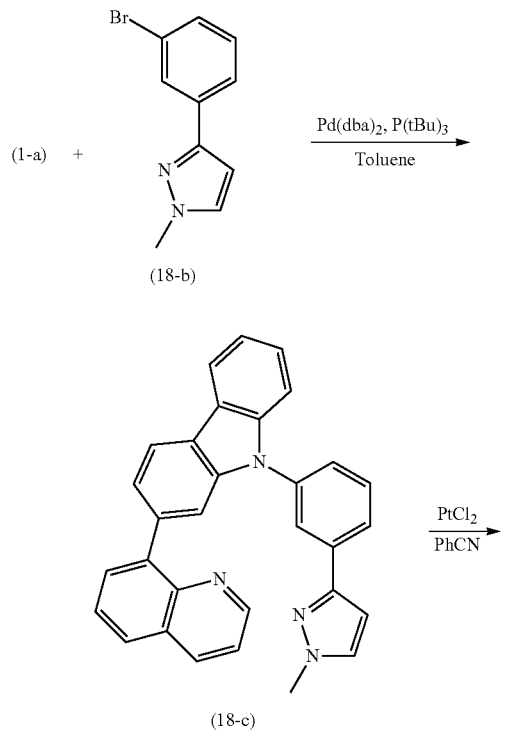

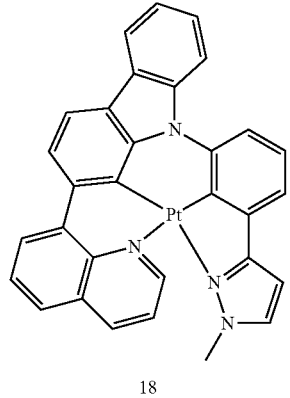

18

Synthesis of Intermediate 18-c

Intermediate 18-c was synthesized in the same manner as Intermediate 1-c in Synthesis Example 1, except that Intermediate 18-b was used instead of Intermediate 1-b.

Synthesis of Compound 18

Compound 18 was synthesized in the same manner as Compound 1 in Synthesis Example 1, except that Intermediate 18-c was used instead of Intermediate 1-c. (Yield=42%). (MS: m/z calcd 643.13. found 644.12).

Evaluation Example 1: Evaluating Ultraviolet (UV)-Visible (Vis) Absorption Spectrum and Photoluminecscence (PL) Spectrum Luminescent characteristics of Compound 3 were evaluated by UV-Vis absorption spectrum and PL spectrum.

Figure 2:
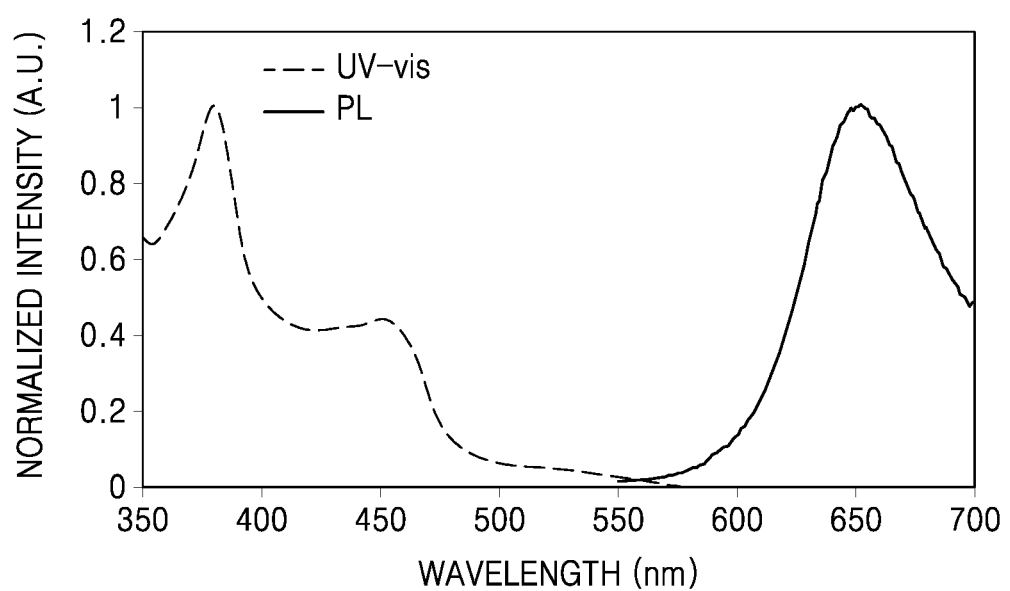
FIG. 2 is a graph of normalized intensity (arbitrary units, a. u.) versus wavelength (nanometers, nm), showing an ultraviolet (UV)-visible (Vis) absorption spectrum and photoluminescence (PL) spectrum of Compound 3 according to an embodiment.
Figure 3:
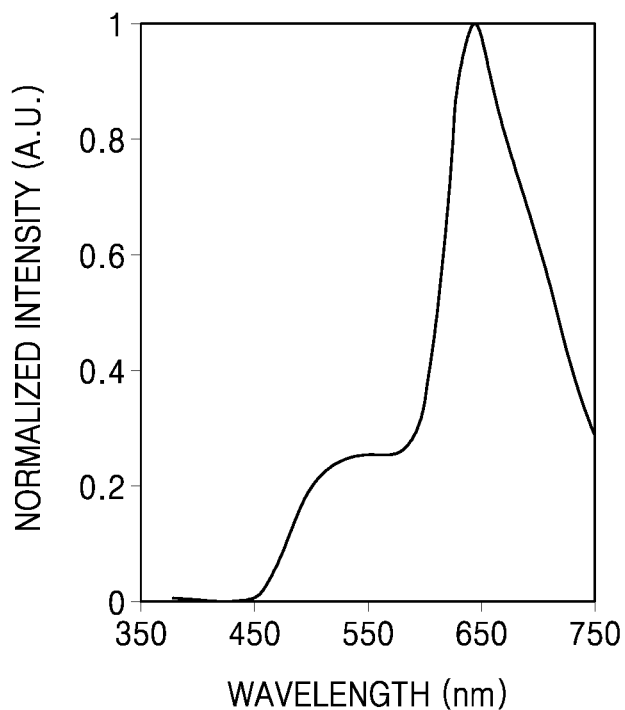
FIG. 3 is a graph of normalized intensity (arbitrary units, a. u.) versus wavelength (nanometers, nm), showing an electroluminescent (EL) spectrum of an organic light-emitting device according to Example 1.
Figure 4:
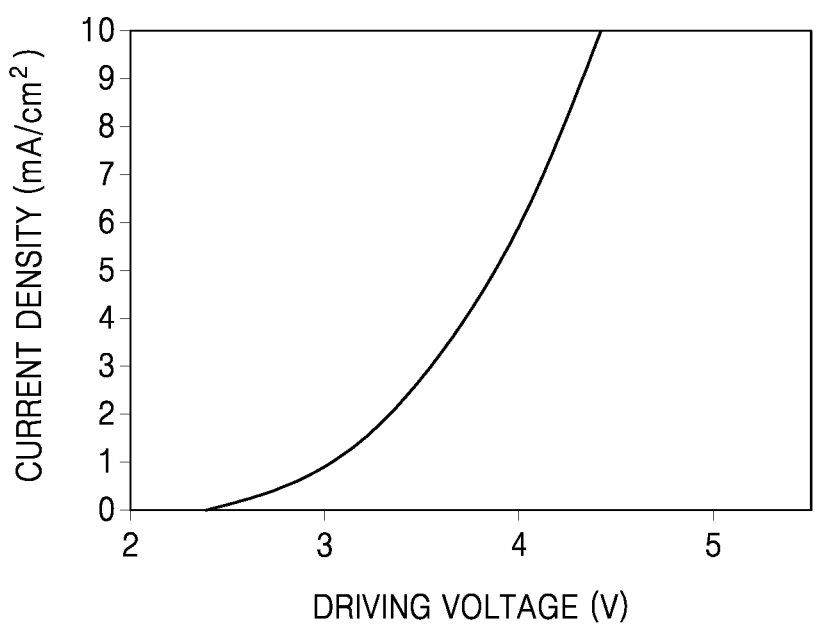
FIG. 4 is a graph of current density (milliamperes per square centimeter) versus driving voltage (volts, V), showing a current density-voltage (J-V) graph of an organic light-emitting device according to Example 1.

Compound 3 was diluted to a concentration of $1\times10^{-5}$ molar (M) by using toluene, and UV-Vis absorption spectrum thereof was measured at room temperature by using Shimadzu UV-350 Spectrometer. Compound 3 was diluted to a concentration of 10 millimolar (mM) by using toluene, and the PL spectrum thereof was measured at room temperature by using a xenon lamp-mounted ISC PC1 spectrofluorometer. Results thereof are shown in FIG. 2.

Example 1

As an anode, a glass substrate with ITO/Ag/ITO respectively having thicknesses of 70 Å/1,000 Å/70 Å deposited thereon was cut to a size of 50 mm×50 mm×0.5 mm (mm=millimeter), and sonicated by using iso-propyl alcohol and pure water, each for 5 minutes, followed by exposure to ultraviolet rays for 30 minutes and then ozone, and mounted on a vacuum deposition apparatus.

2-TNATA was deposited on the anode to form a hole injection layer having a thickness of 600 Å, and then, 4,4'-bis[N-(1-naphthyl)-N-phenylamino]biphenyl (NPB) was deposited thereon to form a hole transport layer having a thickness of 1,350 Å.

CBP (host) and Compound 3 (dopant) were co-deposited on the hole transport layer at a weight ratio of 94:6 to form an emission layer having a thickness of 400 Å, and then, BCP was deposited on the emission layer to form a hole blocking layer having a thickness of 50 Å. Then, Alq$_3$ was deposited on the hole blocking layer to form an electron transport layer having a thickness of 350 Å, and then, LiF was deposited on the electron transport layer to form an electron injection layer having a thickness of 10 Å. Then, Mg and Ag were deposited on the electron injection layer at a weight ratio of 90:10 to form a cathode having a thickness of 120 Å, thereby completing the manufacture of an organic light-emitting device (emitting red light).

Examples 2 to 4 and Comparative Example 1

Organic light-emitting devices were manufactured in the same manner as in Example 1, except that, as the dopant used in forming the emission layer, compounds shown in Table 2 were each used instead of Compound 1.

Comparative Example 1

An organic light-emitting device was manufactured in the same manner as in Example 1, except that in forming the emission layer, PtOEP was used instead of Compound 1.

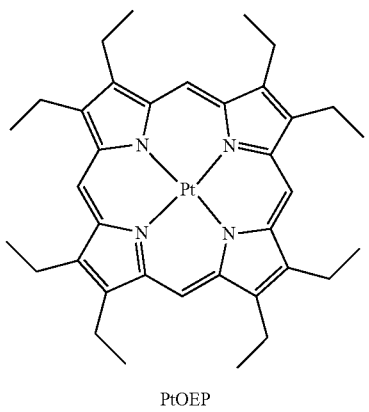

PtOEP

Evaluation Example 2: Evaluating Characteristics of Organic Light-Emitting Devices The driving voltage, current density, luminance, efficiency, emission color, color coordinate, and lifespan ($T_{97}$) of the organic light-emitting devices of Examples 1 to 4 and Comparative Example 1 were evaluated. The results are shown in Table 2. A current-voltage meter (Keithley 2400) and a luminance meter (Minolta Cs-1000A) were used as an evaluation device. The lifespan ($T_{97}$) refers to a period of time that has elapsed until the initial luminance 100% of the initial luminance is reduced to 97% thereof.

TABLE 2

| | Dopant | Driving voltage (V) | Efficiency (cd/A) | CIEx | $LT_{97}$ (hours) |
|---|---|---|---|---|---|
| Example 1 | Compound 3 | 4.6 | 5.6 | 0.546 | 270 |
| Example 2 | Compound 13 | 5.2 | 8.5 | 0.556 | 195 |
| Example 3 | Compound 17 | 5.6 | 5.2 | 0.587 | 135 |
| Example 4 | Compound 18 | 6.1 | 10.2 | 0.524 | 75 |
| Comparative Example 1 | PtOEP | 7.3 | 4.5 | 0.69 | 40 |

Referring to Table 2, it was determined that the organic light-emitting devices of Examples 1 to 4 have a lower driving voltage, higher efficiency, and a longer lifespan than the organic light-emitting device of Comparative Example 1.

Due to the inclusion of an organometallic compound having excellent optical characteristics, electric characteristics and thermal stability according to an embodiment of the present disclosure, an organic light-emitting device may have a low driving voltage, high efficiency, long lifespan, and high color purity.

It should be understood that embodiments described herein should be considered in a descriptive sense only and not for purposes of limitation. Descriptions of features or aspects within each embodiment should typically be considered as available for other similar features or aspects in other embodiments.

While embodiments have been described with reference to the figures, it will be understood by those of ordinary skill in the art that various changes in form and details may be made therein without departing from the spirit and scope of the present disclosure as defined by the following claims.

What is claimed is:
1. An organometallic compound represented by Formula 1:

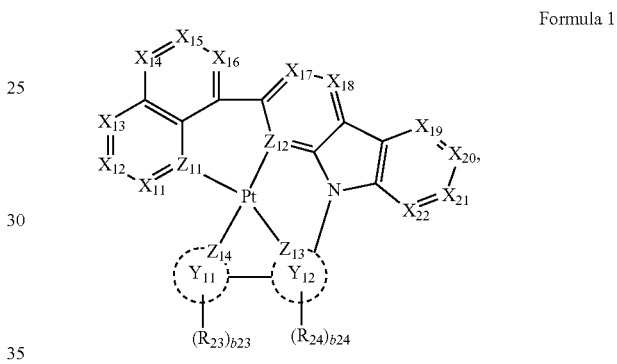

Formula 1 wherein, in Formula 1,
$X_{11}$ is selected from $C(R_{11})$ and nitrogen atom (N); $X_{12}$ is selected from $C(R_{12})$ and N; $X_{13}$ is selected from $C(R_{13})$ and N; $X_{14}$ is selected from $C(R_{14})$ and N; $X_{15}$ is selected from $C(R_{15})$ and N; $X_{16}$ is selected from $C(R_{16})$ and N; $X_{17}$ is selected from $C(R_{17})$ and N; $X_{18}$ is selected from $C(R_{18})$ and N; $X_{19}$ is selected from $C(R_{19})$ and N; $X_{20}$ is selected from $C(R_{20})$ and N; $X_{21}$ is selected from $C(R_{21})$ and N; $X_{22}$ is selected from $C(R_{22})$ and N;
$Z_{11}$ to $Z_{14}$ are each independently selected from N and carbon atom (C);
$Y_{11}$ and $Y_{12}$ are each independently selected from a $C_5$-$C_{60}$ carbocyclic group and a $C_1$-$C_{60}$ heterocyclic group;
$R_{11}$ to $R_{24}$ are each independently selected from hydrogen, deuterium, —F, —Cl, —Br, —I, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_3$)($Q_4$)($Q_5$), —Ge(Q$_3$)(Q$_4$)(Q$_5$), —N(Q$_3$)(Q$_4$), —B(Q$_3$)(Q$_4$), —C(=O)(Q$_3$), —S(=O)$_2$(Q$_3$), and —P(=O)(Q$_3$)(Q$_4$);

provided that two neighboring substituents selected from R$_{11}$ to R$_{24}$ are optionally linked to form a substituted or unsubstituted saturated ring or a substituted or unsubstituted unsaturated ring, b23 is an integer from 0 to the maximum number of R$_{23}$ that can be attached to Y$_{11}$; and b24 is an integer from 0 to the maximum number of R$_{24}$ that can be attached to Y$_{12}$;

wherein Q$_3$ to Q$_5$ are each independently selected from hydrogen, deuterium, a C$_1$-C$_{60}$ alkyl group, a C$_6$-C$_{60}$ aryl group, a C$_1$-C$_{60}$ heteroaryl group, a monovalent non-aromatic condensed polycyclic group, and a monovalent non-aromatic condensed heteropolycyclic group.

2. The organometallic compound of claim 1, wherein X$_{11}$ is C(R$_{11}$); X$_{12}$ is C(R$_{12}$); X$_{13}$ is C(R$_{13}$); X$_{14}$ is N; X$_{15}$ is C(R$_{15}$); X$_{16}$ is C(R$_{16}$); X$_{17}$ is C(R$_{17}$); X$_{18}$ is C(R$_{18}$); X$_{19}$ is C(R$_{19}$); X$_{20}$ is C(R$_{20}$); X$_{21}$ is C(R$_{21}$); and X$_{22}$ is C(R$_{22}$); or X$_{11}$ is C(R$_{11}$); X$_{12}$ is C(R$_{12}$); X$_{13}$ is C(R$_{13}$); X$_{14}$ is C(R$_{14}$); X$_{15}$ is C(R$_{15}$); X$_{16}$ is C(R$_{16}$); X$_{17}$ is C(R$_{17}$); X$_{18}$ is C(R$_{18}$); X$_{19}$ is C(R$_{19}$); X$_{20}$ is C(R$_{20}$); X$_{21}$ is C(R$_{21}$); and X$_{22}$ is C(R$_{22}$).

3. The organometallic compound of claim 1, wherein Z$_{11}$ is N and Z$_{12}$ is C.

4. The organometallic compound of claim 1, wherein Z$_{13}$ is C and Z$_{14}$ is N.

5. The organometallic compound of claim 1, wherein
Z$_{11}$ is N, Z$_{12}$ is C, Z$_{13}$ is N, and Z$_{14}$ is C;
Z$_{11}$ is N, Z$_{12}$ is C, Z$_{13}$ is C, and Z$_{14}$ is N;
Z$_{11}$ is C, Z$_{12}$ is N, Z$_{13}$ is N, and Z$_{14}$ is C; or
Z$_{11}$ is C, Z$_{12}$ is N, Z$_{13}$ is C, and Z$_{14}$ is N.

6. The organometallic compound of claim 1, wherein Z$_{11}$ is N, Z$_{12}$ is C, Z$_{13}$ is C, and Z$_{14}$ is N.

7. The organometallic compound of claim 1, wherein Y$_{11}$ and Y$_{12}$ are each independently selected from a benzene group, a naphthalene group, a phenanthrene group, an anthracene group, a triphenylene group, a pyrene group, a chrysene group, a fluorene group, a pyrrole group, an imidazole group, a pyrazole group, a thiazole group, an isothiazole group, an oxazole group, an isoxazole group, an oxadiazole group, a triazole group, a pyridine group, a pyrimidine group, a pyrazine group, a pyridazine group, a triazine group, a quinoline group, an isoquinoline group, a quinoxaline group, a quinazoline group, an indole group, an iso-indole group, a benzimidazole group, a benzoxazole group, an isobenzoxazole group, an indazole group, a benzofuran group, a benzothiophene group, an indenopyridine group, a carbazole group, a carboline group, a dibenzofuran group, a dibenzothiophene group, a dibenzosilole group, and a benzosilolopyridine group.

8. The organometallic compound of claim 1, wherein Y$_{11}$ and Y$_{12}$ are each independently selected from a benzene group, a naphthalene group, a phenanthrene group, an anthracene group, a fluorene group, an imidazole group, a pyrazole group, a triazole group, a pyridine group, a pyrimidine group, a pyrazine group, a pyridazine group, a triazine group, a quinoline group, an isoquinoline group, an indole group, an iso-indole group, a benzimidazole group, an indazole group, a benzofuran group, a benzothiophene group, an indenopyridine group, a carbazole group, a carboline group, a dibenzofuran group, a benzofuranopyridine group, a dibenzothiophene group, a benzothiophenopyridine group, a dibenzosilole group, and a benzosilolopyridine group.

9. The organometallic compound of claim 1, wherein Y$_{11}$ and Y$_{12}$ are each independently selected from a benzene group, a naphthalene group, a fluorene group, an imidazole group, a pyrazole group, a triazole group, a pyridine group, a pyrimidine group, a pyrazine group, a triazine group, a quinoline group, an isoquinoline group, an indole group, an iso-indole group, a benzimidazole group, an indazole group, an indenopyridine group, a carbazole group, a carboline group, a dibenzofuran group, a benzofuranopyridine group, a dibenzothiophene group, a benzothiophenopyridine group, a dibenzosilole group, and a benzosilolopyridine group.

10. The organometallic compound of claim 1, wherein at least one selected from Y$_{11}$ and Y$_{12}$ is selected from a C$_1$-C$_{60}$ heterocyclic group.

11. The organometallic compound of claim 1, wherein moieties represented by Y$_{11}$-Y$_{12}$ are selected from Formulae 3-1 to 3-29:

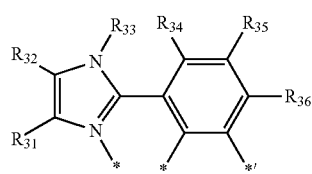

3-1

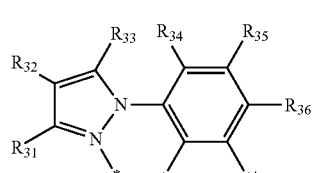

3-2

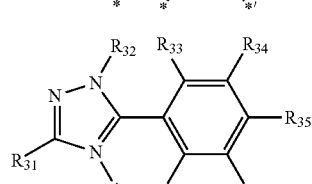

3-3

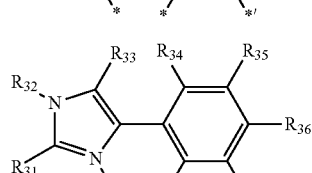

3-4

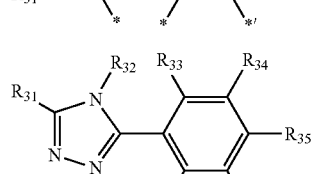

3-5

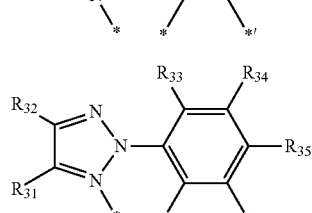

3-6

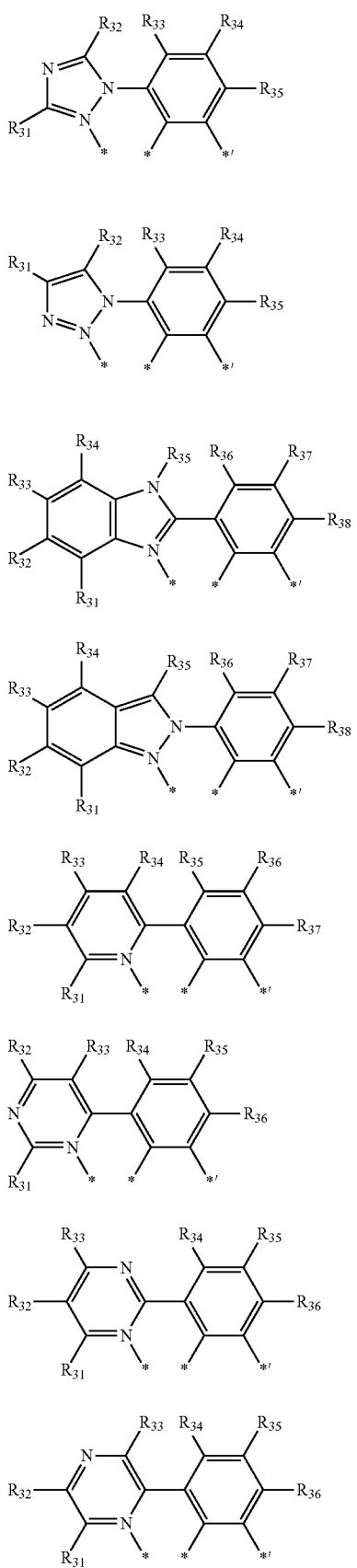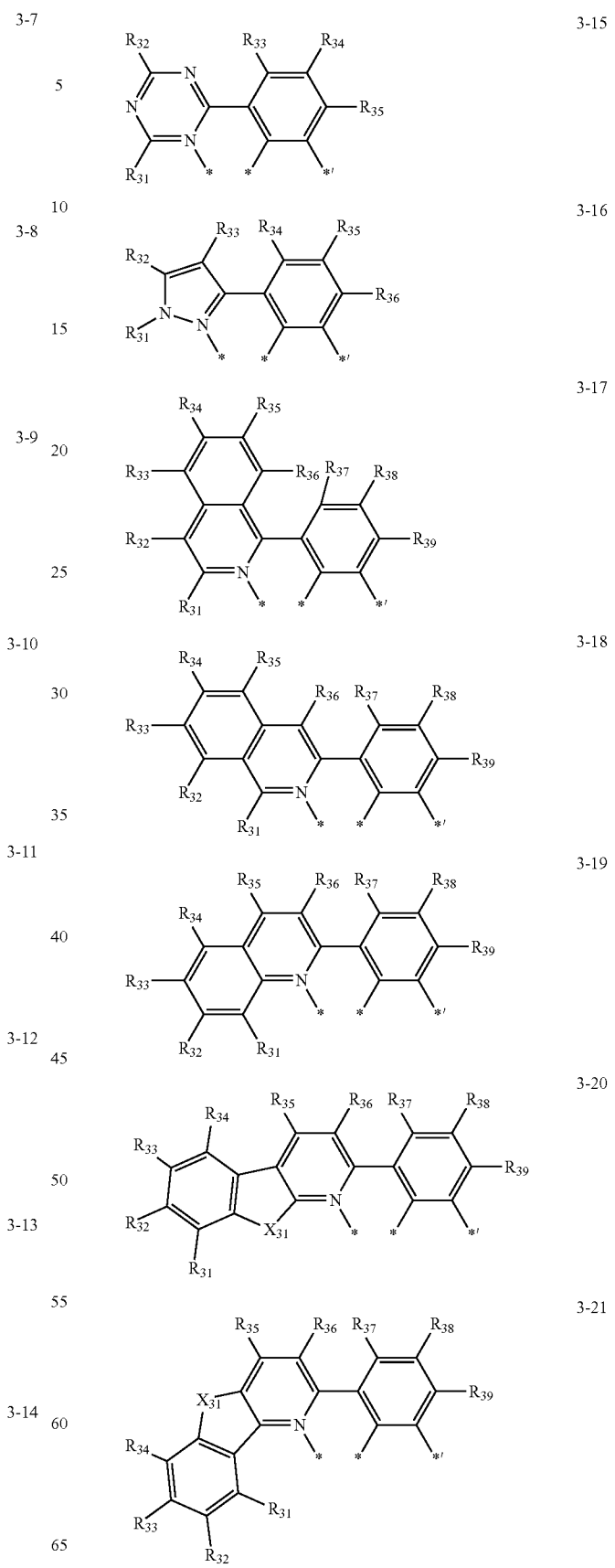

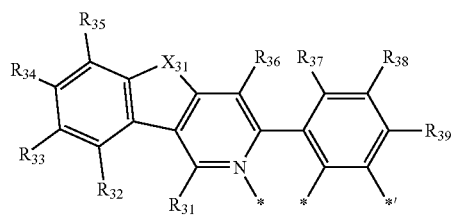
3-22

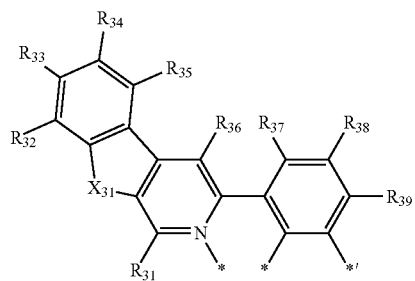
3-23

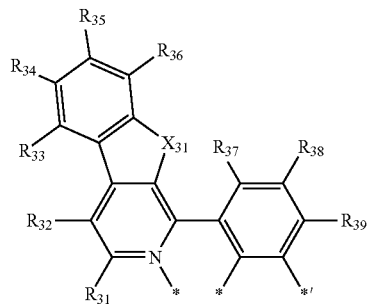
3-24

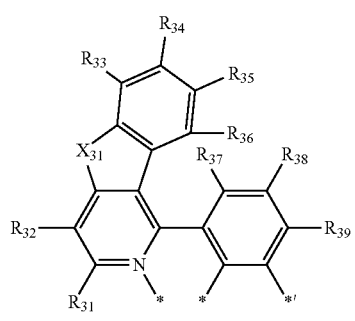
3-25

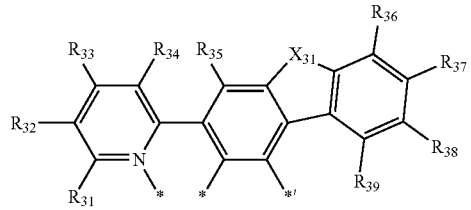
3-26

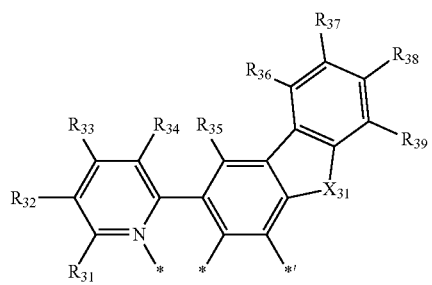
3-27

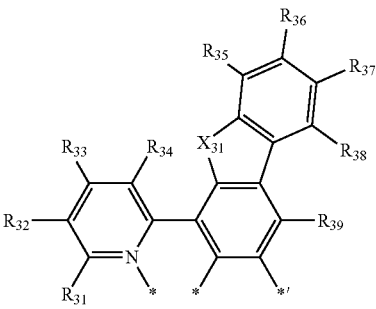
3-28

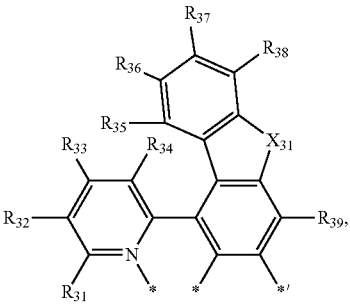
3-29 wherein, in Formulae 3-1 to 3-29, $X_{31}$ is selected from $C(R_{40})(R_{41})$, $N(R_{41})$, O, S, and $Si(R_{40})(R_{41})$;

$R_{31}$ to $R_{41}$ are each independently selected from hydrogen, deuterium, —F, a cyano group, a methyl group, an ethyl group, an n-propyl group, an iso-propyl group, an n-butyl group, an iso-butyl group, a sec-butyl group, a tert-butyl group, —CFH$_2$, —CF$_2$H, —CF$_3$, and a benzyl group;

a phenyl group, a biphenyl group, a terphenyl group, a naphthyl group, a pyridinyl group, a pyrimidinyl group, a pyridazinyl group and a triazinyl group;

a phenyl group, a biphenyl group, a terphenyl group, a naphthyl group, a pyridinyl group, a pyrimidinyl group, a pyridazinyl group, and a triazinyl group, each substituted with at least one selected from deuterium, —F, a cyano group, a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, a pyridinyl group, a pyrimidinyl group, a pyridazinyl group, a triazinyl group, —Si(Q$_{21}$)(Q$_{22}$)(Q$_{23}$), —Ge(Q$_{21}$)(Q$_{22}$)(Q$_{23}$), and —N(Q$_{21}$)(Q$_{22}$); and —Si(Q$_{31}$)(Q$_{32}$)(Q$_{33}$), —Ge(Q$_{31}$)(Q$_{32}$)(Q$_{33}$), and —N(Q$_{31}$)(Q$_{32}$);

$Q_{21}$ to $Q_{23}$ and $Q_{31}$ to $Q_{33}$ are each independently selected from hydrogen, a methyl group, an ethyl group, an n-propyl group, an iso-propyl group, an n-butyl group, a phenyl group, a biphenyl group, and a terphenyl group;

* is a binding site to Pt in Formula 1; and

*' is a binding site to a neighboring nitrogen atom (N) in Formula 1.

12. The organometallic compound of claim 1, wherein $R_{11}$ to $R_{24}$ are each independently selected from hydrogen, deuterium, —F, —Cl, —Br, —I, a cyano group, a nitro group, an amidino group, a hydrazino group, a hydrazono group, a $C_1$-$C_{60}$ alkyl group, a $C_1$-$C_{60}$ alkoxy group, and a $C_1$-$C_{60}$ alkylthio group;

a $C_1$-$C_{60}$ alkyl group, a $C_1$-$C_{60}$ alkoxy group, and a $C_1$-$C_{60}$ alkylthio group, each substituted with at least one selected from deuterium, —F, —Cl, —Br, —I, a cyano group, a nitro group, an amidino group, a hydrazino group, a hydrazono group, a $C_3$-$C_{10}$ cycloalkyl group, a $C_1$-$C_{10}$ heterocycloalkyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{31}$)($Q_{32}$)($Q_{33}$), —Ge($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$);

a $C_3$-$C_{10}$ cycloalkyl group, a $C_1$-$C_{10}$ heterocycloalkyl group, a $C_6$-$C_{60}$ aryl group, a $C_1$-$C_{60}$ heteroaryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_6$-$C_{60}$ aryl group, a $C_1$-$C_{60}$ heteroaryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group, each substituted with at least one selected from deuterium, —F, —Cl, —Br, —I, a cyano group, a nitro group, an amidino group, a hydrazino group, a hydrazono group, a $C_1$-$C_{60}$ alkyl group, a $C_1$-$C_{60}$ alkoxy group, a $C_1$-$C_{60}$ alkylthio group, $C_3$-$C_{10}$ cycloalkyl group, a $C_1$-$C_{10}$ heterocycloalkyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{31}$)($Q_{32}$)($Q_{33}$), —Ge($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$); and —Si($Q_3$)($Q_4$)($Q_5$), —Ge($Q_3$)($Q_4$)($Q_5$), —N($Q_3$)($Q_4$), —B($Q_3$)($Q_4$), —C(=O)($Q_3$), —S(=O)$_2$($Q_3$), and —P(=O)($Q_3$)($Q_4$), wherein $Q_3$ to $Q_5$ and $Q_{31}$ to $Q_{33}$ are each independently selected from hydrogen, deuterium, a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

13. The organometallic compound of claim 1, wherein $R_{11}$ to $R_{24}$ are each independently selected from hydrogen, deuterium, —F, a cyano group, a methyl group, an ethyl group, an n-propyl group, an iso-propyl group, an n-butyl group, an iso-butyl group, a sec-butyl group, a tert-butyl group, a methoxy group, an ethoxy group, an n-propoxy group, an iso-propoxy group, an n-butoxy group, an iso-butoxy group, a sec-butoxy group, and a tert-butoxy;

a methyl group, an ethyl group, an n-propyl group, an iso-propyl group, an n-butyl group, an iso-butyl group, a sec-butyl group, a tert-butyl group, a methoxy group, an ethoxy group, an n-propoxy group, an iso-propoxy group, an n-butoxy group, an iso-butoxy group, a sec-butoxy group, and a tert-butoxy group, each substituted with at least one selected from deuterium, —F, a cyano group, a cyclopentyl group, a cyclohexyl group, a phenyl group, a biphenyl group, a terphenyl group, a naphthyl group, a phenyloxy group, a phenylthio group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, a dibenzothiophenyl group, —Si($Q_{31}$)($Q_{32}$)($Q_{33}$), —Ge($Q_{31}$)($Q_{32}$)($Q_{33}$), and —N($Q_{31}$)($Q_{32}$);

a cyclopentyl group, a cyclohexyl group, a phenyl group, a biphenyl group, a terphenyl group, a naphthyl group, a phenyloxy group, a phenylthio group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, and a dibenzothiophenyl group;

a cyclopentyl group, a cyclohexyl group, a phenyl group, a biphenyl group, a terphenyl group, a naphthyl group, a phenyloxy group, a phenylthio group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, and a dibenzothiophenyl group, each substituted with at least one selected from deuterium, —F, a cyano group, a methyl group, an ethyl group, an n-propyl group, an iso-propyl group, an n-butyl group, an iso-butyl group, a sec-butyl group, a tert-butyl group, a methoxy group, an ethoxy group, an n-propoxy group, an iso-propoxy group, an n-butoxy group, an iso-butoxy group, a sec-butoxy group, a tert-butoxy group, a cyclopentyl group, a cyclohexyl group, a phenyl group, a biphenyl group, a terphenyl group, a naphthyl group, a phenyloxy group, a phenylthio group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, a dibenzothiophenyl group, —Si($Q_{31}$)($Q_{32}$)($Q_{33}$), —Ge($Q_{31}$)($Q_{32}$)($Q_{33}$), and —N($Q_{31}$)($Q_{32}$); and —Si($Q_3$)($Q_4$)($Q_5$), —Ge($Q_3$)($Q_4$)($Q_5$), and —N($Q_3$)($Q_4$), wherein $Q_3$ to $Q_5$ and $Q_{31}$ to $Q_{33}$ are each independently selected from hydrogen, a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, a pyridinyl group, a pyrimidinyl group, a pyridazinyl group, a triazinyl group, a quinolinyl group, an isoquinolinyl group, a fluorenyl group, a carbazolyl group, a dibenzofuranyl group, and a dibenzothiophenyl group.

14. The organometallic compound of claim 1, wherein $R_{11}$ to $R_{24}$ are each independently selected from hydrogen, deuterium, —F, a cyano group, a methyl group, an ethyl group, an n-propyl group, an iso-propyl group, an n-butyl group, an iso-butyl group, a sec-butyl group, a tert-butyl group, —CFH$_2$, —CF$_2$H, —CF$_3$, and a benzyl group;

a phenyl group, a biphenyl group, a terphenyl group, a naphthyl group, a pyridinyl group, a pyrimidinyl group, a pyridazinyl group, and a triazinyl group;

a phenyl group, a biphenyl group, a terphenyl group, a naphthyl group, a pyridinyl group, a pyrimidinyl group, a pyridazinyl group, and a triazinyl group, each substituted with at least one selected from deuterium, —F, a cyano group, a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, a pyridinyl group, a pyrimidinyl group, a pyridazinyl group, a triazinyl group, —Si(Q$_{31}$)(Q$_{32}$)(Q$_{33}$), —Ge(Q$_{31}$)(Q$_{32}$)(Q$_{33}$), and —N(Q$_{31}$)(Q$_{32}$); and —Si(Q$_3$)(Q$_4$)(Q$_5$), —Ge(Q$_3$)(Q$_4$)(Q$_5$), and —N(Q$_3$)(Q$_4$),
wherein Q$_3$ to Q$_5$ and Q$_{31}$ to Q$_{33}$ are each independently selected from hydrogen, a methyl group, an ethyl group, an n-propyl group, an iso-propyl group, an n-butyl group, a phenyl group, a biphenyl group, and a terphenyl group.

15. The organometallic compound of claim 1, wherein
the organometallic compound represented by Formula 1 is represented by one of Formulae 1-1 and 1-2:

Formula 1-1

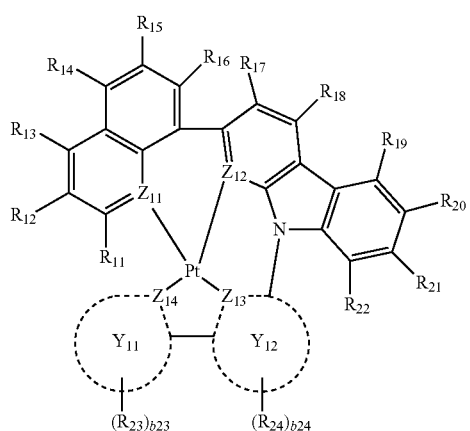

Formula 1-2

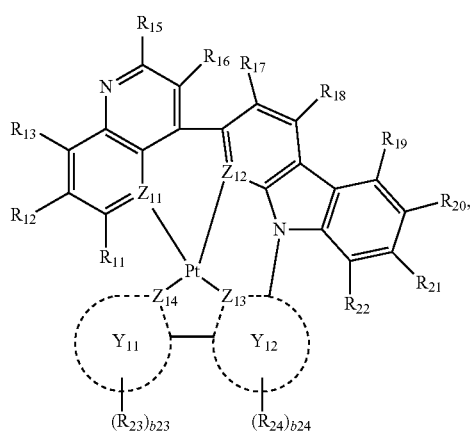

wherein, in Formulae 1-1 and 1-2,
Z$_{11}$ to Z$_{14}$, Y$_{11}$, Y$_{12}$, R$_{11}$ to R$_{24}$, b23, and b24 are the same as in Formula 1.

16. The organometallic compound of claim 1, wherein
the organometallic compound represented by Formula 1 is represented by one of Formulae 1-11 and 1-12:

Formula 1-11

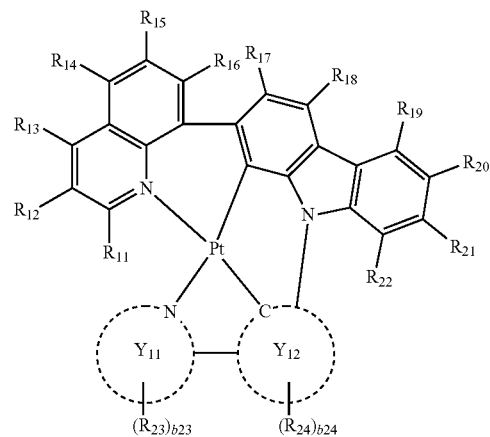

Formula 1-12

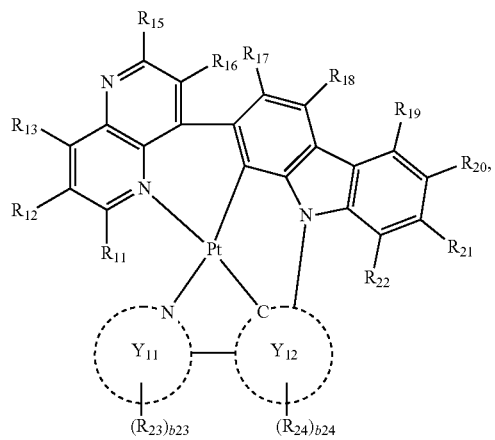

wherein, in Formulae 1-11 and 1-12, Y$_{11}$, Y$_{12}$, R$_{11}$ to R$_{24}$, b23, and b24 are the same as in Formula 1.

17. The organometallic compound of claim 16, wherein moieties represented by Y$_{11}$-Y$_{12}$ are selected from groups represented by Formulae 3-1 to 3-29:

3-1

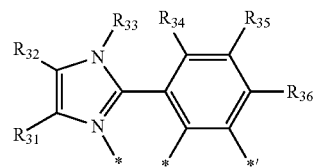

3-2

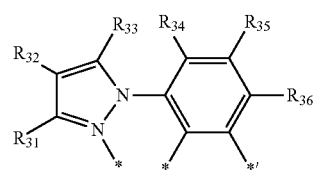

3-3

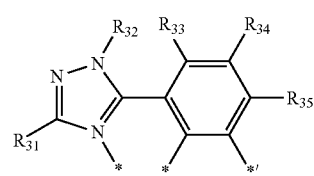

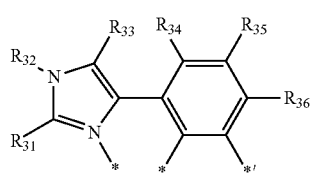
3-4
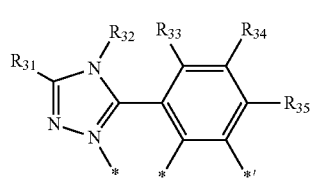
3-5
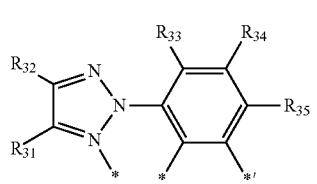
3-6
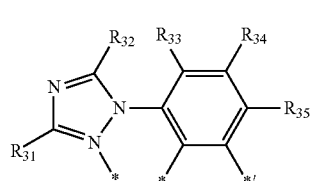
3-7
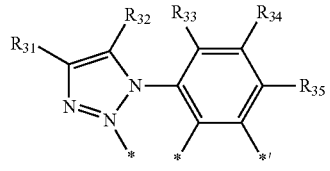
3-8
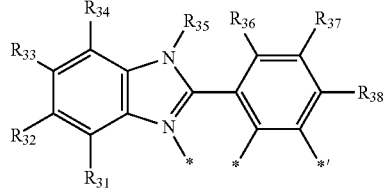
3-9
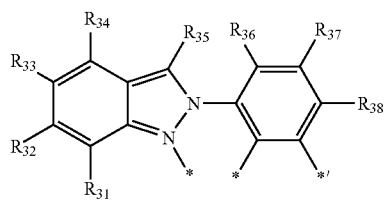
3-10
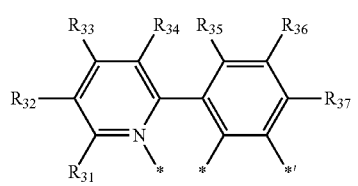
3-11
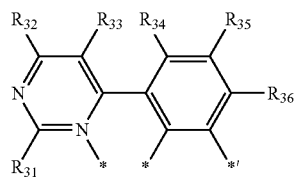
3-12
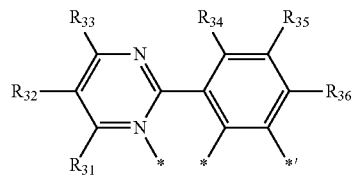
3-13
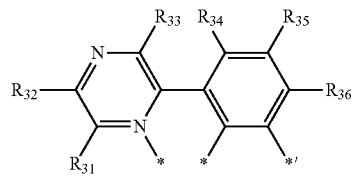
3-14
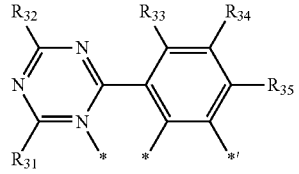
3-15
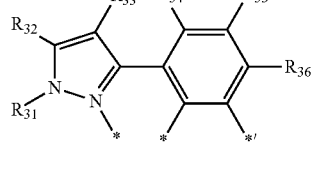
3-16
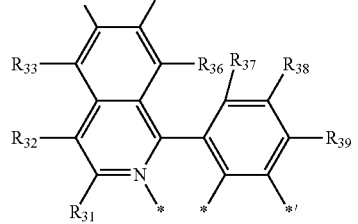
3-17
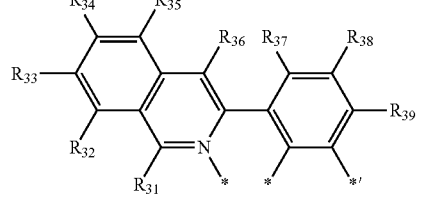
3-18
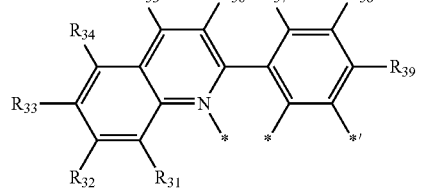
3-19

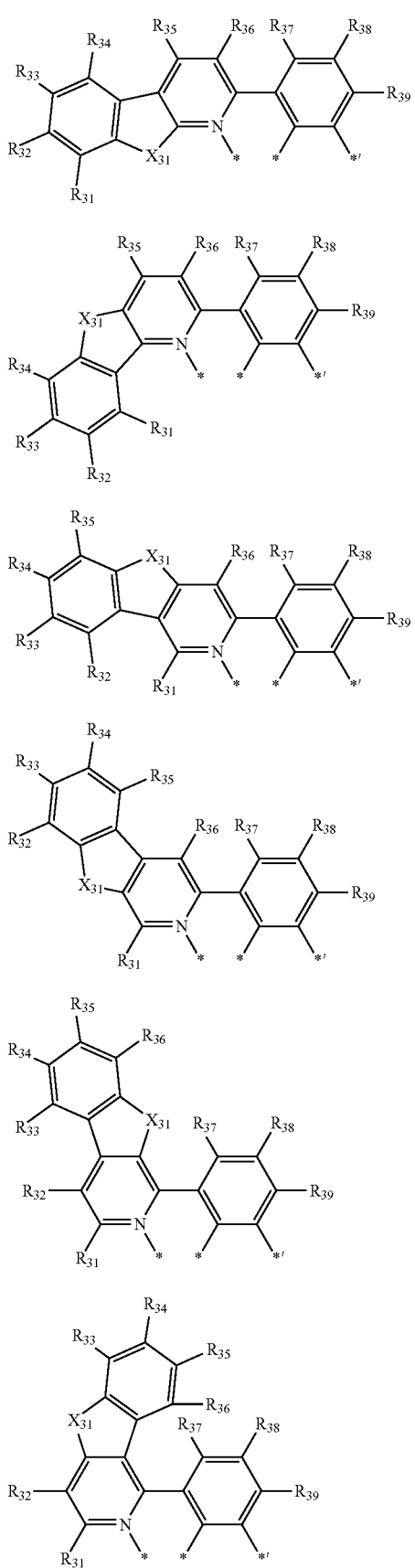

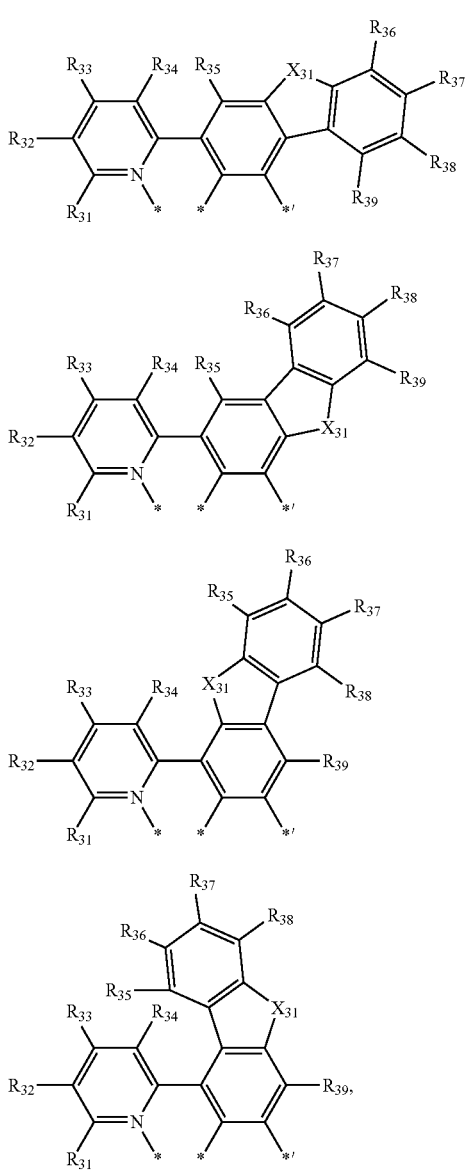

wherein, in Formulae 3-1 to 3-29, $X_{31}$ is selected from $C(R_{40})(R_{41})$, $N(R_{41})$, O, S, and $Si(R_{40})(R_{41})$;

$R_{31}$ to $R_{41}$ are each independently selected from hydrogen, deuterium, —F, a cyano group, a methyl group, an ethyl group, an n-propyl group, an iso-propyl group, an n-butyl group, an iso-butyl group, a sec-butyl group, a tert-butyl group, —CFH$_2$, —CF$_2$H, —CF$_3$, and a benzyl group;

a phenyl group, a biphenyl group, a terphenyl group, a naphthyl group, a pyridinyl group, a pyrimidinyl group, a pyridazinyl group, and a triazinyl group;

a phenyl group, a biphenyl group, a terphenyl group, a naphthyl group, a pyridinyl group, a pyrimidinyl group, a pyridazinyl group, and a triazinyl group, each substituted with at least one selected from deuterium, —F, a cyano group, a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, a pyridinyl group, a pyrimidinyl group, a pyridazinyl group, a triazinyl group, —Si($Q_{21}$)($Q_{22}$)($Q_{23}$), —Ge($Q_{21}$)($Q_{22}$)($Q_{23}$), and —N($Q_{21}$)($Q_{22}$); and —Si($Q_{31}$)($Q_{32}$)($Q_{33}$), —Ge($Q_{31}$)($Q_{32}$)($Q_{33}$), and —N($Q_{31}$)($Q_{32}$);

$Q_{21}$ to $Q_{23}$ and $Q_{31}$ to $Q_{33}$ are each independently selected from hydrogen, a methyl group, an ethyl group, an n-propyl group, an iso-propyl group, an n-butyl group, a phenyl group, a biphenyl group, and a terphenyl group;

* indicates a binding site to Pt in Formula 1-11 or 1-12; and

*' indicates a binding site to a neighboring nitrogen atom (N) in Formula 1-11 or 1-12.

18. The organometallic compound of claim 1, wherein the organometallic compound represented by Formula 1 is selected from Compounds 1 to 45:

1
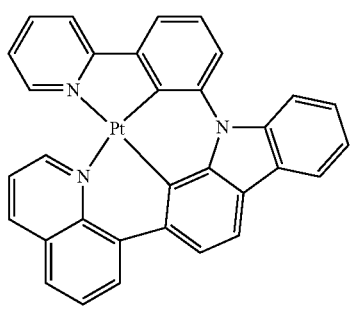

2
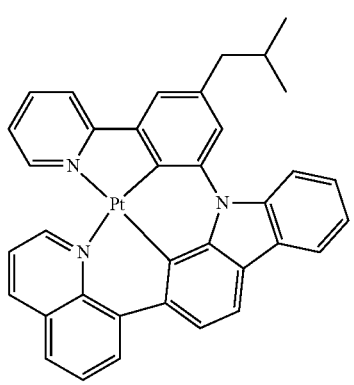

3
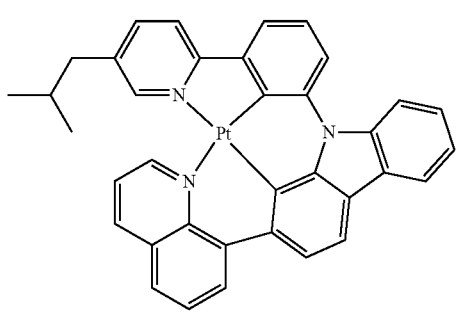

4
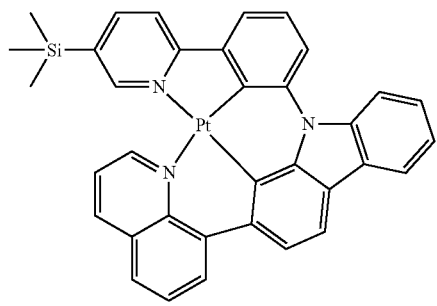

5
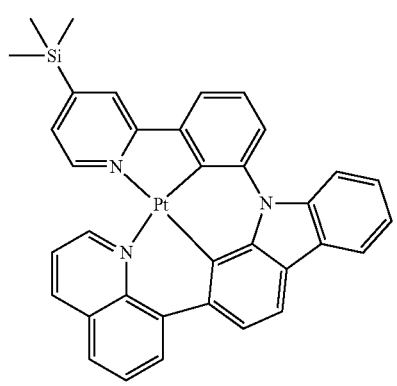

6
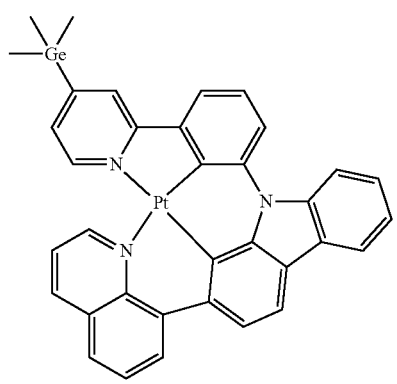

7
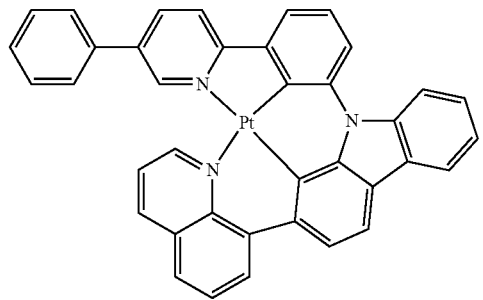

8
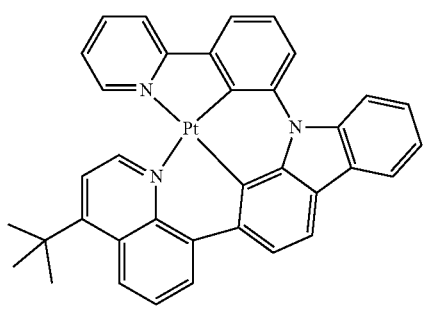
9
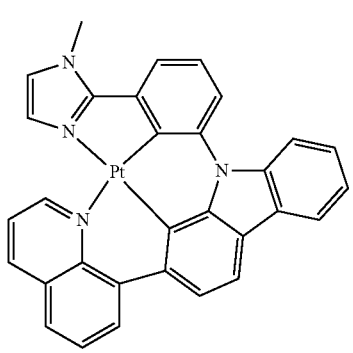
10
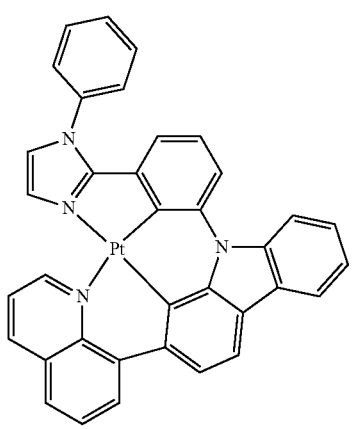
11
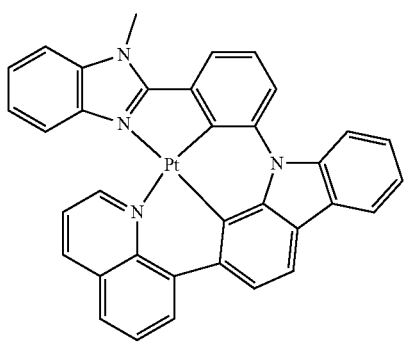
12
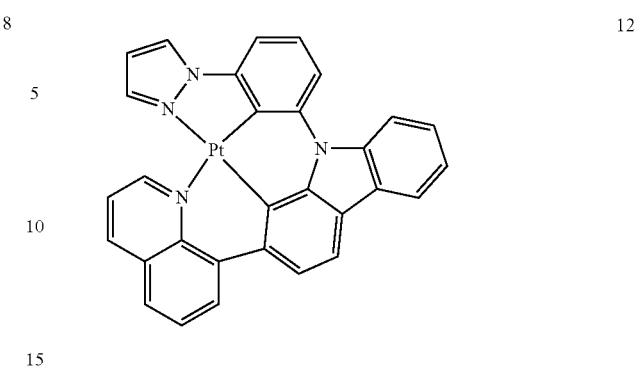
13
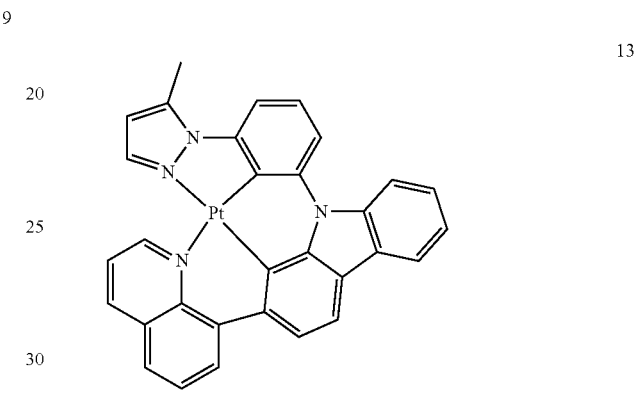
14
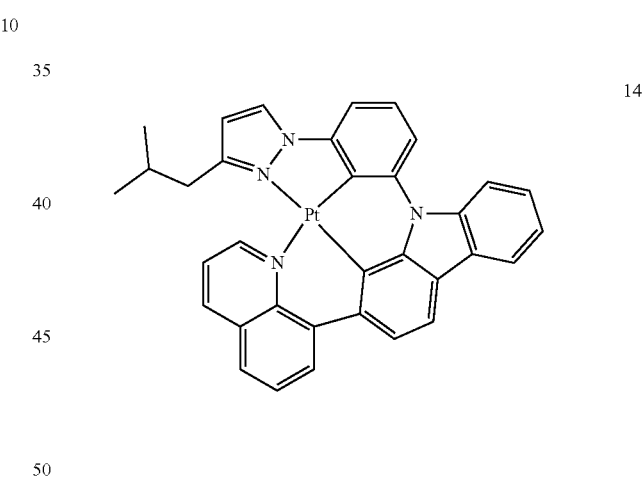
15
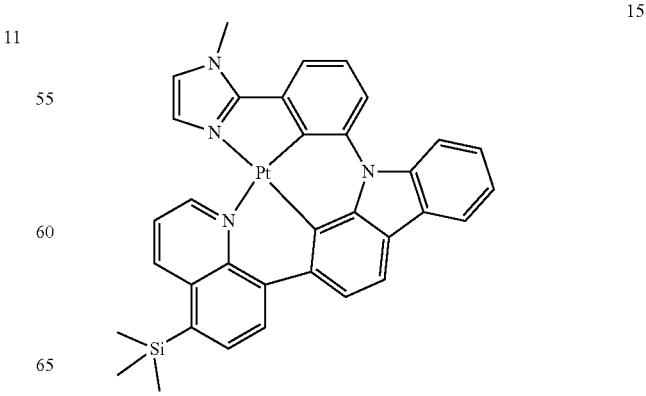

16
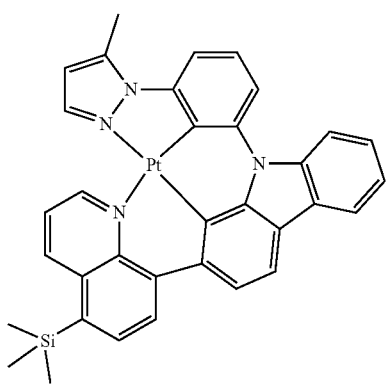
17
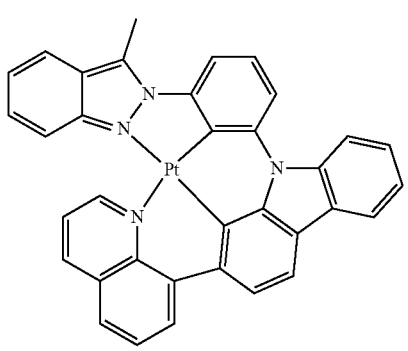
18
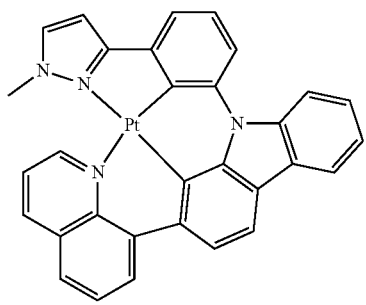
19
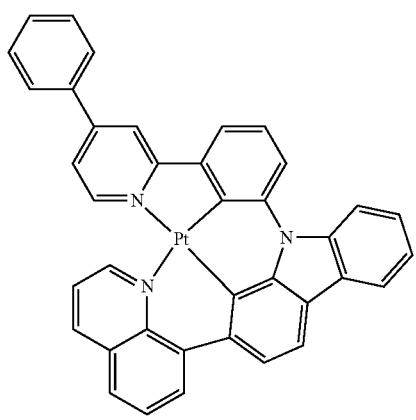
20
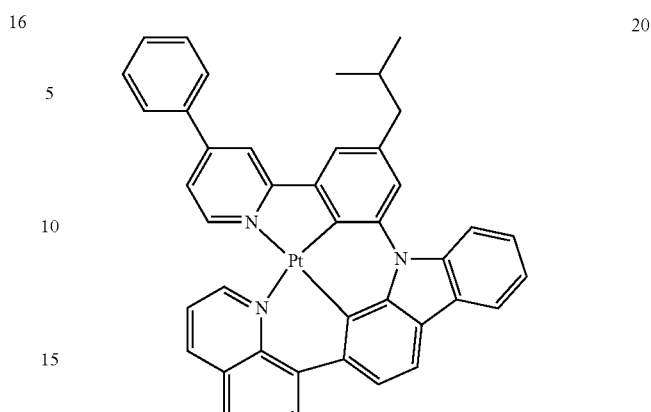
21
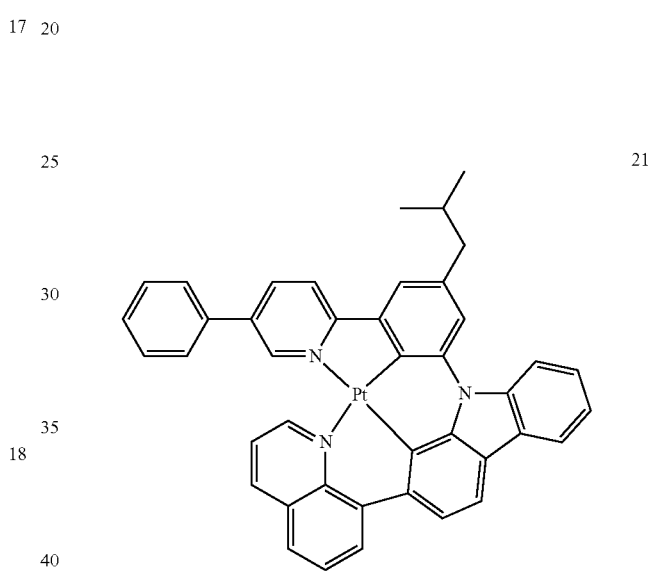
22
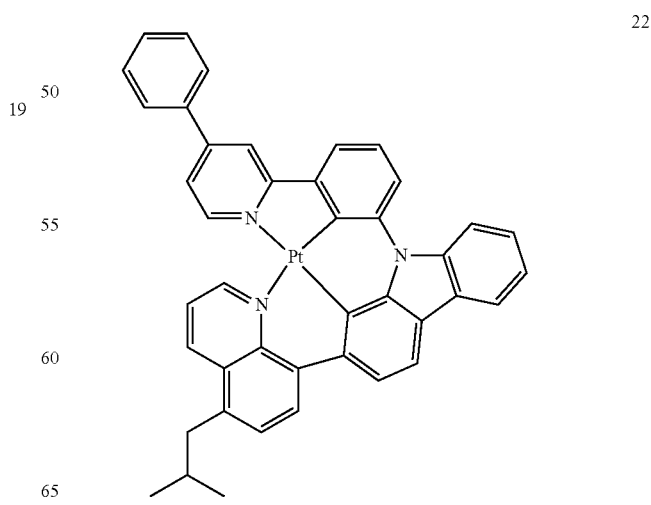

23
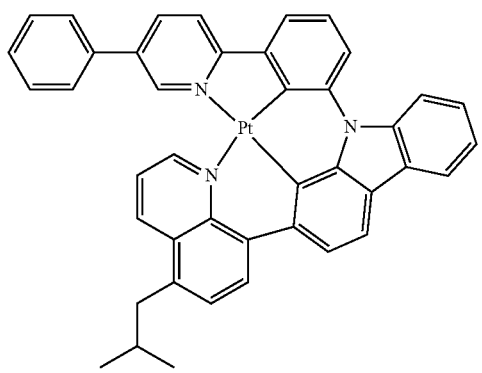
24
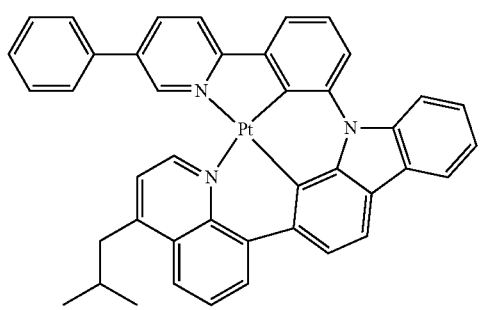
25
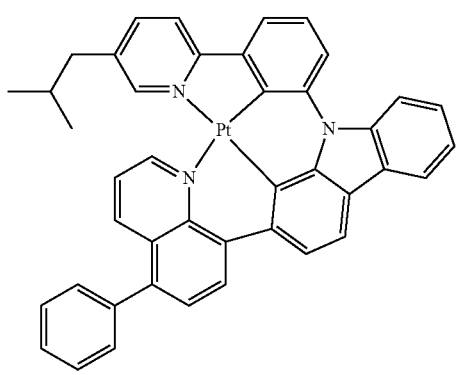
26
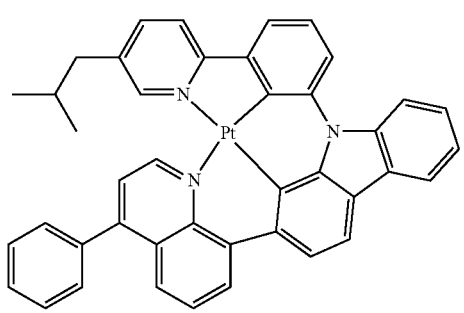
27
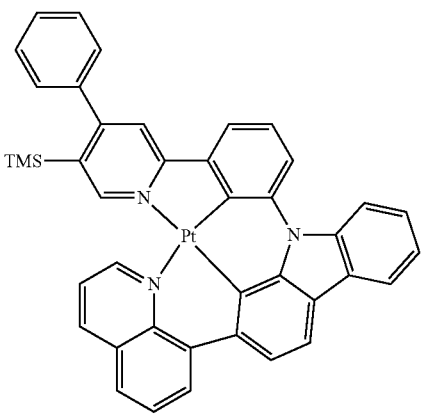
28
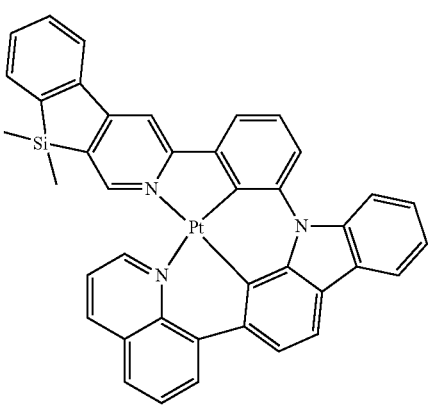
29
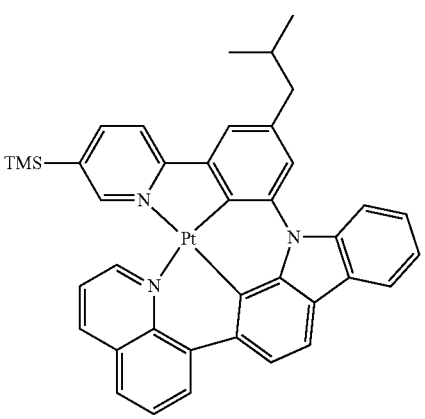
30
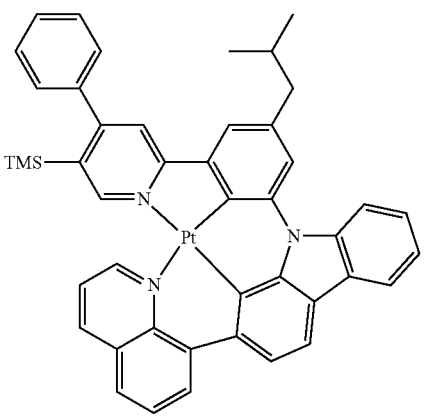

31
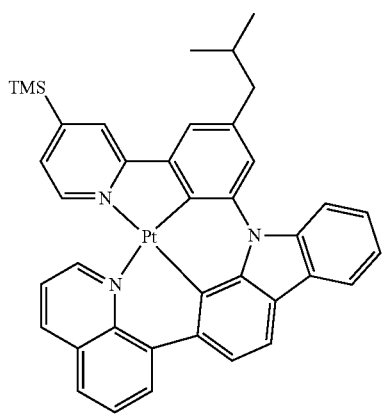
32
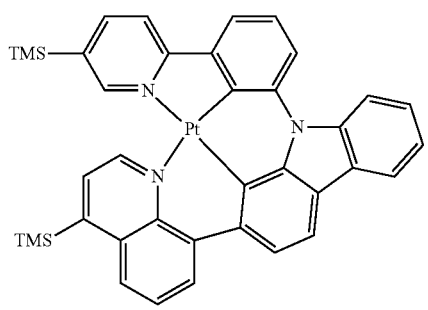
33
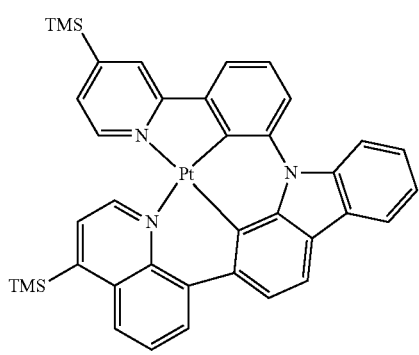
34
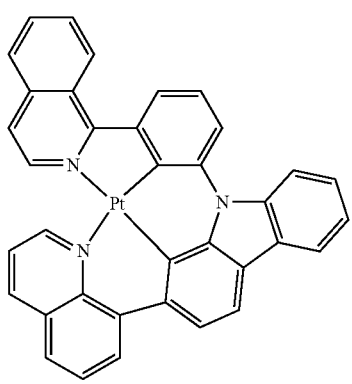
35
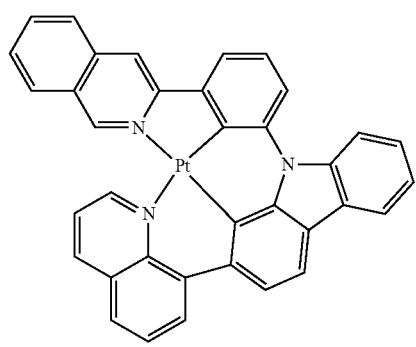
36
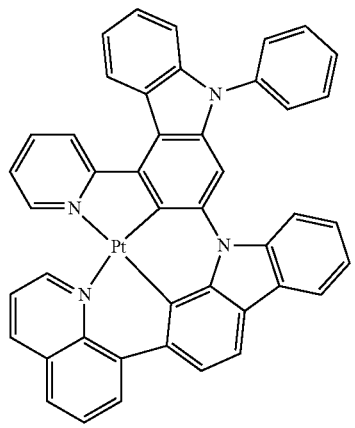
37
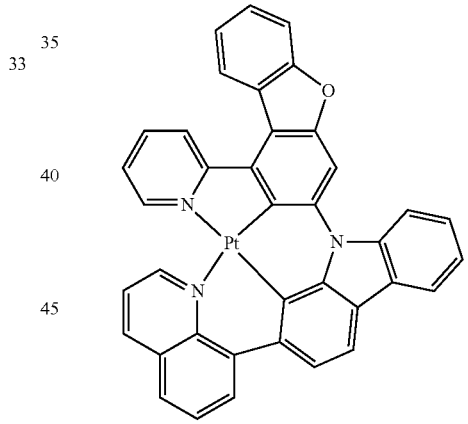
38
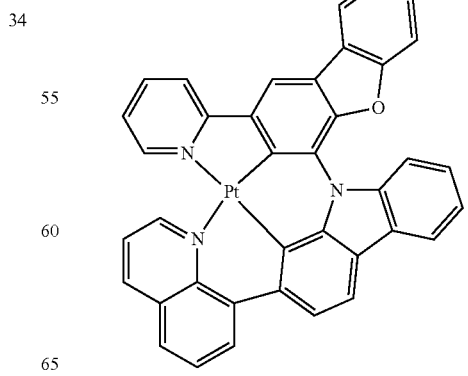

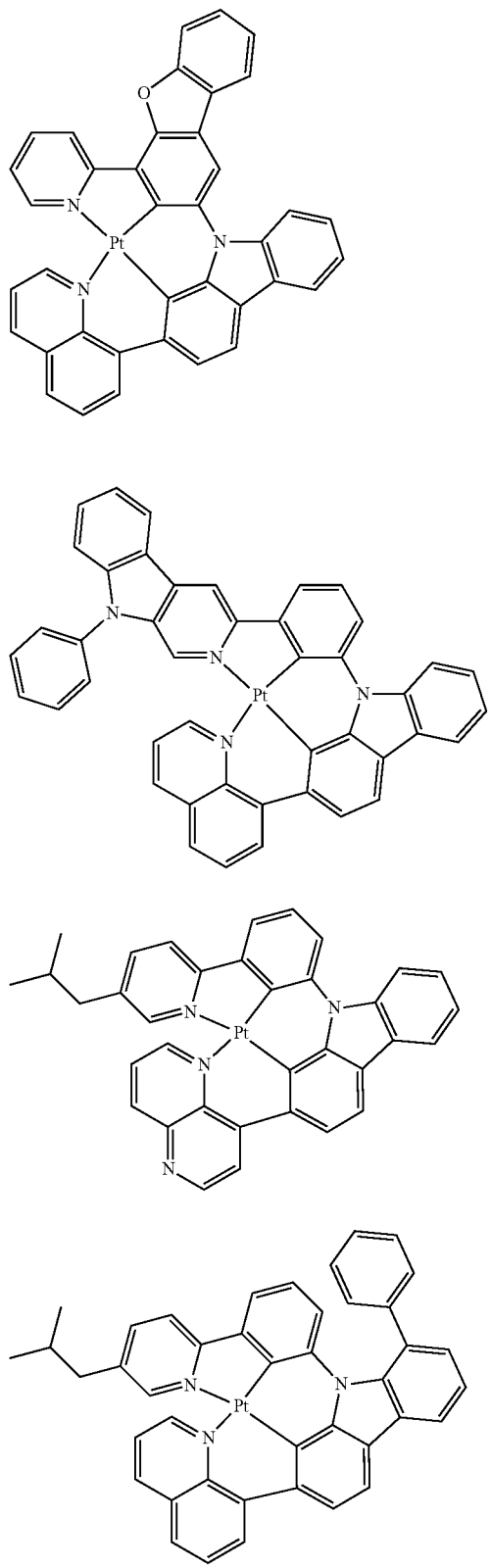

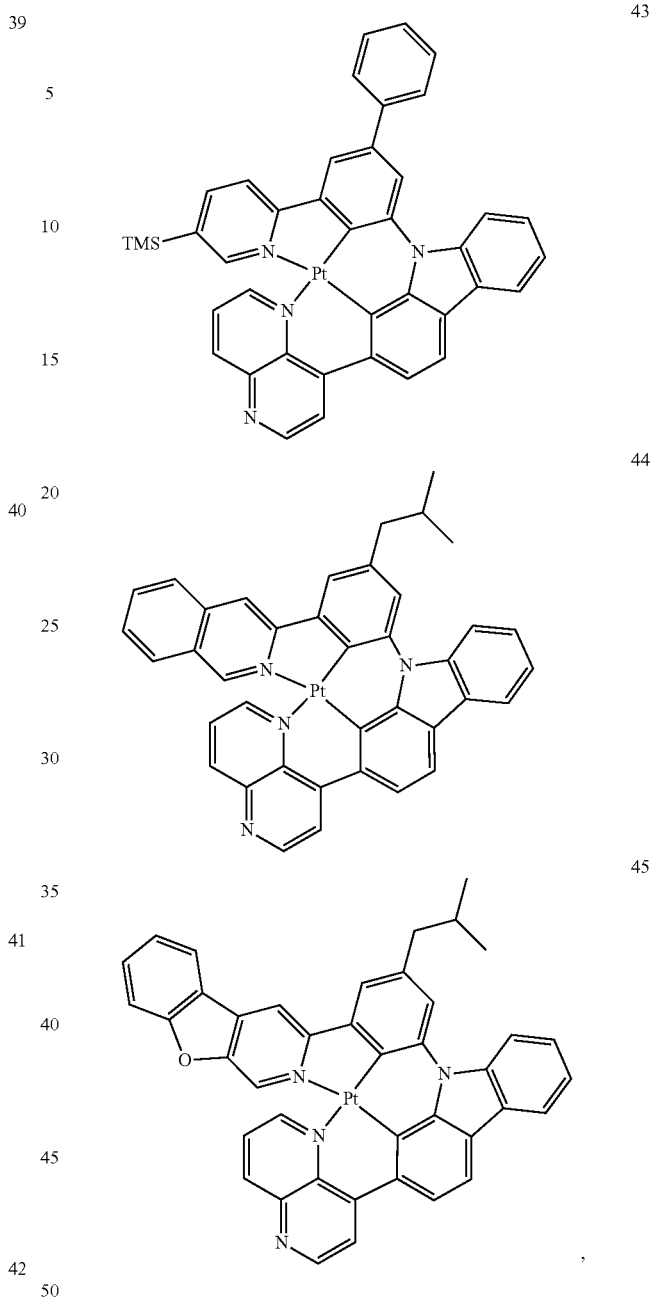

wherein, in Compound 1 to 45, TMS refers to a trimethylsilyl group (Si(CH$_3$)$_3$).

19. An organic light-emitting device comprising:
a first electrode;
a second electrode; and
an organic layer disposed between the first electrode and the second electrode,
wherein the organic layer comprises an emission layer and at least one organometallic compounds of claim 1.

20. The organic light-emitting device of claim 19, wherein the emission layer comprises the organometallic compound.

* * * * *